US009822180B2

(12) United States Patent
Cobbold et al.

(10) Patent No.: US 9,822,180 B2
(45) Date of Patent: Nov. 21, 2017

(54) IMMUNOTHERAPEUTIC MOLECULES AND USES

(71) Applicant: THE UNIVERSITY OF BIRMINGHAM, Birmingham (GB)

(72) Inventors: Mark Cobbold, Birmingham (GB); David Millar, Birmingham (GB)

(73) Assignee: THE UNIVERSITY OF BIRMINGHAM, Birmingham (GB)

(*) Notice: Subject to any disclaimer, the term of this patent is extended or adjusted under 35 U.S.C. 154(b) by 2 days.

(21) Appl. No.: 14/381,405

(22) PCT Filed: Feb. 28, 2013

(86) PCT No.: PCT/GB2013/050499
§ 371 (c)(1),
(2) Date: Aug. 27, 2014

(87) PCT Pub. No.: WO2013/128194
PCT Pub. Date: Sep. 6, 2013

(65) Prior Publication Data
US 2015/0183875 A1 Jul. 2, 2015

(30) Foreign Application Priority Data

Feb. 28, 2012 (GB) .................................. 1203442.7

(51) Int. Cl.
A61K 39/395 (2006.01)
C07K 16/28 (2006.01)
A61K 45/06 (2006.01)

(52) U.S. Cl.
CPC ...... *C07K 16/2896* (2013.01); *A61K 39/3955* (2013.01); *A61K 45/06* (2013.01); *C07K 16/2803* (2013.01); *C07K 16/2809* (2013.01); *C07K 2317/30* (2013.01); *C07K 2317/31* (2013.01); *C07K 2317/56* (2013.01); *C07K 2317/622* (2013.01); *C07K 2317/64* (2013.01)

(58) Field of Classification Search
None
See application file for complete search history.

(56) References Cited

U.S. PATENT DOCUMENTS

| 5,585,089 | A | 12/1996 | Queen et al. |
|---|---|---|---|
| 5,693,762 | A | 12/1997 | Queen et al. |
| 5,739,116 | A | 4/1998 | Hamann et al. |
| 5,767,285 | A | 6/1998 | Hamann et al. |
| 5,773,001 | A | 6/1998 | Hamann et al. |
| 7,151,164 | B2 | 12/2006 | Hansen et al. |
| 7,659,241 | B2 | 2/2010 | Senter et al. |
| 7,884,184 | B2 | 2/2011 | De Groot et al. |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 9,102,736 | B2* | 8/2015 | Hofmeister ........ C07K 16/2803 |
| 9,120,853 | B2 | 9/2015 | Lowman et al. |
| 9,127,053 | B2 | 9/2015 | West et al. |
| 9,169,321 | B2 | 10/2015 | Daugherty et al. |
| 2002/0187526 | A1* | 12/2002 | Ruben .................. C07K 14/715 435/69.5 |
| 2004/0001853 | A1 | 1/2004 | George et al. |
| 2004/0197336 | A1 | 10/2004 | Self |
| 2005/0037001 | A1 | 2/2005 | Germeraad et al. |
| 2006/0045881 | A1 | 3/2006 | Molldrem |
| 2006/0088522 | A1 | 4/2006 | Boghaert et al. |
| 2008/0107660 | A1 | 5/2008 | Self |
| 2009/0214543 | A1 | 8/2009 | Zangemeister-Wittke et al. |
| 2009/0304719 | A1 | 12/2009 | Daugherty et al. |
| 2010/0189651 | A1 | 7/2010 | Stagliano et al. |
| 2010/0291082 | A1 | 11/2010 | Zurawski et al. |
| 2011/0008840 | A1 | 1/2011 | Hoffee et al. |
| 2011/0178279 | A1* | 7/2011 | Williams ........... C07K 16/2863 530/388.22 |
| 2011/0229476 | A1 | 9/2011 | Liu et al. |
| 2013/0266568 | A1 | 10/2013 | Brinkmann et al. |
| 2013/0267686 | A1 | 10/2013 | Brinkmann et al. |
| 2013/0309230 | A1 | 11/2013 | Stagliano et al. |
| 2014/0023664 | A1 | 1/2014 | Lowman et al. |
| 2014/0024810 | A1 | 1/2014 | Stagliano et al. |
| 2014/0255313 | A1 | 9/2014 | Vasiljeva et al. |

(Continued)

FOREIGN PATENT DOCUMENTS

| EP | 0659438 A1 | 6/1995 |
|---|---|---|
| EP | 0871673 B1 | 4/2006 |

(Continued)

OTHER PUBLICATIONS

Thompson et al. (Drug Discovery Today, vol. 15, Nos. 11/12, Jun. 2010, pp. 468-473).*
Thompson et al. (mAbs 1:4, 348-356; Jul./Aug. 2009).*
Choi et al. (Expert Opinion on Biological Therapy, 11:7, 843-853).*
Salmeron et al. (J. Immunology, vol. 147, 1991, 3047-52).*
Kjer-Nielsen et al. (PNAS, 2004, 101,20,7675-7680, and supplemental Figs. 2 and 3).*
PDB locus 1SY6_A, 204 amino acids, Oct. 10, 2012, pp. 1-3.*
Thie et al. (PLoS ONE 6(1): e15921).*
Demichelis et al. (Appl Immunohistochem Mol Morphol. Jan. 2010;18(1):41-50).*
Jager et al., FEBS Letters 462 (1999) 307-312.*

(Continued)

*Primary Examiner* — Zachary Skelding
(74) *Attorney, Agent, or Firm* — McNeill Baur PLLC

(57) ABSTRACT

The invention provides molecule comprising: (i) a targeting moiety capable of directly or indirectly targeting to unwanted cells, and (ii) a further moiety that has a masked immune cell binding region so as to prevent binding of the further moiety to an immune cell, wherein the masked immune cell binding region is capable of being selectively unmasked when the molecule is in the vicinity of the unwanted cells so as to allow binding of the further moiety to an immune cell.

20 Claims, 14 Drawing Sheets

(56) References Cited

U.S. PATENT DOCUMENTS

Figure 1:
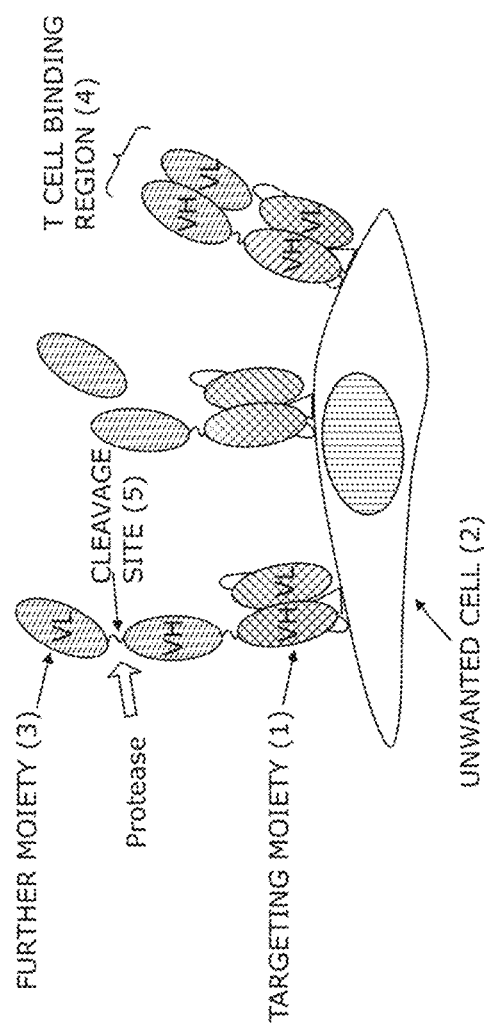

| | | |
|---|---|---|
| 2014/0363430 A1 | 12/2014 | West et al. |
| 2015/0005477 A1 | 1/2015 | Lowman et al. |
| 2015/0079088 A1 | 3/2015 | Lowman et al. |
| 2015/0087810 A1 | 3/2015 | Moore et al. |
| 2015/0118254 A1 | 4/2015 | Lowman et al. |
| 2015/0183875 A1 | 7/2015 | Cobbold et al. |
| 2015/0218217 A1 | 8/2015 | Moore et al. |
| 2016/0009817 A1 | 1/2016 | Wang et al. |
| 2016/0039942 A1 | 2/2016 | Cobbold et al. |
| 2016/0122425 A1 | 5/2016 | Daugherty et al. |
| 2016/0144042 A1 | 5/2016 | Williams et al. |
| 2016/0152711 A1 | 6/2016 | Williams et al. |

FOREIGN PATENT DOCUMENTS

| | | | |
|---|---|---|---|
| EP | 1948802 A1 | 7/2008 | |
| EP | 1664270 B1 | 5/2014 | |
| GB | 1216649 | 3/2014 | |
| WO | 9517212 | 6/1995 | |
| WO | 9517212 A1 | 6/1995 | |
| WO | 9634892 A1 | 11/1996 | |
| WO | 9723237 A1 | 7/1997 | |
| WO | 9810651 A1 | 3/1998 | |
| WO | 9818493 A2 | 5/1998 | |
| WO | 9824478 A2 | 6/1998 | |
| WO | 9841641 A1 | 9/1998 | |
| WO | 9902175 A1 | 1/1999 | |
| WO | 0006605 | 2/2000 | |
| WO | 0244197 | 6/2002 | |
| WO | 03027135 A2 | 4/2003 | |
| WO | 2004069876 A2 | 8/2004 | |
| WO | 2005052004 A2 | 6/2005 | |
| WO | 2005061547 A2 | 7/2005 | |
| WO | 2005083431 A2 | 9/2005 | |
| WO | 2005087813 A1 | 9/2005 | |
| WO | 2007057922 A1 | 5/2007 | |
| WO | 2007107764 A1 | 9/2007 | |
| WO | 2008019366 A2 | 2/2008 | |
| WO | 2008052322 A1 | 5/2008 | |
| WO | 2008097866 A2 | 8/2008 | |
| WO | 2009024771 A2 | 2/2009 | |
| WO | 2009025846 A2 | 2/2009 | |
| WO | 2008063113 | 7/2009 | |
| WO | 2010037837 A2 | 4/2010 | |
| WO | 2010077643 A1 | 7/2010 | |
| WO | 2010081173 A2 | 7/2010 | |
| WO | WO 2010081173 A2 * | 7/2010 | ............ C07K 16/00 |
| WO | 2011056721 A2 | 5/2011 | |
| WO | 2012123755 A1 | 9/2012 | |
| WO | 2013139789 A1 | 9/2013 | |
| WO | 2016014974 A2 | 1/2016 | |

OTHER PUBLICATIONS

Davol et al. (Clin Prostate Cancer. Sep. 2004;3(2):112-21).*
Wucherpfennig et al., Cold Spring Harb Perspect Biol. Apr. 2010;2(4):a005140.*
Gendler et al., Proc Natl Acad Sci U S A. Sep. 1987;84(17):6060-4.*
Moller et al., Eur. J. Biochem. 269, 1444-1455 (2002).*
Hoffmann et al., Int. J. Cancer: 128, 2096-2104 (2011).*
Offner et al., Molecular Immunology 43 (2006) 763-771.*
Varma et al., Immunity 25, 117-127, 2006.*
Trautmann, Nature Immunology, vol. 6, No. 12, 2005, pp. 1213-1214.*
Reinhard Hohlfeld 2010, Multiple Sclerosis 16(1) 3-14.*
Peters et al. (Curr Opin Immunol. Dec. 2011;23(6):702-6).*
Webb S, et al., "Pharma interest surges in antibody drug conjugates," Nat Biotechnol. Apr. 2011;29(4):297-8.
Witte, Monoclonal antibodies targeting the VEGF receptor-2 (Flk1/KDR) as an anti-angiogenic therapeutic strategy, Cancer and Metastasis Reviews 17:155-151 (1998).
Yu, Interaction between Bevacizumab and Murine VEGF-A: A Reassessment, Investigative Ophthalmology & Visual Science 49(2):522 (2008).
Chinese Office Action in corresponding CN application No. 201280024084.1, dated Jul. 21, 2015.
Non-Final Office Action in corresponding U.S. Appl. No. 14/005,452, dated Jul. 31, 2015.
Adis R&D Profile: Brentuximab Vedotin, Drugs RD 11(1):85-95 (2011).
Alexander, J., et al., "Linear PADRE T Helper Epitope and Carbohydrate B Cell Epitope Conjugates Induce Specific High Titer IgG Antibody Responses," J. Immunol. 164:1625-1633 (2000).
Baeuerle P.A., et al. "BiTE: Teaching antibodies to engage T-cells for cancer therapy." Curr Opin Mol Therapeutics. 11 (1):22-30 (Feb 1, 2009).
Baeuerle, P.A. and Reinhardt, C., "Bispecific T-Cell Engaging Antibodies for Cancer Therapy," Cancer Res. 69 ( 12):4941-4944 (2009).
Bargou, R., et al., "Tumor Regression in Cancer Patients by Very Low Doses of a T-Cell Engaging Antibody," Science 321:974-977 (2008).
Bellosillo, B., et al., "Complement-Mediated Cell Death Induced by Rituximab in B-Cell Lymphoproliferative Disorders is Mediated in vitro by a Caspase-Independent Mechanism Involving the Generation of Reactive Oxygen Species," Blood 98(9):2771-2777 (2001).
Bertilaccio, M.T.S., et al., "A Novel Rag2 -Gamma2- Xenograft Model of Human CLL," Blood 115(8):1605-1609 (2010).
Bonnet, D. and Dick, J.E., "Human Acute Myeloid Leukemia is Organized as a Hierarchy that Originates from a Primitive Hematopoietic Cell," Nat. Med. 3(7):730-737 (1997).
Bruhl, H., et al., "Depletion of CCR5-Expressing Cells with Bispecific Antibodies and Chemokine Toxins: A New Strategy in the Treatment of Chronic Inflammatory Diseases and HIV," The Journal of Immunology, vol. 166, pp. 2420-2426 (2001).
Carter, P.J., "Introduction to Current and Future Protein Therapeutics: A Protein Engineering Perspective," Exp. Cell Res. 317:1261-1269 (2011).
Carter, P.J., "Potent Antibody Therapeutics by Design," Nat. Rev. Immunol 6:343-357 (2006).
Clark, E.A., et al., "Role ofBp35 Cell Surface Polypeptide in Human B-Cell Activation," Proc. Natl. Acad. Sci. 82: 1766-1770 (1985).
Clarke, et al., "Gemtuzumab Ozogamicin: Is There Room for Salvage?" Blood 116(14):2618-2619 (2010).
De Groot, A.S., et al., "Activation of Natural Regulatory T Cells by IgG Fe-derived Peptide 'Tregitopes'," Blood 112 (8):3303-3311 (2008).
Donda, A., et al., "In vivo Targeting of an Anti-Tumor Antibody Coupled to Antigenic MHC Class I Complexes Induces Specific Growth Inhibition and Regression of Established Syngeneic Tumor Grafts," Cancer Immunity 3:11 (2003).
Duncan RJS et al., "A new reagent which may be used to introduce sulfhydryl groups into proteins, and its use in the preparation of conjugates for immunoassay," Analytical Biochemistry, 132(1):68-73 (Jul. 1, 1983).
Eberl, G., et al., "An Anti-CD19 Antibody Coupled to a Tetanus Toxin Peptide Induces Efficient Fas Ligand (FasL)-Mediated Cytotoxicity of a Transformed Human B Cell Line by Specific CD4+ T Cells," Clinical and Experimental Immunology 114:173-178 (1998).
Eno-Amooquaye, E.A., et al., "Altered Biodistribution of an Antibody-Enzyme Conjugate Modified with Polyethylene Glycol," Br. J. Cancer 73:1323-1327 (1996).
Fattah, O.M., et al., "Peptabody-EGF: A Novel Apoptosis Inducer Targeting ErbB 1 Receptor Overexpressing Cancer Cells," Int. J. Cancer 119:2455-2463 (2006).
Germain, C., et al., "MHC Class I-Related Chain A Conjugated to Antitumor Antibodies can Sensitize Tumor Cells to Specific Lysis by Natural Killer Cells," Clin. Cancer Res. 11(20):7516-7522 (2005).
Giovannoni, L., et al., "Isolation of Anti-angiogenesis Antibodies from a Large Combinatorial Repertoire by Colony Filter Screening," Nucleic Acids Research 29(5):E27 (2001).

(56) References Cited

OTHER PUBLICATIONS

Hellstrom, I., et al., "Monoclonal Mouse Antibodies Raised Against Human Lung Carcinoma," Cancer Research 46:3917-3923 (1986).
Hislop, A.D., et al., "Cellular Responses to Viral Infection in Humans: Lessons from Epstein-Barr Virus," Annu. Rev. Immunol. 25:587-617 (2007).
Howland, S.W., et al., "Inducing Efficient Cross-Priming Using Antigen-Coated Yeast Particles," J. Immunother. 31 (7):607-619 (2008).
Hughes, B., "Antibody-Drug Conjugates for Cancer: Poised to Deliver?," Nature Reviews Drug Discovery 9:665-667 (2010).
International Preliminary Report on Patentability for International Application PCT/GB2012/050577; dated Sep. 17, 2013.
International Preliminary Report on Patentability for PCT/GB2013/050499 dated Sep. 2, 2014.
International Search Report and Written Opinion of the International Searching Authority for International Application No. PCT/GB2012/050577, "Re-Directed Immunotherapy," dated Jun. 29, 2012.
International Search Report for PCT/GB2013/050499 dated Jul. 24, 2013.
Irvine, D.J., et al., "Direct Observation of Ligand Recognition by T Cells," Nature 419:845-849. (2002).
Jeffrey, S.C., et al., "Dipeptide-Based Highly Potent Doxorubicin Antibody Conjugates," Bioorganic & Medicinal Chemistry Letters 16:358-362 (2006).
Kawamura, K.S., et al., "In Vivo Generation of Cytotoxic T Cells from Epitopes Displayed on Peptide-Based Delivery Vehicles," Journal of Immunology 168:5709-5715 (2002).
Kohler, et al., "Continuous Cultures of Fused Cells Secreting Antibody of Predefined Specificity," Nature 256:495-497 (1975).
Kozak, R.W., et al., "IL-2-PE40 Prevents the Development of Tumors in Mice Injected with IL-2 Receptor Expressing EL4 Transfectant Tumor Cells," Journal of Immunology 145 (8):2766-2771 (1990).
Kufer, P., et al., "Construction and Biological Activity of a Recombinant Bispecific Single-Chain Antibody Designed for Therapy of Minimal Residual Colorectal Cancer," Cancer Immunology Immunotherapy, vol. 45, pp. 193-197 (1997).
Larche, M., et al., "Functional Evidence for a Monoclonal Antibody that Binds to the Human IL-4 Receptor," Immunology 65:617-622 (1988).
Lash, A., "Making the Case for Antibody-Drug Conjugates," In Vivo: The Business and Medicine Report:32-38 (2010).
Loffler et al. "A recombinant bispecific single-chain antibody, CD19 x CD3, induces rapid and high lymphoma-directed cytotoxicity by unstimulated T lymphocytes." 95(6):2098-103. (Mar. 15, 2000).
Loffler, A. et al., "A Recombinant Bispecific Single-Chain Antibody, CD19 X CD3, Induces Rapid and High Lymphoma-Directed Cytotoxicity by Unstimulated T Lymphocytes," Blood Journal, 95(6): 2098-20103 (Mar. 15, 2000).
Loisel, S., et al., "Establishment of a Novel Human B-CLL-like Xenograft Model in Nude Mouse," Leukemia Research 29:1347-1352 (2005).
Lorberboum-Galski, H., et al., "Cytotoxic Activity of an Interleukin 2-Pseudomonas Exotoxin Chimeric Protein Produced in *Escherichia coli*," Proc. Natl. Acad. Sci 85: 1922-1926 (1988).
Lutterbuese R. et al., "T cell-engaging BiTE antibodies specific for EGFR potently eliminate KRAS- and BRAF-mutated colorectal cancer cell", Proc. Natl. Acad. Sci. 107(28):12605-12610. (Jul. 13, 2010).
Lutterbuese, R., et al., "Potent Control of Tumor Growth by CENCD3-bispecific Single-Chain Antibody Constructs that are not Competitively Inhibited by Soluble CEA," J. Immunother. 32(4):341-352 (2009).
Mack, M., et al., "A Small Bispecific Antibody Construct Expressed as a Functional Single-Chain Molecule With High Tumor Cell Cytotoxicity," Proceedings of the National Academy of Sciences, vol. 93, pp. 7021-7025 (Jul. 1995).

Mack, M., et al., "Biologic Properties of a Bispecific Single-Chain Anitbody Directed Against 17-1A (EpCAM) and CD3; Tumor Cell-Dependent T Cell Stimulation and Cytotoxic Activity," the Journal of Immunology, vol. 158, pp. 3965-3971 (1997).
Mahato, R., et al., "Prodrugs for Improving Tumor Targetability and Efficiency," Adv. Drug. Deily. Rev. 63(8):659-670 (2011).
Matsumura, Y. and Maeda, H., "A New Concept for Macromolecular Therapeutics in Cancer Chemotherapy: Mechanism of Tumoritropic Accumulation of Proteins and the Antitumor Agent Smancs," Cancer Res. 46:6387-6392 (1986).
Mayes, S., et al., "New Antibody Drug Treatments for Lymphoma," Expert Opin. Biol. Ther. 11 ( 5):623-640 (2011 ).
Melton, R.G., et al., "Covalent Linkage of Carboxypeptidase G2 to Soluble Dextrams-1," Biochemical Pharmacology 36 (1):105-112 (1987).
Meziere, C., et al., "In Vivo T Helper Cell Response to Retro-Inverso Peptidomimetics," J. Immunol. 159:3230-323 7 (1997).
Molhoj et al. "CD19-/CD3-bispecific antibody of the BiTE class is far superior to tandem diabody with respect to redirected tumor cell lysis", Mol Immunol. 44(8):1935-1943. (Dec 1, 2006).
Moore, P.A., et al., "Application of Dual Affinity Retargeting Molecules to Achieve Optimal Redirected T-Cell Killing of B-Cell Lymphoma," Blood 117(17):4542-4551 (2011).
Murphy, G., "The ADAMs: Signalling Scissors in the Tumour Microenvironment," Nature Reviews Cancer 8:929-941 (2008).
Ogg, G.S., et al., "Sensitization of Tumour Cells to Lysis by Virus-Specific CTL using Antibody-Targeted MHC Class I/Peptide Complexes," British Journal of Cancer 82( 5): 105 8-1062 (2000).
O'Sullivan, M.J., et al., "Comparison of Two Methods of Preparing Enzyme-Antibody Conjugates: Application of these Conjugates for Enzyme Immunoassay," Analytical Biochemistry 100: 100-108(1979).
Park, B.-W., et al., "Rationally Designed Anti-HER2/neu Peptide Mimetic Disables P185HER2/neu Tyrosine Kinases in vitro and in vivo," Nature Biotechnology 18: 194-198 (2000).
Plant, A, et al., "Phospholipid/Alkanethiol Bilayers for Cell-Surface Receptor Studies by Surface Plasmon Resonance," Analytical Biochemistry, vol. 226, pp. 342-348 (1995).
Ponde, D.E., et al., "Development of Anti-EGF Receptor Peptidomimetics (AERP) as Tumor Imaging Agent," Bioorganic & Medicinal Chemistry Letters 21 :2550-2553 (2011 ).
Porcelli, S., et al., "Recognition of Cluster of Differentiation 1 Antigens by Human CD4-CD8-Cytolytic T Lymphocytes," Nature 341:447-450 (1989).
Rader, C., "DARTs Take Aim at BiTEs," Blood 117:4403-4404 (2011).
Rawlings, N.D., et al., "MEROPS: the Peptidase Database," Nucleic Acids Research 36:D320-D325 (2008).
Rich, D.H., "Inhibitors of cysteine proteases." In Research monographs in cell and tissue physiology vol. 12, Proteinase inhibitors. Barrett AJ, Salvesen G, eds. (Amsterdam: Elsevier.) pp. 153-178 (1986).
Romagnoli, P., et al., "Selective Interaction of Ni with an MHC-Bound Peptide," The EMBO Journal 10(6):1303-1306 (1991).
Romero, P., et al., "Photoaffinity Labeling of the T Cell Receptor on Living Cytotoxic T Lymphocytes," The Journal of Immunology 150(9):3825-3831 (1993).
Savage, P., et al., "Induction of Viral and Tumour Specific CTL Responses Using Antibody Targeted HLA Class I Peptide Complexes," British Journal of Cancer 86:1336-1342 (2002).
Schaffitzel, C., et al., "Ribosome Display: an in vitro Method for Selection and Evolution of Antibodies from Libraries," Journal of Immunological Methods 231 :119-135 (1999).
Schmiegel, W., et al., "Cytokine-Mediated Enhancement of Epidermal Growth Factor Receptor Expression Provides an Immunological Approach to the Therapy of Pancreatic Cancer," Proc. Natl. Acad. Sci. 94:12622-12626 (1997).
Searle, F., et al., "A Human Choriocarcinoma Xenograft in Nude Mice; a Model for the Study of Antibody Localization," British Journal Cancer 44: 13 7-144 (1981 ).
Senter, P.D., et al., "Anti-Tumor Effects of Antibody-Alkaline Phosphatase Conjugates in Combination with Etoposide Phosphate," Proc. Natl. Acad. Sci. 85:4842-4846 (1988).

(56) References Cited

OTHER PUBLICATIONS

Shen, L., et al., "Important Role of Cathepin S in Generating Peptides for TAP-Independent MHC Class I Crosspresentation In Vivo," Immunity 21:155-165 (2004).
Sherman, D.B. and Spatola, A.F., "Compatibility of Thioamides with Reverse Turn Features: Synthesis and Conformational Analysis of Two Model Cyclic Pseudopeptides Containing Thioamides as Backbone Modifications," J. Am. Chem. Soc. 112:433-441 (1990).
Small, E.J., et al., "Placebo-Controlled Phase III Trial of Immunologic Therapy with Sipuleucel-T (APC8015) in Patients with Metastatic, Asymptomatic Hormone Refractory Prostate Cancer," Journal of Clinical Oncology 24(19):3089-3094 (2006).
Smith, D.C., et al., "Exogenous Peptides Delivered by Ricin Require Processing by Signal Peptidase for Transporter Associated with Antigen Processing-Independent MHC Class I restricted Presentation," J. Immunol. 169:99-107 (2002).
Staerz, U., et al., "Hybrid Antibodies Can Target Sites for Attack by T Cells," Nature, vol. 314, pp. 628-631 (Apr. 1985).
Staerz, U.D. and Bevan, M.J., "Hybrid Hybridoma Producing a Bispecific Monoclonal Antibody that can Focus Effector T-Cell Activity," Proc. Natl. Acad. Sci 83: 1453-1457 (1986).
Stirnemann, K., et al., "Sustained Activation and Tumor Targeting of NKT Cells Using a CDldanti-HER2-scFv Fusion Protein Induce Antitumor Effects in Mice," The Journal of Clinical Investigation 118(3 ):994-1005 (2008).
Sykulev, Y., et al., "Evidence that a Single Peptide-MHC Complex on a Target Cell can Elicit a Cytolytic T Cell Response," Immunity 4:565-571 (1996).
Sylwester, A.W., et al., "Broadly Targeted Human Cytomegalovirus-Specific CD4+ and CD8+ T Cells Dominate the Memory Compartments of Exposed Subjects," The Journal of Experimental Medicine 202(5):673-685 (2005).
Thorsett, E.D., et al., "Dipeptide Mimics. Conformationally Restricted Inhibitors of Angiotensin-Converting Enzyme," Biochemical and Biophysical Research Communications 111(1):166-171(1983).
Tosolini, M., et al., "Clinical Impact of Different Classes of Infiltrating T Cytotoxic and Helper Cells (Thl, Th2, Treg, Thl 7) in Patients with Colorectal Cancer," Cancer Res. 71 (4):1263-1271 (2011).
Veber, D.F ., et al., "Conformationally Restricted Bicyclic Analogs of Somatostatin," Proc. Natl. Acad. Sci. 75 (6):2636-2640 (1978).
Vita, R., et al., "The Immune Epitope Database 2.0," Nucleic Acids Research 38:D854-D862 (2010).
Waldman, T.A., et al., "Immune Receptors: Targets for Therapy of Leukemia/Lymphoma, Autoimmune Diseases and for the Prevention of Allograft Rejection," Annu. Rev. Immunol. 10:675-704 (1992).
Wang, Q.-C., et al., "Induction of Hepatitis C Virus-Specific Cytotoxic T and B Cell Responses by Dendritic Cells Expressing a Modified Antigen Targeting Receptor," World Journal of Gastroenterology 11(4):557-560 (2005).
Winter, G., et al., "Making Antibodies by Phage Display Technology," Annu. Rev. Immunol. 12:433-455 (1994).
Written Opinion of the International Searching Authority for PCT/GB2013/050499 dated Jul. 24, 2013.
Zhou, X., et al., "The Role of Complement in the Mechanism of Action of Rituximab for B-Cell Lymphoma: Implications for Therapy," The Oncologist 13:954-966 (2008).
Alderson RF, et al. CAT-8015: a second-generation pseudomonas exotoxin A-based immunotherapy targeting CD22-expressing hematologic malignancies. Clin Cancer Res. 15(3):832-9. Feb. 1, 2009.
Alegretti AP, et al. Expression of CD55 and CD59 on peripheral blood cells from systemic lupus erythematosus (SLE) patients. Cell Immunol. 265(2):127-32. 2010; Epub Aug. 2, 2010.
Alisa A, et al. "Human CD4(+) T cells recognize an epitope within alpha-fetoprotein sequence and develop into TGF-beta-producing CD4(+) T cells," J Immunol. Apr. 1, 2008;180(7):5109-17.

Appay V. The physiological role of cytotoxic CD4(+) T-cells: the holy grail? Clin Exp Immunol. 138(1):10-13. 2004.
Arai K, et al., "Preventing effect of anti-ICAM-1 and anti-LFA-1 monoclonal antibodies on murine islet allograft rejection," International Journal of Pancreatology, Aug. 1999, vol. 26, Issue 1, pp. 23-31.
Ariel O, et al. Signal transduction by CD58: the transmembrane isoform transmits signals outside lipid rafts independently of the GPI-anchored isoform. Cell Signal. 21(7):1100-8. Jul 2009. Epub Mar. 5, 2009.
Becker-Herman S, et al. CD74 is a member of the regulated intramembrane proteolysis-processed protein family. Mol Biol Cell. 16(11):5061-9. Nov. 2005. Epub Aug. 17, 2005.
Borche L, et al. CD43 monoclonal antibodies recognize the large sialoglycoprotein of human leukocytes. Eur J Immunol. 17(10):1523-6. Oct. 1987.
Brodsky FM. A matrix approach to human class II histocompatibility antigens: reactions of four monoclonal antibodies with the products of nine haplotypes. Immunogenetics. 19(3):179-94. 1984.
Cochran, Domain-level antibody epitope mapping through yeast surface display of epidermal growth factor receptor fragments, J of Immunological Methods 287:147-158 (2004).
Deckert M, et al. CD59 molecule: a second ligand for CD2 in T cell adhesion. Eur J Immunol. 22(11):2943-7. Nov. 1992.
Dermer, Another anniversary for the war on cancer, Bio/technology 12:320 (1994).
Engleman EG, et al. Studies of a human T lymphocyte antigen recognized by a monoclonal antibody. Proc Natl Acad Sci U S A. 78(3):1791-5. Mar. 1981.
Epstein AL, et al. Two new monoclonal antibodies (LN-1, LN-2) reactive in B5 formalin-fixed, paraffin-embedded tissues with follicular center and mantle zone human B lymphocytes and derived tumors. J Immunol. 133 (2):1028-1036. Aug. 1984.
European Office Action in corresponding EP Application No. 12718715.1, dated Jul. 23, 2015.
First Office Action and Search Report from the State Intellectual Property Office of the People's Republic of China for Application No. 201280024084.1, issued Nov. 15, 2014 (18 pages).
Fluhr H, et al. Interferon-gamma and tumor necrosis factor-alpha sensitize primarily resistant human endometrial stromal cells to Fas-mediated apoptosis. J Cell Sci. 120(Pt 23):4126-33. Dec. 1, 2007; Epub Nov. 14, 2007.
Ghankekar et al., Gamma Interferon Expression in CD8+ T Cells is a Marker for Circulating Cytotoxic T Lymphocytes that Recognize an HLA A2-Restricted Epitope of Human Cytomegalovirus Phosphoprotein p65, Clin Diagn Lab Immunol 8(3):628-31 (2001).
Golay, Mechanisms of action of therapeutic monoclonal antibodies: promises and pitfalls of in vitro and in vivo assays, Archives of Biochemistry and Biophysics 526:146-153 (2012).
Grimbert P. Thrombospondin/CD47 interaction: a pathway to generate regulatory T cells from human CD4+ CD25− T cells in response to inflammation. J Immunol. 177(6):3534-41. Sep. 15, 2006.
Gura, Systems for identifying new drugs are often faulty, Science 278:1041-1042 (1997).
Horie R, Watanabe T. CD30: expression and function in health and disease. Semin Immunol. 10(6):457-70. Dec. 1998.
International Search Report for PCT/GB2013/052427 dated May 2, 2014.
Jilaveanu LB, et al. CD70 expression patterns in renal cell carcinoma. Hum Pathol. 43(9):1394-9. Sep. 2012; Epub Mar. 7, 2012.
Jubala, CD20 Expression in Normal Canine B Cells and in Canine non-Hodgkin Lymphoma, Vet Pathol 42:468-476 (2005).
Jutila MA, et al. L-selectin serves as an E-selectin ligand on cultured human T lymphoblasts. J Immunol. 169 (4):1768-73. Aug. 15, 2002.
Klechevsky E, et al. Cross-priming CD8+ T cells by targeting antigens to human dendritic cells through DCIR. Blood. 116(10):1685-97. Sep. 9, 2010; Epub Jun. 7, 2010.
Kreitman RJ, et al. Phase I trial of anti-CD22 recombinant immunotoxin moxetumomab pasudotox (CAT-8015 or HA22) in patients with hairy cell leukemia. J Clin Oncol. 230(15):1822-8. May 20, 2012; Epub Feb. 21, 2012.

(56) References Cited

OTHER PUBLICATIONS

Lagadec P, et al. Involvement of a CD47-dependent pathway in platelet adhesion on inflamed vascular endothelium under flow. Blood. 101(12):4836-43. Jun. 15, 2003; Epub Feb. 27, 2003.
Lamb CA, et al. Invariant chain targets HLA class II molecules to acidic endosomes containing internalized influenza virus. Proc Natl Acad Sci U S A. 88(14):5998-6002. Jul. 15, 1991.
Lehmann JC, et al. Overlapping and selective roles of endothelial intercellular adhesion molecule-1 (ICAM-1) and ICAM-2 in lymphocyte trafficking. J Immunol. 171(5):2588-93. Sep. 1, 2003.
Lesley J, Trowbridge IS. Genetic characterization of a polymorphic murine cell-surface glycoprotein. Immunogenetics. 15(3):313-20. Mar. 1982.
Li S, et al., "Analysis of FOXP3+ regulatory T cells that display apparent viral antigen specificity during chronic hepatitis C virus infection," PLoS Pathog. Dec. 2009;5(12):e1000707. Epub Dec. 24, 2009.
Maiti A et al. TNF-alpha induction of CD44-mediated leukocyte adhesion by sulfation. Science. 282(5390):941-3. Oct. 30, 1998.
Mazor R, et al. Identification and elimination of an immunodominant T-cell epitope in recombinant immunotoxins based on Pseudomonas exotoxin A. Proc Natl Acad Sci U S A. 109(51):E3597-603. Dec. 18, 2012. Epub Dec. 3, 2012.
Mous et al., "Redirection of CMV-specific CTL towards B-CLL via CD20-targeted HLA/CMV complexes," Leukemia 20, pp. 1096-1102 (2006).
Onda M, et al. An immunotoxin with greatly reduced immunogenicity by identification and removal of B cell epitopes. Proc Natl Acad Sci U S A. 2105(32):11311-6. Aug. 12, 2008; Epub Aug. 4, 2008.
Osborn L, et al. Amino acid residues required for binding of lymphocyte function-associated antigen 3 (CD58) to its counter-receptor CD2. J Exp Med. 181(1):429-34. Jan. 1995.
O'Sullivan MK, et al., "Comparison of two methods of preparing enzyme-antibody conjugates: application of these conjugates for enzyme immunoassay," Anal Biochem. Nov. 15, 1979;100(1):100-8.
Polski JM and Janney CG. Ber-H2 (CD30) immunohistochemical staining in malignant melanoma. Mod Pathol. 12 (9):903-6. Sep. 1999.
Poon, KA, "Safety Assessment of Antibody Drug Conjugates," Presentation at Northern California Society of Toxicology. May 6, 2010.
Rajasagi M. CD44 promotes progenitor homing into the thymus and T cell maturation. J Leukoc Biol. 85(2):251-61. Feb. 2009; Epub Oct. 27, 2008.
Response to Office Action from European Patent Office dated Nov. 8, 2013, filed Apr. 14, 2014, for European Patent Application No. 12718715.1 (21 pages).
Sathish, Challenges and approaches for the development of safer immunomodulatory biologics, Nature Reviews Drug Discovery 12:306-324 (2013).
Search report from Intellectual Property Office for GB1216649 dated Jan. 17, 2013.
Stein R, et al. Epitope specificity of the anti-(B cell lymphoma) monoclonal antibody, LL2. Cancer Immunol Immunother. 37(5):293-8. Oct. 1993.
Sumida T, et al., "Regulatory T cell epitope recognized by T cells from labial salivary glands of patients with Sjögren's syndrome," Arthritis Rheum. Dec. 1997;40(12):2271-3.
Tamiolakis D et al. Distribution of somatostatin in pancreatic ductal adenocarcinoma remodels the normal pattern of the protein during foetal pancreatic development: an immunohistochemical analysis. Clin Exp Med. 5(3):106-11. 2005.
Trowbridge IS, et al. Biochemical characterization and cellular distribution of a polymorphic, murine cell-surface glycoprotein expressed on lymphoid tissues. Immunogenetics. 15(3):299-312. Mar. 1982.
Akiyama et al., "Characterization of cytomegalovirus pp65-HLA-A24 peptide-specific CTL lines from metastatic melanoma patients", Oncology Reports 22: pp. 185-191 (Mar. 3, 2009).
Non-Final Office Action in corresponding U.S. Appl. No. 14/660,137, dated Oct. 22, 2015.
Abhinandan KR and Martin AC, Protein Eng Des Sel. 23(9):689-97 (2010).
Ghanekar et al., Clin Diagn Lab Immunol 8(3):628-31 (2001).
Hochman J, et al., Biochemistry 15(12) :2706-2710 (1976).
Horne C, et al., Immunol. 129:660-664 (1982).
Mack et al., PNAS 92:7021-7025 (1995).
Masuda K, et al., FEBS Journal 273:20184-2194 (2006).
Nakanishi T et al., Protein Science 17:261-270 (2008).
Riechmann L J Mol Biol. 259:957-969 (1996).
Rothlisberger D, et al., J. Mol. Biol. 347,773-789 (2005).
Jaton, Jean-Claude, "Amino Acid Sequence of the N-Terminal 139 Residues of Light Chain Derived from a Homogeneous Rabbit Antibody," Biochem. J. (1974) 141, pp. 1-13/.
Yu, Tsan-Hua et al., "Viral hepatitis is associated with intrahepatic cholangiocarcinoma with cholangiolar differentiation and N-cadherin expression," Modern Pathology (2011) 24, pp. 810-819.

* cited by examiner

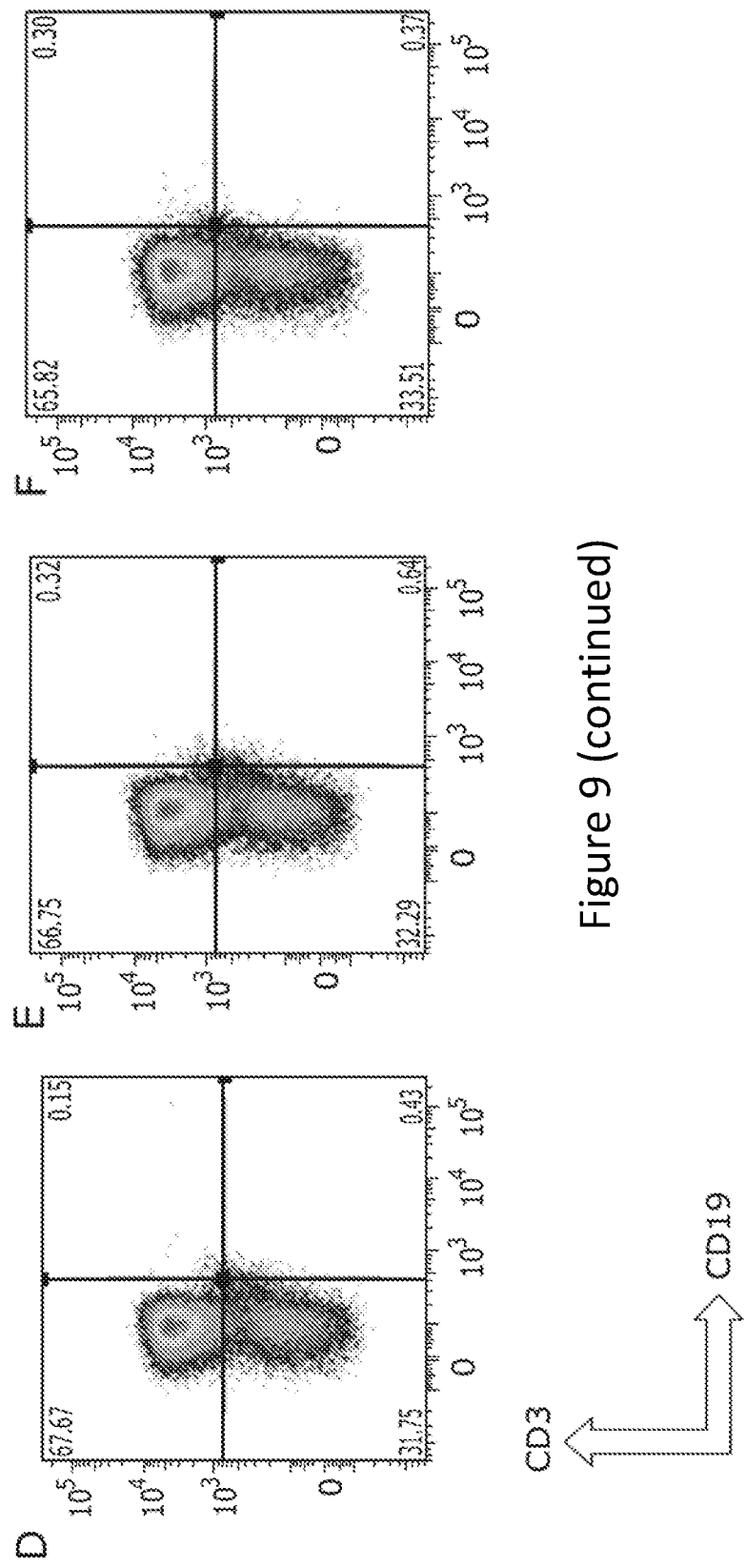

IMMUNOTHERAPEUTIC MOLECULES AND USES

RELATED APPLICATIONS

This application is the U.S. National Stage of International Application No. PCT/GB2013/050499, filed on Feb. 28, 2013, published in English, and claims priority under 35 U.S.C. § 119 or 365 to Great Britain Application No. 1203442.7, filed Feb. 28, 2012.

INCORPORATION BY REFERENCE OF MATERIAL IN ASCII TEXT FILE

This application incorporates by reference the Sequence Listing contained in the following ASCII text file being submitted concurrently herewith:
  a) File name: 44751024000_sequencelisting.txt; created Aug. 26, 2014, 17 KB in size.

The present invention relates to immunotherapeutic molecules. In particular, it relates to immunotherapeutic molecules that can be used to prevent or treat a condition characterised by the presence of unwanted cells, such as tumours or other disease causing cells.

Immunotherapeutic strategies for targeting malignant disease are an active area of translational clinical research, and have been for several decades. The current models dictate that cancer represents either a functional or constitutional immunodeficiency which can be treated with immunotherapeutic manipulation of the host. These efforts can be broadly classified into two groups. The first serves to augment or support endogenous anti-tumour immunity through measures such as vaccination, cytokine support (IL-2, IFNγ) or reducing immunosuppressant environment (ipilimumab) whilst the second seeks to restore an absolute deficiency with components of a functional immune response (passive immunotherapy with antibodies, TCR transfer, Stem Cell Transplantation and adoptive immunotherapy). These approaches are unified by the argument that a highly effective functional anti-tumour immune response is indeed possible. Although irrefutable evidence exists for an effective anti-tumour immune response in some cases, this central pillar of tumour immunology is overwhelmingly countered by the current clinical reality that despite great efforts, no effective immunotherapeutics are available for the majority of patients with cancer. Almost all cancer vaccination trials have provided negative results, with those providing positive data most frequently demonstrating a small effect. The reality is that therapeutic antibodies offer very modest clinical benefit in the area of oncology. Thus, there remains a demand for more effective immunotherapeutic agents.

Bispecific antibodies unify two antigen binding sites of different specificity into a single construct giving them the ability to bring together two discrete antigens with exquisite specificity. The first bispecific antibodies resembled natural immunoglobulin G (IgG) molecules in which the two arms were equipped with distinct binding specificities. The concept of using these bispecific antibodies to engage cytotoxic T cells for cancer cell lysis was originally shown by Staerz and colleagues in 1985 (*Nature* 1985, 314: 628). Since then, different kinds of constructs have been made and developed for the same purpose. Recent focus has been on creating antibody constructs by joining two single chain Fv regions (scFv antibody fragments) while omitting the Fc portion present in full immunoglobulins. Each scFv unit in such constructs (so-called bispecific T cell engagers or BiTE antibodies) is made up of one variable domain from each of the heavy (VH) and light (VL) antibody chains, joined with one another via a synthetic polypeptide linker. The resulting bispecific single chain antibody is therefore a species containing two VH/VL pairs of different specificity on a single polypeptide chain of approximately 55 kDa.

Promising experimental results have emerged from the use of BiTE antibodies. Kufer and colleagues have demonstrated that CD3/target antigen-bispecific antibodies of this design have an exceptionally high potency, and can engage CD8+ and CD4+ T cells for redirected lysis of cancer cells at very low effector to target ratios (Mack, PNAS (1995), 92:7021-5). The antibodies have shown potential in treating tumours (Mack, *J Immunol* (1997), 158:3965-70; Kufer, *Canc Immunol Immunother* (1997), 45:193-7; and Loffler, Blood (2000), 95: 2098-103) and also in treating non-tumour diseases (Bruhl, *J Immunol* (2001), 166:2420-6). The antibodies rely on one scFv unit being capable of activating T cells, by specifically binding to an antigen on the T cells, and the other scFv unit specifically binding to an antigen on a target cell intended for destruction. In this way, the antibodies are able to activate and redirect the immune system's cytotoxic potential for the destruction of pathological cells.

Two BITE antibodies are currently being tested in clinical trials. Blinatumomab (also known as MT103) is bispecific for CD3 on T cells and CD19 on B cells, and is being tested for the treatment of non-Hodgkin's lymphoma and acute lymphoblastic leukaemia. MT110 is bispecific for CD3 and epithelial cell adhesion molecule (EpCAM), and is being tested for the treatment of lung and gastrointestinal cancer patients.

However, a limitation of BITE antibodies and similar bispecific therapeutic antibodies is that they can activate T cells when binding to any target that expresses the targeting antigen. For instance, if the BITE or bispecific antibody was designed to target the EGF receptor, which is expressed at high levels in many epithelial cancers but also expressed at moderate levels in healthy tissues, both healthy and cancers tissue are targeted. Moreover, the agent becomes active when bound to any surface and thus non-specific binding to surfaces in a non-antigen binding manner can lead to T-cell activation and off-target effects. For these reasons, all BITE antibodies in development are given at very low concentrations.

Accordingly, although bispecific antibody constructs have great therapeutic value in redirecting the body's own immune system to achieve the eradication or neutralisation of unwanted cells, the activation of such redirection requires that it be tightly controlled so that the cytotoxic potential is recruited and applied only in the direction intended. Thus, there is a strong need for further immunotherapeutic agents that overcome limitations described above.

The present inventors have now devised a means for recruiting and activating immune cells (eg T cells) to target unwanted cells, wherein the immune cells are only activated when in the vicinity of the targeted cells. As will become apparent below, such selective activation of immune cells is based on selective unmasking of an immune cell binding region in the vicinity of unwanted target cells by an agent that resides in the vicinity of the unwanted cells. In this way, the technology is more specific for the unwanted cell (eg more cancer specific) by virtue of the immune cell binding region only being unmasked in the vicinity of the unwanted cell (eg in the presence of a cancer associated protease). This dramatically expands the therapeutic window of bispecific antibodies and so facilitates larger doses of drug to be given leading to greater target effect.

Accordingly, a first aspect of the invention provides a molecule comprising: (i) a targeting moiety capable of directly or indirectly targeting to unwanted cells, and (ii) a further moiety that has a masked immune cell binding region so as to prevent binding of the further moiety to an immune cell, wherein the masked immune cell binding region is capable of being selectively unmasked when the molecule is in the vicinity of the unwanted cells so as to allow binding of the further moiety to an immune cell. The targeting moiety functions to bring the further moiety into the vicinity of the unwanted cells, for example in the same way as one of the antigen specificities of a BiTE antibody targets the construct to a cancer cell. The selective unmasking of the immune cell binding region in the vicinity of the unwanted cells ensures that the further moiety can only engage immune cells when in the vicinity of the unwanted cells.

The individual components of the molecule are described in detail below.

Targeting Moiety

By 'targeting moiety', we include the meaning of any moiety that is capable of targeting to the unwanted cells. Preferably, the targeting moiety is capable of targeting selectively to the unwanted cells. For example, it is preferred if the targeting moiety targets unwanted cells to a greater extent than it does normal cells, and most preferably targets only unwanted cells.

It will be appreciated that binding of the targeting moiety to normal cells may be tolerated if they can be functionally replaced by other therapeutic means or if they are not essential to life. Thus, a targeting moiety that targets to a cancer cell as well as, for example, an endocrine tissue or organ is not precluded. In this case, the targeting moiety acts to redirect an immune response to both unwanted cells and to other cells that can be functionally replaced by therapeutic means. In a life-saving situation for example, the tissue or organ may be sacrificed provided its function was either not essential to life, for instance in the case of the testes, prostate or pancreas, or could be supplied by hormone replacement therapy. Such considerations would apply to the thyroid gland, parathyroids, adrenal cortex and ovaries, for example.

It follows that the targeting moiety may be a moiety that is capable of targeting selectively to unwanted cells as opposed to wanted cells, wherein the unwanted cells may include cells whose presence in a host is undesired and optionally cells whose presence in the host is desired but whose presence can be functionally replaced by therapeutic means.

It is also appreciated that selective unmasking of the immune cell binding regionconfers specificity on where the immune cell binding region is unmasked, and so binding of the targeting moiety to normal cells, in the vicinity of which the immune cell binding region is not unmasked, may also be tolerated.

Most preferably, however, the targeting moiety targets selectively to unwanted cells as opposed to any other cells.

In one embodiment, the targeting moiety is capable of directly targeting to unwanted cells. However, the targeting moiety may be one that indirectly targets to unwanted cells, for example by targeting to another moiety that is localised in the vicinity of the unwanted cells (e.g. by association with the unwanted cells), as described below.

Conveniently, the targeting moiety is a specific binding partner of an entity expressed by or associated with the unwanted cell. Typically, the expressed entity is expressed selectively on the unwanted cell. For example, the abundance of the expressed entity is typically 10 or 100 or 500 or 1000 or 5000 or 10000 higher on the unwanted cell than on other cells within the body to be treated. However, as mentioned above, the selective unmasking of the immune cell binding region in the vicinity of the unwanted cells provides additional specificity on where the immune cell binding region is unmasked and so the binding partner may bind an entity that is similarly or even underexpressed on unwanted cells relative to other cells within the body.

By "binding partner" we include the meaning of a molecule that binds to an entity expressed by a particular cell. Preferably, the binding partner binds selectively to that entity. For example, it is preferred if the binding partner has a $K_d$ value (dissociation constant) which is at least five or ten times lower (i.e. higher affinity) than for at least one other entity expressed by another cell (e.g. a normal cell type), and preferably more than 100 or 500 times lower. More preferably, the binding partner of that entity has a $K_d$ value more than 1000 or 5000 times lower than for at least one other entity expressed by another cell (e.g. normal cell type). $K_d$ values can be determined readily using methods well known in the art. However, as discussed above, it is appreciated that the binding partner may bind selectively to an entity expressed by an unwanted cell and by a normal cell provided that the normal cell may be functionally replaced or else is not essential to life. For example, in lymphoma, anti-CD20 (which targets all B cells) is very effective and kills all B cells, healthy and malignant. However, this can be tolerated as B cells are not critical for health. Further, in the case of melanoma, lymphoma, prostate cancer, thyroid, testicular or ovarian cancer, targeting healthy counterpart tissue may also be tolerated.

Typically, the binding partner is one that binds to an entity that is present or accessible to the binding partner in significantly greater concentrations in or on unwanted cells than in any normal cells of the host. Thus, the binding partner may bind to a surface molecule or antigen on the unwanted cell that is expressed in considerably higher amounts than on normal cells. Similarly, the binding partner may bind to an entity that has been secreted into the extracellular fluid by the unwanted cells to a greater extent than by normal cells. For example, the binding partner may bind to a tumour associated antigen which is expressed on the cell membrane or which has been secreted into tumour extracellular fluid.

The targeting moiety may be a polypeptide or a peptide. In a particularly preferred embodiment, the targeting moiety is an antibody that binds to an antigen expressed by the unwanted cell, for example a tumour associated antigen.

Preferred antibody targets (with examples of unwanted cell types in parentheses) include: Her2/Neu (Epithelial malignancies); CD22 (B cells, autoimmune or malignant); EpCAM (CD326) (Epithelial malignancies); EGFR (epithelial malignancies); PMSA (Prostate Carcinoma); CD30 (B cell malignancies); CD20 (B cells, autoimmune, allergic or malignant); CD33 (Myeloid malignancies); membrane IgE (Allergic B cells); IgE Receptor (CD23) (Mast cells or B cells in allergic disease), CD80 (B cells, autoimmune, allergic or malignant); CD86 (B cells, autoimmune, allergic or malignant); CD2 (T cell or NK cell lymphomas); CA125 (multiple cancers including Ovarian carcinoma); Carbonic Anhydrase IX (multiple cancers including Renal Cell Carcinoma); CD70 (B cells, autoimmune, allergic or malignant); CD74 (B cells, autoimmune, allergic or malignant); CD56 (T cell or NK cell lymphomas); CD40 (B cells, autoimmune, allergic or malignant); CD19 (B cells, autoimmune, allergic or malignant); c-met/HGFR (Gastrointestinal tract and hepatic malignancies; TRAIL-R1 (multiple malignancies including ovarian and colorectal carcinoma); DR5 (multiple malignancies including ovarian and colorectal carcinoma); PD-1 (B cells, autoimmune, allergic or malignant); PD1L (Multiple malignancies including epithelial adenocarcinoma); IGF-1R (Most malignancies including epithelial adenocarcinoma); VEGF-R2 (The vasculature associated with the majority of malignancies including epithelial adenocarcinomas; Prostate stem cell antigen (PSCA) (Prostate Adenocarcinoma); MUC1 (Epithelial malignancies); CanAg (tumors such as carcinomas of the colon and pancreas); Mesothelin (many tumours including mesothelioma and ovarian and pancreatic adenocarcinoma); P-cadherin (Epithelial malignancies, including breast adenocarcinoma); Myostatin (GDF8) (many tumours including sarcoma and ovarian and pancreatic adenocarcinoma); Cripto (TDGF1) (Epithelial malignancies including colon, breast, lung, ovarian, and pancreatic cancers); ACVRL1/ALK1 (multiple malignancies including leukaemias and lymphomas); MUC5AC (Epithelial malignancies, including breast adenocarcinoma); CEACAM (Epithelial malignancies, including breast adenocarcinoma); CD137 (B cells or T cells, autoimmune, allergic or malignant); CXCR4 (B cells or T cells, autoimmune, allergic or malignant); Neuropilin 1 (Epithelial malignancies, including lung cancer); Glypicans (multiple cancers including liver, brain and breast cancers); HER3/EGFR (Epithelial malignancies); PDGFRa (Epithelial malignancies); EphA2 (multiple cancers including neuroblastoma, melanoma, breast cancer, and small cell lung carcinoma); and CD138 (Myeloma).

Particularly preferred targeting moiety antibodies include an anti-epidermal growth factor receptor antibody such as Cetuximab, an anti-Her2 antibody, an anti-CD20 antibody such as Rituximab, an anti-CD22 antibody such as Inotuzumab, an anti-CD70 antibody, an anti-CD33 antibody such as hp67.6 or Gemtuzumab, an anti-MUC1 antibody such as GP1.4 and SM3, an anti-CD40 antibody, an anti-CD74 antibody, an anti-P-cadherin antibody, an anti-EpCAM antibody, an anti-CD138 antibody, an anti-E-cadherin antibody, an anti-CEA antibody, and an anti-FGFR3 antibody.

Yet further selective targets useful for preventing or treating various conditions characterised by the presence of unwanted cells are provided below. For all of the examples below, therapeutic antibodies are already available or can be readily prepared by the skilled person.

| Target | Unwanted cell |
|---|---|
| Activin A | Many types of carcinoma, lymphoma, sarcoma and leukaemia |
| activin A, activin B and inhibin B | Many types of carcinoma, lymphoma, sarcoma and leukaemia |
| Adenocarcinoma antigen | Many types of carcinoma, |
| AFP (alpha-fetoprotein) | Many types of carcinoma, |
| amyloid beta (Abeta) | Alzheimer's Disease |
| amyloid beta (Abeta) peptide Aβ40 | Alzheimer's Disease |
| amyloid beta (Abeta) peptide soluble monomer | Alzheimer's Disease |
| amyloid beta (Abeta) peptides Aβ42 and Aβ40 | Alzheimer's Disease |
| ANGPT2 (Ang2, angiopoietin 2) | Multiple carcinomas |
| N-glycolyl GM3 ganglioside (N-glycolylneuraminic acid (NeuGc, NGNA) GM3 gangliosides, NeuGcGM3) *Mus musculus* IgM-kappa P3 | Brain tumours |
| BSG (basigin, Ok blood group, CD147) | Many types of carcinoma, lymphoma, sarcoma and leukaemia |
| CA 72-4 (tumour associated glycoprotein 72, TAG-72, TAG, HMW mucin-like glycoprotein) | Many types of carcinoma, |
| CA9 (carbonic anhydrase IX, CAIX, MN, G250) | Many types of carcinoma, |
| carcinoma associated antigen CTAA16.88 (complex of cytokeratin polypeptides (35-40 kDa)) | Many types of carcinoma, |
| CCL11 (chemokine (C-C motif) ligand 11, chemokine CC 11, eotaxin1) | Many types of carcinoma and lymphoma/leukaemia |
| CCL2 (chemokine (C-C motif) 2, chemokine CC 2, monocyte chemoattractant protein-1, MCP-1, monocyte chemotactic and activating factor, MCAF, small inducible cytokine A2, SCYA2, HC11) | Many types of carcinoma and lymphoma/leukaemia |
| CCR4 (chemokine (C-C motif) receptor 4, chemokine CC receptor 4, CCR-4, CKR4, k5-5, CD194) | Many types of carcinoma and lymphoma/leukaemia |
| CD14 | Many types of carcinoma and lymphoma/leukaemia |
| CD15 (3-fucosyl-N-acetyl-lactosamine, Lewis x, stage-specific embryonic antigen 1, SSEA-1) | Many types of carcinoma and lymphoma/leukaemia |
| CD19 (B lymphocyte surface antigen B4, Leu-12) | Lymphoma and Acute lymphoblastic leukaemia |
| CD2 (lymphocyte function-antigen 2, LFA-2) | T-cell and NK-cell lymphoma |
| CD200 (OX-2) | T-cell and NK-cell lymphoma |
| CD22 (sialic acid binding Ig-like lectin 2, SIGLEC2, SIGLEC-2, B-lymphocyte cell adhesion molecule, BL-CAM, Leu-14 | Lymphoma and Acute lymphoblastic leukaemia |
| CD33 (sialic acid binding Ig-like lectin 3, SIGLEC3, SIGLEC-3, gpG7, p67) | Myeloid leukaemia and Stem cells |
| CD38 (ADP-ribosyl cyclase 1, cyclic ADP-ribose hydrolase 1, cADPr hydrolase 1, T10) | Myeloid leukaemia and many types of carcinoma |
| CD40 (tumor necrosis factor receptor superfamily member 5, TNFRSF5, p50) | Lymphoma and many types of carcinoma |
| CD40LG (CD40 ligand, CD40L, tumor necrosis factor ligand superfamily member 5, TNFSF5, tumor necrosis factor related activation protein, TRAP, CD154) | Lymphoma and many types of carcinoma |

-continued

| Target | Unwanted cell |
| --- | --- |
| CD44 (homing function and Indian blood group system, chondroitin sulfate proteoglycan 8, CSPG8) | Myeloid leukaemia and many types of carcinoma including cancer stem cells |
| CD5 (T1, LEU-1) | T-cell lymphoma, T-cells and B-cell lymphomas such as chronic lymphocytic leukaemia. |
| CD52 | T-cell lymphoma, T-cells and B-cell lymphomas. Autoimmune induced immune cells may also be targeted. |
| CD6 (Tp120) | T-cell lymphoma, T-cells and B-cell lymphomas such as chronic lymphocytic leukaemia. |
| CD70 (tumor necrosis factor superfamily member 7, TNFSF7, CD27LG, CD27L) | Lymphoma and many types of carcinoma |
| CD74 (major histocompatibility class II invariant chain, MH2) | Lymphoma and many types of carcinoma |
| CD80 (B7-1, CD28LG1) | Lymphoma and many types of carcinoma |
| CD86 (B7-2, CD28LG2) | Lymphoma and many types of carcinoma |
| CEA (anticarcinoembryonic antigen) | Many types of carcinoma, |
| CEACAM3 (carcinoembryonic antigen-related cell adhesion molecule 3, CGM1, CD66d) | Many types of carcinoma, |
| CEACAM5 (carcinoembryonic antigen-related cell adhesion molecule 5, CEA, CD66e) | Many types of carcinoma, |
| CEACAM8 (carcinoembryonic antigen-related cell adhesion molecule 8, NCA-95, nonspecific cross- reacting antigen 95 kDa, granulocyte cell antigen, CGM6, CD66b) | Many types of carcinoma, |
| ClfA (Clumping factor A) | Many types of carcinoma, |
| complement C3b, C4b | Many types of unwanted cells. |
| CSF2 (colony stimulating factor 2 (granulocyte-macrophage), granulocyte-macrophage colony stimulating factor, GM-CSF) | Myeloid diseases |
| CSF2RA (colony-stimulating factor 2 (granulocyte-macrophage) receptor alpha subunit, GM-CSF-R-alpha, CD116) | Myeloid diseases |
| CSPG4 (chondroitin sulfate proteoglycan 4, high molecular weight-melanoma-associated antigen, HMW-MAA) | Many types of carcinoma, lymphoma, sarcoma and leukaemia |
| CTLA4 (cytotoxic T lymphocyte-associated antigen 4, CD152) | Regulatory T-cells and unwanted immune cells. |
| ED-B (fibronectin extra domain B) | Many types of carcinoma, |
| EGFR (epidermal growth factor receptor, receptor tyrosine-protein kinase erbB-1, ERBB1, HER1, HER-1, ERBB) | Many types of carcinoma, lymphoma, sarcoma and leukaemia |
| EPCAM (epithelial cell adhesion molecule, tumor-associated calcium signal transducer 1, TACSTD1, gastrointestinal tumor-associated protein 2, GA733-2, epithelial glycoprotein 2, EGP-2, epithelial cell adhesion molecule, Ep-CAM, KSA, KS1/4 antigen, M4S, tumor antigen 17-1A, EpCAM, CD326) | Many types of carcinoma, lymphoma, sarcoma and leukaemia |
| ERBB2 (epidermal growth factor receptor 2, receptor tyrosine-protein kinase erbB-2, EGFR2, HER2, HER-2, p185c-erbB2, NEU, CD340 | Many types of carcinoma, lymphoma, sarcoma and leukaemia |
| ERBB3 (receptor tyrosine-protein kinase erbB-3, HER3) | Many types of carcinoma, lymphoma, sarcoma and leukaemia |
| FAP (fibroblast activation protein, alpha) | Many types of carcinoma, lymphoma, sarcoma and leukaemia. |
| FCER2 (immunoglobulin E Fc receptor low affinity II, Fc epsilon RII, CD23) | Many types of carcinoma, lymphoma, sarcoma and leukaemia in B-cells. |
| FCGR1 (immunoglobulin G Fc receptor high affinity I, Fc gamma RI, CD64, encoded by human FCGR1A, FCGR1B, FCGR1C) | Many types of carcinoma, lymphoma, sarcoma and leukaemia. |
| fibrin II beta chain (NH2 terminus) | Many types of carcinoma, lymphoma, sarcoma and leukaemia. |
| FLT1 (fms-related tyrosine kinase 1, vascular endothelial growth factor receptor 1, VEGFR-1, VEGFR, FLT, FRT, vascular permeability factor receptor) | Many types of carcinoma, sarcoma, lymphoma, sarcoma and leukaemia. In particular tumour blood vessels. |
| FOLH1 (folate hydrolase, prostate specific membrane antigen, PSMA) | Many types of carcinoma, lymphoma, sarcoma and leukaemia in particular prostate carcinoma and unwanted prostate tissue. |
| FOLR1 (folate receptor 1, folate receptor FR alpha, FR-alpha, adult folate-binding protein, FBP, ovarian tumor-associated antigen MOv18) | Many types of carcinoma, lymphoma, sarcoma and leukaemia |
| GD2 ganglioside | Brain tumours and unwanted neuronal tissue. |
| GD3 ganglioside | Brain tumours and unwanted neuronal tissue. |

-continued

| Target | Unwanted cell |
|---|---|
| GLP1R (glucagon-like peptide 1 receptor) | Many types of carcinoma, lymphoma, sarcoma and leukaemia |
| GPNMB (glycoprotein transmembrane NMB, hematopoeitic growth factor inducible neurokinin-1 type, HGFIN) | Many types of carcinoma, lymphoma, sarcoma and leukaemia |
| hapten NP-cap (4-hydroxy-3-nitrophenacetyl caproic acid) | Many types of carcinoma, lymphoma, sarcoma and leukaemia |
| HAVCR1 (hepatitis A virus cellular receptor 1, T-cell immunoglobulin and mucin domain-containing protein 1, TIM1, KIM-1) | Hepatitis A infected cells. |
| HBV (hepatitis B virus) | HBV infected cells |
| HCMV (human cytomegalovirus) gB glycoprotein | CMV infected cells. |
| HCV (hepatitis C virus) | HCV infected cells |
| heat shock protein 90 homolog | Many types of carcinoma, lymphoma, sarcoma and leukaemia |
| HGF (hepatocyte growth factor, scatter factor, SF, hepatopoeitin A) | Hepatoma and hepatocellular carcinoma. Also unwanted hepatic tissue. |
| HIV-1 (human immunodeficiency virus) | HIV infected cells |
| HLA-DR10 (DRB1*1001) | Autologous or Allogeneic MHC Class-II expressing cells including tumour cells |
| HLA-DRB (HLA-DR beta) | Autologous or Allogeneic MHC Class-II expressing cells including tumour cells |
| HSV (herpes simplex virus) | HSV infected cells |
| ICAM1 (intercellular adhesion molecule 1, ICAM-1, CD54) | Many types of carcinoma, lymphoma, sarcoma and leukaemia |
| ICAM3 (intercellular adhesion molecule 3, ICAM-3, CD50) | Many types of carcinoma, lymphoma, sarcoma and leukaemia |
| Membrane Immunoglobulin IgE | IgE secreting B-cells and Plasma cells (cuasing allergic disease). |
| IgE Fc | IgE secreting B-cells and Plasma cells (cuasing allergic disease). |
| IGF1R (insulin-like growth factor 1 receptor, IGF1-R, IGF-1R, CD221) | Most types of carcinoma, lymphoma, sarcoma and leukaemia |
| IGHE connecting region (CO) M1 prime (in alternatively spliced heavy chain of membrane IgE on B cells | IgE secreting cells such as B-cells and plasma cells. Particularly unwanted in allergic disease. |
| IL2RA (interleukin-2 receptor, alpha subunit, IL-2RA, TAC, CD25) | B-cells and T-cells in either malignant or autoimmune disease. |
| IL2RB (interleukin-2 receptor beta subunit, IL-2RB, p70, CD122) | B-cells and T-cells in either malignant or autoimmune disease. |
| IL5RA (interleukin 5 receptor alpha subunit, CD125) | B-cells and T-cells in either malignant or autoimmune disease. |
| IL6R (interleukin 6 receptor, IL-6R, CD126) | B-cells and T-cells in either malignant or autoimmune disease. |
| ITGA2 {integrin alpha 2, GPIa, subunit of the alpha2beta1 integrin (VLA-2, collagen receptor), CD49b) | Many types of carcinoma, lymphoma, leukaemias. |
| ITGA2B_ITGB3 (integrin alpha2b_beta3, integrin aIIbβ3, GPIIbIIIa, fibrinogen receptor, CD41_CD61) | Many types of carcinoma, lymphoma, leukaemias. |
| ITGA4 (integrin alpha 4 subunit, CD49d) | Many types of carcinoma, lymphoma, leukaemias. |
| ITGA4_ITGB7 (integrin alpha4_beta7, integrin α4β7, lymphocyte Peyer's patch adhesion molecule 1, LPAM-1) | Many types of carcinoma, lymphoma, leukaemias. |
| ITGA5 (integrin alpha 5 subunit, CD49e) | Many types of carcinoma, lymphoma, leukaemias. |
| ITGAE_ITGB7 (integrin alphaE_beta7, integrin αEβ7, human mucosal lymphocyte antigen 1, HML-1) | Many types of carcinoma, lymphoma, leukaemias. |
| ITGAL (integrin alpha L subunit, lymphocyte function associated antigen 1, CD11a) | Many types of carcinoma, lymphoma, leukaemias. |
| ITGAV_ITGB3 (integrin alphaV_beta3, integrin aVβ3, CD51_GPIIIa, vitronectin receptor, VNR, CD51_CD61) | Many types of carcinoma, lymphoma, leukaemias. |
| ITGB1 (integrin beta1 subunit, GPIIa, CD29) | Many types of carcinoma, lymphoma, leukaemias. |
| ITGB2 (integrin beta2 subunit, LFA-1, MAC-1, CD18) | Many types of carcinoma, lymphoma, leukaemias. |
| KDR (kinase insert domain receptor, vascular endothelial growth factor receptor 2, VEGFR2, VEGF-R2, FLK1, CD309) | Many types of carcinoma, lymphoma, leukaemias. |
| LTA (lymphotoxin alpha, TNF superfamily member 1, TNFSF1, LT) | Many types of carcinoma, lymphoma, leukaemias. |
| LTB (lymphotoxin beta, TNF superfamily member 3, TNFSF3, p33) | Many types of carcinoma, lymphoma, leukaemias. |

-continued

| Target | Unwanted cell |
|---|---|
| MET (met proto-oncogene, hepatocyte growth factor HGF receptor, HGFR, scatter factor SF receptor, HGF/SF receptor, tyrosine protein kinase c-met, papillary renal cell carcinoma 2, RCCP2) | Many types of carcinoma, lymphoma, leukaemias. |
| MS4A1 (membrane-spanning 4-domains subfamily A member 1, CD20) | Many types of carcinoma, lymphoma, leukaemias. |
| MSLN (mesothelin, pre-pro-megakaryocyte-potentiating factor, megakaryocyte potentiating factor, MPF, CAK1) | Many types of carcinoma, lymphoma, leukaemias. |
| MST1R (macrophage stimulating 1 receptor, macrophage stimulating protein receptor, MSP receptor, c-met-related tyrosine kinase, protein-tyrosine kinase 8, PTK8, RON, p185-Ron, CD136) | Many types of carcinoma, lymphoma, leukaemias. |
| MSTN (myostatin, growth differentiation factor 8, GDF8) | Many types of carcinoma, lymphoma, leukaemias. |
| MUC1 (mucin 1, polymorphic epithelial mucin, PEM, episialin, CD227) | Many types of carcinoma, lymphoma, leukaemias. |
| MUC1 sialylated carbohydrate, tumour-associated (CA242, cancer antigen 242) | Many types of carcinoma, lymphoma, leukaemias. |
| MUC16 (mucin 16, MUC-16, cancer antigen 125, CA125) | Many types of carcinoma, lymphoma, leukaemias. |
| MUC5AC (mucin 5AC, mucin 5 subtypes A and C tracheobronchial/gastric) | Many types of carcinoma, lymphoma, leukaemias. |
| N-glycolyl GM3 ganglioside (N-glycolylneuraminic acid (NeuGc, NGNA) GM3 ganglioside, NeuGcGM3) | Brain tumours and unwanted neural tissue. |
| NCA-90 (nonspecific cross-reacting antigens 90 kDa glycoproteins, granulocyte cell antigen) | Many types of carcinoma, lymphoma, sarcoma and leukaemia |
| NCAM1 (neural cell adhesion molecule 1, NCAM-1, NCAM, CD56) | Brain tumours and unwanted neural tissue also many types of carcinoma and lymphoma. |
| Nectin-4 | Many types of carcinoma, lymphoma, sarcoma and leukaemia |
| NGF (nerve growth factor, nerve growth factor beta polypeptide, NGFB, beta-NGF) | Many types of carcinoma, lymphoma, sarcoma and leukaemia |
| NIP-cap (3-iodo-4-hydroxy-5-nitrophenyl-acetyl caproic acid) | Many types of carcinoma, lymphoma, sarcoma and leukaemia |
| NRP1 (neuropilin 1, NRP, vascular endothelial cell growth factor 165 receptor, VEGF165 receptor, VEGF165R, CD304) | Many types of carcinoma, lymphoma, sarcoma and leukaemia |
| PDGFRA (platelet-derived growth factor receptor alpha subunit, PDGFR2, CD140a) | Many types of carcinoma, lymphoma, sarcoma and leukaemia |
| phosphatidylserine | Many types of carcinoma, lymphoma, sarcoma and leukaemia particularly apoptotic cells. |
| PSCA (prostate stem cell antigen) | Many types of carcinoma and leukaemia. |
| RSV (human respiratory syncytial virus, glycoprotein F) | RSV infected cells |
| RTN4 (reticulon 4, neurite outgrowth inhibitor, NOGO) | Many types of carcinoma, lymphoma, sarcoma and leukaemia |
| SDC1 (syndecan-1, CD138) | Unwanted plasma cells found in plasma cell dyscrasias, particularly Myeloma, Amyloidosis and MGUS. |
| SELE (E-selectin, CD62E) | Many types of carcinoma and lymphoma. |
| SELL (L-selectin, CD62) | Many types of carcinoma and lymphoma. |
| SELP (P-selectin, CD62) | Many types of carcinoma and lymphoma. |
| SFRP1 (selected frizzled-related protein 1, fusion regulatory protein 1, FRP-1) | Many types of carcinoma and lymphoma. |
| SLAMF7 (SLAM family member 7, CD2 subset 1, CS1, CD2-like receptor-activating cytotoxic cells, CRACC, 19A24, CD319) | Many types of unwanted cells including tumour cells and those involved in autoimmune disease. |
| SLC3A2 (solute carrier family 3 (activators of dibasic and neutral amino acid transport) member 2, 4F2 antigen heavy chain, 4F2HC, CD98 heavy chain, CD98hc, CD98) | Many types of unwanted cells including tumour cells and those involved in inflammatory disease. |
| SOST (sclerostin) | Bone disease including oesteosarcoma and osteoporosis. |
| *Staphylococcus epidermidis* lipoteichoic acid | *Staphylococcus* infected tissue. |
| T cell receptor (TR) TR alpha_beta | T-cell lymphoma or autoimmune-causing T-cells. |
| TGFB1 (transforming growth factor beta1, TGF beta) | Many types of unwanted cells including tumour cells and those involved in fibrotic disease. |
| TGFB2 (transforming growth factor beta 2) | Many types of unwanted cells including tumour cells and those involved in fibrotic disease. |
| TNF (tumor necrosis factor (TNF) superfamily member 2, TNFSF2, TNF-alpha, TNFA) | Many types of unwanted cells including tumour cells and those involved in inflammatory disease. |

-continued

| Target | Unwanted cell |
|---|---|
| TNFRSF10A (tumor necrosis factor receptor (TNFR) superfamily member 10A, death receptor 4, DR4, TNF-related apoptosis-inducing ligand receptor 1, TRAILR1, TRAIL-R1, TR-1, CD261) | Many types of unwanted cells including tumour cells and those involved in inflammatory disease. |
| TNFRSF10B (tumor necrosis factor receptor (TNFR) superfamily member 10B, death receptor 5, DR5, TNF-related apoptosis-inducing ligand receptor 2, TRAILR2, TRAIL-R2, TR-2, CD262) | Many types of unwanted cells including tumour cells and those involved in inflammatory disease. |
| TNFRSF12A (tumor necrosis factor receptor (TNFR) superfamily member 12A, fibroblast growth factor (FGF)-inducible 14 kDa protein, Fn14, TNF-like weak inducer of apoptosis (Tweak) receptor, Tweak receptor, TweakR, CD266 | Many types of unwanted cells including tumour cells and those involved in inflammatory disease. |
| TNFRSF8 (tumor necrosis factor receptor (TNFR) superfamily member 8, CD30) | Many types of unwanted cells including tumour cells (in particular lymphoma) and those involved in inflammatory disease. |
| TNFRSF9 (tumor necrosis factor receptor (TNFR) superfamily member 9, 4-1BB, T cell antigen ILA, CD 137 | Many types of unwanted cells including tumour cells and those involved in inflammatory and autoimmune disease. |
| TNFSF11 (tumor necrosis factor (TNF) superfamily member 11, osteoclast differentiation factor, ODF, OPGL, RANKL, TRANCE, CD254) | Many types of unwanted cells including tumour cells and those involved in inflammatory and autoimmune disease. |
| TNFSF13 (tumor necrosis factor (TNF) superfamily member 13, a proliferation-including ligand, APRIL, CD256 | Many types of unwanted cells including tumour cells and those involved in inflammatory and autoimmune disease. |
| TNFSF13B (tumor necrosis factor (TNF) superfamily member 13B, B cell activating factor, BAFF, TALL1, BLyS, B lymphocyte activator, CD257) | Many types of unwanted cells including tumour cells and those involved in inflammatory and autoimmune disease. |
| TNFSF14 (tumor necrosis factor (TNF) superfamily member 14, LIGHT, HVEM-L, CD258) | Many types of unwanted cells including tumour cells and those involved in inflammatory and autoimmune disease. |
| TNFSF4 (tumor necrosis factor (TNF) superfamily member 4, OX40 ligand, OX-40L, TAX transcriptionally-activated glycoprotein 1, TXGP1, gp34, CD252) | Many types of unwanted cells including tumour cells and those involved in inflammatory and autoimmune disease. |
| TPBG (trophoblast glycoprotein, 5T4) | Multiple carcinomas. |
| TYRP1 (tyrosinase-related protein 1,5,6-dihydroxyindole-2-carboxylic acid oxidase, DHICA oxidase, TRP1, melanoma antigen gp75) | Multiple carcinomas. |
| VAP-1 (vascular adhesion protein) | Multiple carcinomas and hepatomas. |
| VEGFA (vascular endothelial growth factor A, VEGF-A, VEGF) | Multiple carcinomas and hepatomas. |
| VIM (vimentin) | Multiple carcinomas and hepatomas. |

Examples of tumour-associated, immune cell-associated and infection reagent-related antigens which may be targeted by the targeting moiety are given in Table 1.

TABLE 1

Cell surface antigens for targeting

| Antigen | Antibody | Existing uses |
|---|---|---|
| a) Tumour Associated Antigens | | |
| Carcino-embryonic Antigen | C46 (Amersham) 85A12 (Unipath) | Imaging and therapy of colon/rectum tumours. |
| Placental Alkaline Phosphatase | H17E2 (ICRF, Travers & Bodmer) | Imaging and therapy of testicular and ovarian cancers. |
| Pan Carcinoma | NR-LU-10 (NeoRx Corporation) | Imaging and therapy of various carcinomas including small cell lung cancer. |
| Polymorphic Epithelial Mucin (Human milk fat globule) | HMFG1 (Taylor-Papadimitriou, ICRF) | Imaging and therapy of ovarian cancer and pleural effusions. |
| β-human Chorionic Gonadotropin | W14 | Targeting of carboxypeptidase to human xenograft choriocarcinoma in nude mice (Searle et al (1981) *Br. J. Cancer* 44, 137-144). |
| A carbohydrate on Human Carcinomas | L6 (IgG2a)[1] | Targeting of alkaline phosphatase (Senter et al (1988) *PNAS USA* 85, 4842-4846. |
| CD20 Antigen on B Lymphoma (normal and neoplastic) | 1F5 (IgG2a)[2] | Targeting of alkaline phosphatase (Senter et al (1988) *PNAS USA* 85, 4842-4846. |

Other antigens include alphafoetoprotein, Ca-125 and prostate specific antigen.

b) Immune Cell Antigens

TABLE 1-continued

Cell surface antigens for targeting

| Antigen | Antibody | Existing uses |
|---|---|---|
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodmer and Knowles, ICRF; licensed to Xoma Corp., USA) | Immunotoxin treatment of acute graft versus host disease, rheumatoid arthritis. |
| c) Infectious Agent-Related Antigens | | |
| Mumps virus-related | Anti-mumps polyclonal antibody | Antibody conjugated to diphtheria toxin for treatment of mumps. |
| Hepatitis B Surface Antigen | Anti HBs Ag | Immunotoxin against hepatoma. |

[1]Hellström et al (1986) Cancer Res. 46, 3917-3923
[2]Clarke et al (1985) Proc. Natl. Acad. Sci. USA 82, 1766-1770

As used herein, the term "antibody" includes but is not limited to polyclonal, monoclonal, chimeric, single chain, Fab fragments, fragments produced by a Fab expression library and bispecific antibodies. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. A targeting moiety comprising only part of an antibody may be advantageous by virtue of optimising the rate of clearance from the blood and may be less likely to undergo non-specific binding due to the Fc part. Also included are domain antibodies (dAbs), diabodies, camelid antibodies and engineered camelid antibodies. Furthermore, for administration to humans, the antibodies and fragments thereof may be humanised antibodies, which are now well known in the art (Janeway et al (2001) *Immunobiology.*, 5th ed., Garland Publishing); An et al (2009) *Therapeutic Monoclonal Antibodies*: From Bench to Clinic, ISBN: 978-0-470-11791-0).

Also included are asymmetric IgG-like antibodies (eg triomab/quadroma, Trion Pharma/Fresenius Biotech; knobs-into-holes, Genentech; Cross MAbs, Roche; electrostatically matched antibodies, AMGEN; LUZ-Y, Genentech; strand exchange engineered domain (SEED) body, EMD Serono; biolonic, Merus; and Fab-exchanged antibodies, Genmab), symmetric IgG-like antibodies (eg dual targeting (DT)-Ig, GSK/Domantis; two-in-one antibody, Genentech; cross-linked MAbs, karmanos cancer center; mAb[2], F-star; and Coy X-body, Coy X/Pfizer), IgG fusions (eg dual variable domain (DVD)-Ig, Abbott; IgG-like bispecific antibodies, Eli Lilly; Ts2Ab, Medimmune/AZ; BsAb, ZymoGenetics; HERCULES, Biogen Idec; TvAb, Roche) Fc fusions (eg ScFv/Fc fusions, Academic Institution; SCORPION, Emergent BioSolutions/Trubion, ZymoGenetics/BMS; dual affinity retargeting technology (Fc-DART), MacroGenics; dual (ScFv)$_2$-Fab, National Research Center for Antibody Medicine) Fab fusions (eg F(ab)$_2$, Medarex/AMGEN; dual-action or Bis-Fab, Genentech; Dock-and-Lock (DNL), Immuno-Medics; bivalent bispecific, Biotechnol; and Fab-Fv, UCB-Celltech), ScFv- and diabody-based antibodies (eg bispecific T cell engagers (BiTEs), Micromet; tandem diabodies (Tandab), Affimed; DARTs, MacroGenies; Single-chain diabody, Academic; TCR-like antibodies, AIT, Receptor Logics; human serum albumin ScFv fusion, Merrimack; and COMBODIES, Epigen Biotech), IgG/non-IgG fusions (eg immunocytokins, EMDSerono, Philogen, ImmunGene, ImmunoMedics; superantigen fusion protein, Active Biotech; and immune mobilising mTCR Against Cancer, ImmTAC) and oligoclonal antibodies (eg Symphogen and Merus).

The antibody may possess any of the antibody-like scaffolds described by Carter (2006) "Potent antibody therapeutics by design", *Nat Rev Immunol*. 6(5):343-57, and Carter (2011) "Introduction to current and future protein therapeutics: a protein engineering perspective", *Exp Cell Res*. 317(9): 1261-9. incorporated herein by reference, together with the specificity determining regions described herein. Thus, the term "antibody" also includes affibodies and non-immunoglobulin based frameworks.

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli* or yeast, thus allowing convenient production in the laboratory and economical production on a commercial scale.

The antibody may be of any of the IgG, IgE, IgA, IgM and IgD classes and may be derived from any species. If the antibody is an IgG, it may be any of IgG1, IgG2, IgG3 or IgG4. It is preferred, however, that when the agent is for administration to a particular host, that the antibody, or at least the constant regions thereof, are derived from that host. For example, when the agent is to be administered to a human, the antibody is preferably a human antibody or a humanized antibody, and so on.

Suitable antibodies that bind to particular antigens expressed by unwanted cells can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol*. 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res*. 29: E27). Further, antibodies and antibody fragments suitable for use in the present invention are described, for example, in the following publications: "*Monoclonal Hybridoma Antibodies: Techniques and Application*", Hurrell (CRC Press, 1982); "*Monoclonal Antibodies: A Manual of Techniques*", H. Zola, CRC Press, 1987, ISBN: 0-84936-476-0; "*Antibodies: A Laboratory Manual*" 1$^{st}$ Edition, Harlow & Lane, Eds, Cold Spring Harbor Laboratory Press, New York, 1988. ISBN 0-87969-314-2; "*Using Antibodies: A Laboratory Manual*" 2$^{nd}$ Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., 1$^{st}$ Edition—Wiley-VCH, Weinheim, 2007. ISBN: 3-527-31453-9.

It is especially preferred if the targeting moiety is a single chain antibody such as a scFv antibody that comprises a heavy chain variable domain and a light chain variable domain, which domains are joined together by a flexible peptide linker. Preferably, the single chain antibody binds to an entity expressed by the unwanted cell, including any of those mentioned above. However, it will also be understood that the targeting moiety may comprise only one antibody variable domain, such as a heavy chain variable domain or a light chain variable domain, and such a domain may bind to an entity expressed by the unwanted cell.

It will be appreciated that the targeting moiety may also be any compound or part thereof that specifically binds, in a non-immune sense, to an entity expressed by unwanted cells or otherwise becomes associated with the unwanted cells. Thus, the specific binding partner may be any of a hormone, a growth factor, a cytokine, or a receptor ligand (e.g. agonist or antagonist).

For example, cytokines have previously been used to target toxins to invading bacterial. Using genetic engineering, recombinant proteins have been produced which contain for example IL-2 and a binding domain-deleted *Pseudomonas* exotoxin protein (Lorderboum-Galski et al, 1988 (62)). This immunotoxin was effective in experimental animal models (Kozak et al, 1990 (63)). Fusion proteins have also been produced with IL-4, IL-6, alpha-MSH, EGF and TNF-alpha (reviewed in Waldmann 1992 (35)), all of which are appropriate for use as targeting moieties in the present invention.

Particularly useful targeting moieties include cytokines such as IL-2, EGF, VEGF, Flt3L, HGF, IGF, IL-6, or IL-4. IL-2 and IL-4 can target to adult T cell leukaemia/lymphoma cells which express the high affinity IL-2 receptor whereas normal resting T-cells do not, or to T-cells expressing the IL-4 receptor. It has previously been shown that the monoclonal antibody MR6, which binds to the human IL-4 receptor, can inhibit the IL-4 induced proliferation of cloned helper T cells and the production of IgE by polyclonal B cells (Larche et al, 1988 (36)). Such targeting moieties may be used to eliminate a lymphoid cell subpopulation in autoimmune disease or allergy.

Insulin like growth factors (IGF-1 and IGF-11) are preferentially taken up by malignant cells and so may be used to target tumour cells. Similarly EGF can be used to target malignant cells which upregulate the EGF receptor. Also, tumour associated blood vessels overexpress VEGF receptor and so can be targeted by the family of VEGF growth factors.

Flt3 receptor is overexpressed in leukaemias and may be a therapeutic target for acute and chronic leukaemias and myeloproliferative disorders.

Myeloma cells express IL-6 receptor and also secrete IL-6 which acts in an autocrine fashion to stimulate cell proliferation. Thus IL-6 may be used as a targeting moiety for myeloma.

In another example, the targeting moiety is melanoma stimulating hormone (MSH) which binds to the MSH receptor which is expressed in high numbers in melanoma cells.

It is appreciated that a person skilled in the art can readily select suitable binding partners for any given unwanted cell, for example by identifying surface antigens or molecules specific for that unwanted cell and finding a binding partner for that antigen or molecule. Considerable research has been carried out on antibodies and fragments thereof to tumour-associated antigens, immune cell antigens and infectious agents, as described above. Thus, conveniently, selecting an appropriate targeting moiety for a given cell type typically involves searching the literature. Alternatively, an unwanted cell is taken from a patient (e.g. by biopsy), and antibodies directed against the cell prepared. Such 'tailor-made' antibodies are already known. It has been demonstrated that antibodies confer binding to tumour cells not only from the patient they have been obtained from but also for a large number of other patients. Thus, a plurality of such antibodies has become commercially available. Other methods of identifying suitable binding partners for a given unwanted cell include genetic approaches (eg microarray), proteomic approaches (eg differential Mass spectrometry), immunological approaches (eg immunising animals with tumour cells and identifying antibody-secreting clones which specifically target malignant cells) and in silico approaches wherein targets are identified using a systems biology approach.

Further selective targets and suitable binding partners are shown in Table 2.

TABLE 2

Binding partners for tumour-selective targets and tumour-associated antigens

| Target | Binding Partner | Disease |
|---|---|---|
| Truncated EGFR | anti-EGFR mAb | Gliomas |
| Idiotypes | anti-id mAbs | B-cell lymphomas |
| EGFR (c-erbB1) | EGF, TGFα anti-EGFR mAb | Breast cancer |
| c-erbB2 | mAbs | Breast cancer |
| IL-2 receptor | IL-2 anti-Tac mAb | Lymphomas and leukaemias |
| IL-4 receptor | IL-4 | Lymphomas and leukaemias |
| IL-6 receptor | IL-6 | Lymphomas and leukaemias |
| MSH (melanocyte-stimulating hormone) receptor | α-MSH | Melanomas |
| Transferrin receptor (TR) | Transferrin anti-TR mAb | Gliomas |
| gp95/gp97 | mAbs | Melanomas |
| p-glycoprotein cells | mAbs | drug-resistant |
| cluster-1 antigen (N-CAM) | mAbs | Small cell lung carcinomas |
| cluster-w4 | mAbs | Small cell lung carcinomas |
| cluster-5A | mAbs | Small cell lung carcinomas |
| cluster-6 (LeY) | mAbs | Small cell lung carcinomas |
| PLAP (placental alkaline phosphatase) | mAbs | Some seminomas Some ovarian; some non small cell lung cancer |
| CA-125 | mAbs | Lung, ovarian carcinoma |
| ESA (epithelial specific antigen) | mAbs | |
| CD 19, 22, 37 | mAbs | B-cell lymphomas |
| 250 kDa | mAbs | Melanoma |
| proteoglycan p55 | mAbs | Breast cancer |
| TCR-IgH fusion | mAbs | Childhood T-cell leukaemia |
| Blood gp A antigen (in B or O individuals) | mAbs | Gastric and colon tumours |
| Mucin protein core | mAbs | Breast cancer |

Further targets useful in preventing or treating various cancers are provided below.

| Target | Cancer |
|---|---|
| EpCam | Bladder |
| PMSA | Prostate |
| EGFR | Breast |
| | Lung |
| | Glioblastoma |
| | Colon |
| CD20 | Lymphoma |
| CD22 | Lymphoma |

| Target | Cancer |
|---|---|
| CD52 | Lymphoma<br>Leukaemia |

As an alternative to the targeting moiety being a specific binding partner, the targeting moiety may be a non-specific molecule that is capable, following administration to a subject, of accumulating in the vicinity of the unwanted cells. For example, it is known that macromolecules accumulate non-specifically in tumours. Macromolecules known to accumulate in tumours non-specifically include albumin, immunoglobulins, transferrin, liposomes, nanoparticles (eg colloidal nanoparticles) and biodegradable polymers including dextrans, polyethylene glycol, polylysine and hydroxypropylmethylacrylamide. Macromolecules accumulate in human xenografted tumours in nude mice up to about 2.0% of administered dose per gram of tumour. Macromolecules such as polyethylene glycol and dextrans have been found to modify the clearance rate of substances to which they are attached and modify their concentration in tumours (Melton et al, 1987; Eno-Ammoquaye et al, 1996). In exceptional tumours, a non-specific macromolecule may accumulate in greater concentration than an antibody directed at the secreted antigen (Searle et al, 1981).

The discovery that such macromolecules accumulate in tumours has been called the Enhanced Permeability and Retention (EPR) effect, and has been attributed to the leakiness of tumour capillaries and deficient lymphatic drainage (Matsumura & Macda, 1986).

Thus, when the unwanted cells are tumour cells, the targeting moiety may be any of these macromolecules which accumulate in tumours. Preferably, the macromolecule used in the invention is hydrophilic and is characterised by being soluble in body fluids and in conventional fluids for parenteral administration. Suitably, the macromolecule is biodegradable so that systemic accumulation during repeated administration is avoided. Clearly, however, it must not be degraded so fast as to fail to accumulate at the site of the unwanted cells (e.g. tumour). Preferably, the molecular weight and size of the agent comprising such a macromolecule targeting moiety exceeds that of the renal threshold for urinary excretion (MW 60 000), as this helps the blood concentration to be sufficient to provide an effective blood:tumour concentration gradient. A molecular weight of up to at least 800 000 is generally suitable, for example up to 160 000. The macromolecule is preferably one which is not readily captured by the reticuloendothelial system. The molecular weights given exclude any water of hydration.

Macromolecules that are available as sub-units and are not biodegradable may be linked by biodegradable linking units so that the non-biodegradable components are filtered through the kidneys and excreted in the urine.

Alternatively, it is preferred if the polymer used to make the macromolecule is not biodegradable such that the molecular weight of any non-biodegradable portion of the conjugate should be less than the renal threshold (circa 70000) so that after degradation of the biodegradable portion the residual non-biodegradeable portion is excreted through the kidneys.

Conveniently, the macromolecule may be any of a dextran; a polyamino acid; a nanoparticle (eg colloidal nanoparticle), or a non-tumour-specific protein such as an immunoglobulin, an albumin or a transferrin. Suitably, it may be a copolymer of styrene and maleic anhydride, or may be polyaspartic acid, poly-L-lysine, polyethyleneimine or polyethylene glycol.

It is appreciated that such macromolecules are used in melanocyte-directed enzyme prodrug therapy (MDEPT), as described in WO 1998/024478.

In addition to directly targeting an unwanted cell, the targeting moiety may be one that is capable of indirectly targeting to unwanted cells by being capable of binding to a moiety that is capable of targeting to unwanted cells. For example, a moiety that is capable of directly targeting to an unwanted cell (including any of those described above) may comprise a first binding partner. A targeting moiety that comprises a second binding partner, capable of binding to the first binding partner, then has the ability to indirectly target the unwanted cells by virtue of it being able to bind to the first binding partner. In this case, the targeting moiety does not bind to an entity expressed by or associated with the unwanted cell directly, however it does so indirectly by binding to a moiety that does bind to an entity expressed by or associated with the unwanted cell. It will be understood that the molecule of the invention may comprise targeting moieties that indirectly target unwanted cells in this way, as well as those targeting moieties that target unwanted cells directly. By the first and second binding partners, we include the meaning of any two moieties which bind to each other selectively. Most preferably, the first and second binding partners only bind to each other and not to any other moieties. Non-covalent binding such as between biotin/avidin or streptavidin, or immunological bindings are preferred. Thus, the first binding partner may be biotin and the second binding partner may be avidin, and vice versa. Alternatively, the first binding partner may be an antigen and the second binding partner may be an antibody specific for that antigen, and vice versa. However, any pair of first and second binding partners that selectively bind to each other may be used, and suitable pairs will be known to the skilled person.

Unwanted Cell

The unwanted cell may be any cell whose presence in a host is undesired. Thus, the cell may be a tumour cell (benign or malignant), a cell from a tumour microenvironment such as tumour fibroblasts or tumour blood vessels, a virally infected cell, a cell introduced as part of gene therapy, or a normal cell which one wishes to destroy for a particular reason. For instance, it may be desirable to eliminate a subpopulation of immune cells such as T lymphocytes in autoimmune disease or such as B lymphocytes in allergic disease. Preferably, the unwanted cell is one whose presence characterises a condition in a patient. By a condition characterised by the presence of unwanted cells we include any biological or medical condition or disorder in which at least part of the pathology is mediated by the presence of unwanted cells. The condition may be caused by the presence of the unwanted cells or else the presence of the unwanted cells may be an effect of the condition. Examples of particular conditions include tumours (benign or malignant), autoimmune conditions, cardiovascular diseases, degenerative diseases, diabetes, allergic disease (eg asthma), neurodegenerative diseases such as Alzheimer's, transplantation patients and infectious diseases.

For autoimmune disease, the unwanted cells may represent cells of the adaptive or innate immune response, preferably T cells, but more preferably B cells. For cardiovascular disease, the unwanted cells may represent cells within atheromatous lesions such as macrophages. For degenerative diseases, the unwanted cells may represent cells which induce the neurodegenerative changes, for instance in Alzheimer's disease they may be microglia or astrocytes. For other degenerative diseases any cell which facilitates the process of degeneration or apoptosis may be considered a target. For processes such as aging where unwanted tissue builds up, for example in benign prostatic hyperplasia, non-malignant prostatic tissue would be a preferred target. For allergic disease, cells which participate in the allergic reaction such as tissue mast cells may be considered an ideal target, but also IgE secreting cells such as plasma cells or B cells. In transplantation, alloreactive lymphocytes would represent a preferred target cell. In the context of infectious disease, any cell harbouring a virus, bacteria or fungal pathogen may be considered a preferred target cell for example an HIV infected cell.

Immune Cell Binding Region of Further Moiety

By "immune cell binding region" we include the meaning of a region of the further moiety that is capable of binding to an immune cell. Preferably, the immune cell binding region is capable of selectively binding to an immune cell. For example, it is preferred if the immune cell binding region binds to an immune cell to a greater extent than it does any other type of cell, and most preferably binds to an immune cell only.

Generally, the immune cell binding region binds to an entity expressed by an immune cell, and preferably binds selectively to that entity. Thus, the further moiety may be a binding partner for an entity expressed on an immune cell wherein the immune cell binding region is the region of the further moiety that is responsible for binding. It is preferred if the immune cell binding region has a $K_d$ value for binding to an entity expressed by a given immune cell which is at least five or ten times lower than for at least one other entity expressed by another cell type, and preferably more than 100 or 500 times lower. More preferably, the immune cell binding region has a $K_d$ value for binding to an entity expressed by a given immune cell which is at least 1000 or 5000 times lower than for at least one other entity expressed by another cell type.

By 'immune cell', we include the meaning of any immune cell within the natural repertoire of cells in the immune system (e.g. human immune system) which, when activated, is able to bring about a change in the viability of a target cell. By 'viability of a target cell' we include the meaning of the target cell's ability to survive, proliferate and/or interact with other cells. Such interaction may either be direct, for example when the target cell contacts another cell, or indirect, for example when the target cell secretes substances which have an influence on the functioning of another distant cell. Generally, the immune cell is one that reduces one or more of the target cell's ability to survive, proliferate and/or interact with other cells, and preferably, the immune cell is one that kills the target cell. It will be appreciated therefore that the immune cell is preferably an immune effector cell.

In an embodiment, the immune cell is a member of the lymphoid cell lineage, and so may be any of a T cell or a natural killer (NK) cell. Advantageously, such cells will have a cytotoxic or an apoptotic effect on the unwanted cell.

In another embodiment, the immune cell is a member of the myeloid lineage, and so may be any of a mononuclear phagocyte (eg monocyte or macrophage), a neutrophilic granulocyte or a dendritic cell. Advantageously, such cells will have a cytotoxic, phagocytic or an apoptotic effect on the unwanted cell.

It is especially preferred if the immune cell is a T cell (eg cytotoxic T cell), and so the immune cell binding region of the further moiety is a T cell binding region. Thus, the invention provides a molecule comprising: (i) a targeting moiety capable of directly or indirectly targeting to unwanted cells, and (ii) a further moiety that has a masked T cell binding region so as to prevent binding of the further moiety to a T cell, wherein the masked immune cell binding region is capable of being selectively unmasked when the molecule is in the vicinity of the unwanted cells so as to allow binding of the further moiety to an immune cell.

By 'T cell', we include all types of T cell including CD4+, CD8+, γδ T cells and NK-T cells. Advantageously, the T cell is a cytotoxic T cell such that a cytotoxic T cell response is recruited. In this way, a cytotoxic effect can be exerted on the unwanted cells.

Entities expressed on the surface of T cells include any of CD3, T cell receptor (TCR), CD4, CD8 and CD28, and so when immune cell binding region is one that binds to T cells, the further moiety may be capable of binding to any of these antigens. For example, the further moiety may be an antibody that binds specifically to any of CD3, TCR, CD4, CD8 and CD28.

Entities expressed on the surface of other immune cells are well known in the art and, as with those on the surface of T cells, can be readily identified by interrogating the scientific literature. Examples include CD16, CD56, CD8, NK cell receptor (eg CD94:NKG2 heterodimer, Ly49 homodimer. γδ T cell receptor, pathogen recognition receptor, stress surveillance receptor, Killer-cell Ig-like receptor (KIR) or leukocyte inhibitory receptor), NKG2D, NKp46, CD2, CD28 and CD25.

The entity that is targeted by the immune cell binding region of the further moiety is preferably one which, when bound, leads to activation of the corresponding immune cell (eg T cell). Activation of an immune cell (eg T cell) can be determined by contacting isolated peripheral mononuclear blood cells with the further moiety comprising the immune cell binding region and using standard assays for cell proliferation known in the art. Suitable assays for determining the extent of an immune response include ELISpot, intracellular cytokine staining, HLA-peptide tetramer staining, proliferation assay, activation assays (eg CD69), CD107 mobilisation assays or metabolic assays (eg MU). Also suitable are assays to detect activation-induced secreted cytokines, for example using ELISA or multiplexed bead technologies.

For instance, in the preferred embodiment when the immune cell binding region of the further moiety is a T cell binding region, it is preferred if the T cell binding region is capable of binding to the CD3 antigen and/or TCR on T cells which are known to activate T cells. CD3 is present on all T cells and consists of subunits designated γ, δ, ε, ζ and η. The cytoplasmic tail of CD3 is sufficient to transduce the signals necessary for T cell activation in the absence of the other components of the TCR receptor complex. Normally, activation of T cell cytotoxicity depends first on binding of the TCR with a major histocompatibility complex (MHC) protein, itself bound to a foreign antigen, located on a separate cell. Only when this initial TCR-MHC binding has taken place can the CD3-dependent signally cascade responsible for T cell clonal expansion and, ultimately, T cell cytotoxicity ensue. However, when the further moiety of the molecule of the present invention binds to CD3 and/or the TCR, activation of cytotoxic T cells in the absence of independent TCR-MHC can take place by virtue of the crosslinking of the CD3 and/or TCR molecules mimicking an immune synapse formation. This means that T cells may be cytotoxically activated in a clonally independent fashion, ie in a manner which is independent of the specific TCR clone carried by the T cell. This allows for activation of the entire T cell compartment rather than only specific T cells of a certain clonal identity.

Conveniently, therefore, the immune cell binding region (eg T cell binding region) is one that binds to the immune cell in a way that mimicks the natural antigen binding to that immune cell which is known to activate the immune cell, eg to exert its effect on the viability of the target cell such as cytotoxicity.

The further moiety may be a polypeptide or a peptide. Preferably, the further moiety that contains the immune cell binding region is an antibody that specifically binds to an entity expressed by an immune cell (eg T cell). In a particularly preferred embodiment, the further moiety comprises one or more antibody variable domains (eg VH and VL domains) that specifically bind to an immune cell antigen. The further moiety may comprise aVH domain and a VL domain that, when paired, specifically bind to an immune cell antigen, or it may comprise a single VH domain or a single VL domain that is capable of binding to an immune cell antigen. Thus, the further moiety may be a single chain antibody construct such as a scFv antibody. It is especially preferred if the further moiety is an antibody (e.g. one that comprises at least one antibody variable domain such as a scFv antibody) that specifically binds to the CD3 antigen on T cells. A specific example is muromonab, but it will be appreciated that any anti-CD3 antibody may also be used. As will become clearer below and from the Figures, the further moiety may comprise two or more separate parts, such as polypeptide domains that are not necessarily encoded by contiguous polynucleotide sequences.

By the term 'masked', we include the meaning that the immune cell binding functionality of the immune cell binding region in the further moiety is substantially reduced or preferably inhibited completely. The masking of the immune cell binding region may be reversed by selective unmasking in the vicinity of the unwanted cells. Thus, in the masked state, the immune cell binding region is preferably unable to bind to an immune cell, while in the unmasked state the immune cell binding region is able to bind to an immune cell.

As described further below and exemplified in the figures, in a particularly preferred embodiment, the masking of the immune cell binding region is controlled by selective cleavage of one or more cleavage sites in the molecule. Thus, the molecule may contain one or more cleavage sites that are selectively cleavable when the molecule is in the vicinity of the unwanted cells. Suitable cleavage sites and agents that may cleave them are described in more detail below.

When the immune cell binding region is masked, the further moiety typically binds to an immune cell with an affinity at least 5 times less than when the immune cell binding region is unmasked, and more typically at least 10, 50 or 100 times less than when the immune cell binding region is unmasked. Most preferably, there is no detectable binding between the further moiety and an immune cell when the immune cell binding region is masked. Methods for assessing binding of moieties to cells are common in the art and include, for example, radiolabelled assays, fluorescently labelled techniques and flow cytometry. Conveniently, the further moiety is labelled and added to an immune cell under conditions conducive to binding in both the unmasked and masked states, and the extent of binding between the immune cell and further moiety in the masked and unmasked states compared. Biophysical techniques such as fluorescence correlation spectroscopy, fluorescence resonance energy transfer and analytical ultracentrifugation may also be used.

Preferably, binding of the immune cell binding region to an immune cell activates the immune cell. Thus, when the immune cell binding region is masked, the further moiety typically activates an immune cell at least 5 times less than when the immune cell binding region is unmasked, and more typically at least 10, 50 or 100 times less than when the immune cell binding region is unmasked. Most preferably, there is no detectable activation of immune cells when the immune cell binding region is masked. Methods for assessing activation of immune cells are standard in the art and include cell proliferation and cytokine secretion assays as described above.

In one embodiment, the immune cell binding region is masked by virtue of the further moiety being locked in a particular conformation in which the immune cell binding region is not accessible to an immune cell. The immune cell binding region may then be unmasked, for example, by selective cleavage of one or more cleavage sites in the molecule, when in the vicinity of the unwanted cells, which induces a conformational change in the further moiety that unmasks the immune cell binding region.

An example of this embodiment is shown in FIG. 1, where each of the targeting moiety and further moiety are respective scFv antibodies expressed on a single polypeptide chain. In FIG. 1, the targeting moiety (1) corresponds to one scFv unit that comprises two antibody variable domains (depicted as ovals in the figures): a first heavy chain variable domain (VH) and a first light chain variable domain (VL), which domains can pair together so as to form a first functional epitope binding site specific for an antigen expressed on an unwanted cell. The targeting moiety is attached to a further moiety (3) which corresponds to another scFv unit that comprises two antibody variable domains (depicted as ovals in the figures): a second VH domain and a second VL domain which can pair together so as to form a second functional epitope binding site specific for an antigen expressed on an immune cell (e.g. CD3 on a T cell). Thus, in FIG. 1, the immune cell binding region (4) of the further moiety corresponds to the second functional epitope binding site that is formed when the second VH domain pairs with the second VL domain. The second VH domain and second VL domain of the further moiety (3) in FIG. 1 are covalently joined by a polypeptide linker that is of an insufficient length to allow pairing between the two domains, which has the effect of locking the further moiety (3) in a particular conformation in which the immune cell binding region (4) is masked. However, when the molecule is in the vicinity of the unwanted cells (2), cleavage of a protease cleavage site (5) within the polypeptide linker joining the second VH domain and second VL domain, breaks the covalent linkage between the second VH domain and second VL domain so that the domains can pair and form the second functional epitope binding site. In other words, cleavage of the protease cleavage site has led to a conformation change in the further moiety (3) which unmasks the immune cell binding region (4).

Accordingly and as exemplified in FIG. 1, in one embodiment, the further moiety is a scFv antibody (3) in which the linker that joins the VH and VL domains is of insufficient length to allow pairing of the VH and VL domains such that the scFv antibody (3) cannot bind to the immune cell, and wherein selective cleavage of one or more cleavage sites (5) in said linker, when in the vicinity of the unwanted cells (2), induces pairing of the VH and VL domains such that the scFv antibody (3) can bind to the immune cell. Preferably, the immune cell binding region is a T cell binding region such as one that binds to the CD3 antigen on a T cell.

Preferably, the linker in this and other embodiments described herein is a peptide linker. However other linkers including polymers, nucleotides, nucleic acids, polysaccharide chains, lipid organic species (eg polyethylene glycol) may also be used.

Importantly, the linker that joins the VH and VL domains of the further moiety must be of insufficient length to allow pairing between the VH and VL domains.

By 'pairing between VH and VL domains' we include the meaning of correctly juxtaposing the matched VH and VL domains in a conformation that is identical to or approximates to the native paired state in a corresponding whole IgG parent antibody or scFv antibody such that the paired domains bind antigen with similar affinity to the corresponding whole IgG parent antibody or scFv antibody. Pairing of VH and VL domains may be assessed by any binding assay that monitors antibody/antigen binding, known in the art. Suitable techniques include ELISA, SPR, flow cytometry, FRET and structural studies. Competitive assays may also be employed where an excess of one or other of the VH or VL domains is used. If the excess causes binding to increase, this would imply that domains are unpaired. Additionally, functional immune cell assays may be used to assess pairing of VH and VL domains of the further moiety by investigating their ability to bind to, and activate, the corresponding immune cell. For example, if the VH and VL domains of the further moiety were specific for CD3 antigen on T cells, it may be appropriate to monitor correct pairing by performing functional T cell assays.

Generally, peptide linkers that join the VH domain and VL domain of a scFv antibody which are 14 amino acids or less are of insufficient length to allow pairing between the VH and VL domains. Thus, when the linker is a peptide, the peptide linker is typically 14 amino acids or less, such as 13, 12, 11, 10, 9, 8, 7, 6, 5, 4, 3, 2 or 1 amino acid in length.

Preferably, the targeting moiety of the embodiment in FIG. 1 comprises a VH domain and a VL domain which domains can pair together so as to form a functional epitope binding site specific for an antigen expressed on an unwanted cell. In this case, it is understood that the targeting moiety may be joined to the further moiety such that the molecule can be expressed as a single polypeptide chain.

In an alternative embodiment, the immune cell binding region is masked by virtue of the molecule comprising one or more masking moieties that prevent access of the immune cell binding region to the T cell. Thus, the molecule may comprise at least 1 or 2 or 3 or 4 or more masking moieties.

The one or more masking moieties may be any chemical moiety including a polypeptide or a peptide or an antibody or a small molecule. It is appreciated that any moiety that sterically blocks the immune cell binding region of the further moiety may be used as a masking moiety. Examples of suitable polypeptides include albumin and haemoglobulin. Such moieties can be readily identified by the skilled person. For example, antibodies against an antibody known to activate an immune cell (e.g a T cell activating scFv fragment) may be selected by phage display technology or by immunising a mouse with the appropriate antibody. Similarly, small molecule libraries may be screened to identify inhibitors of a known activator of an immune cell, for example in immune cell activation assays. Other techniques that may be used include molecular computer modelling and ribosomal display methods.

Figure 2:
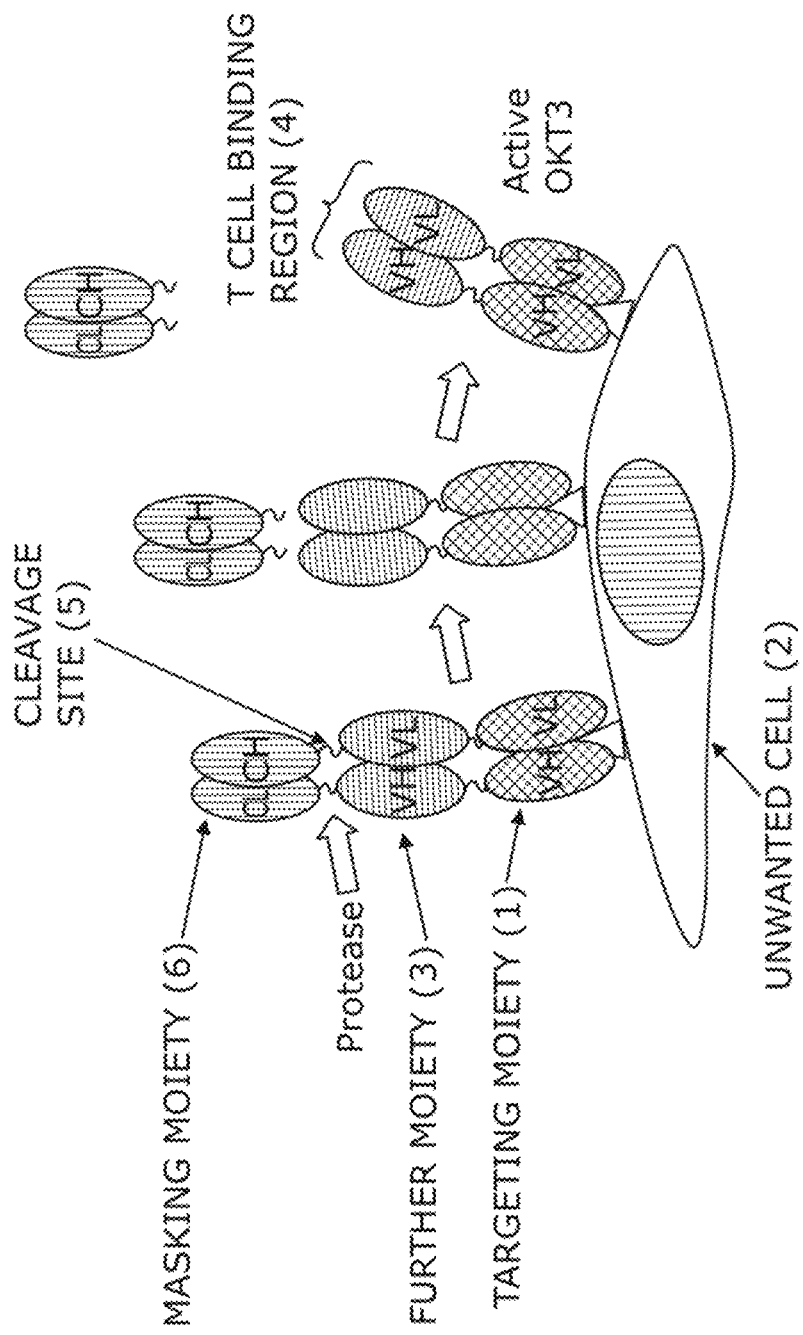
Figure 4:
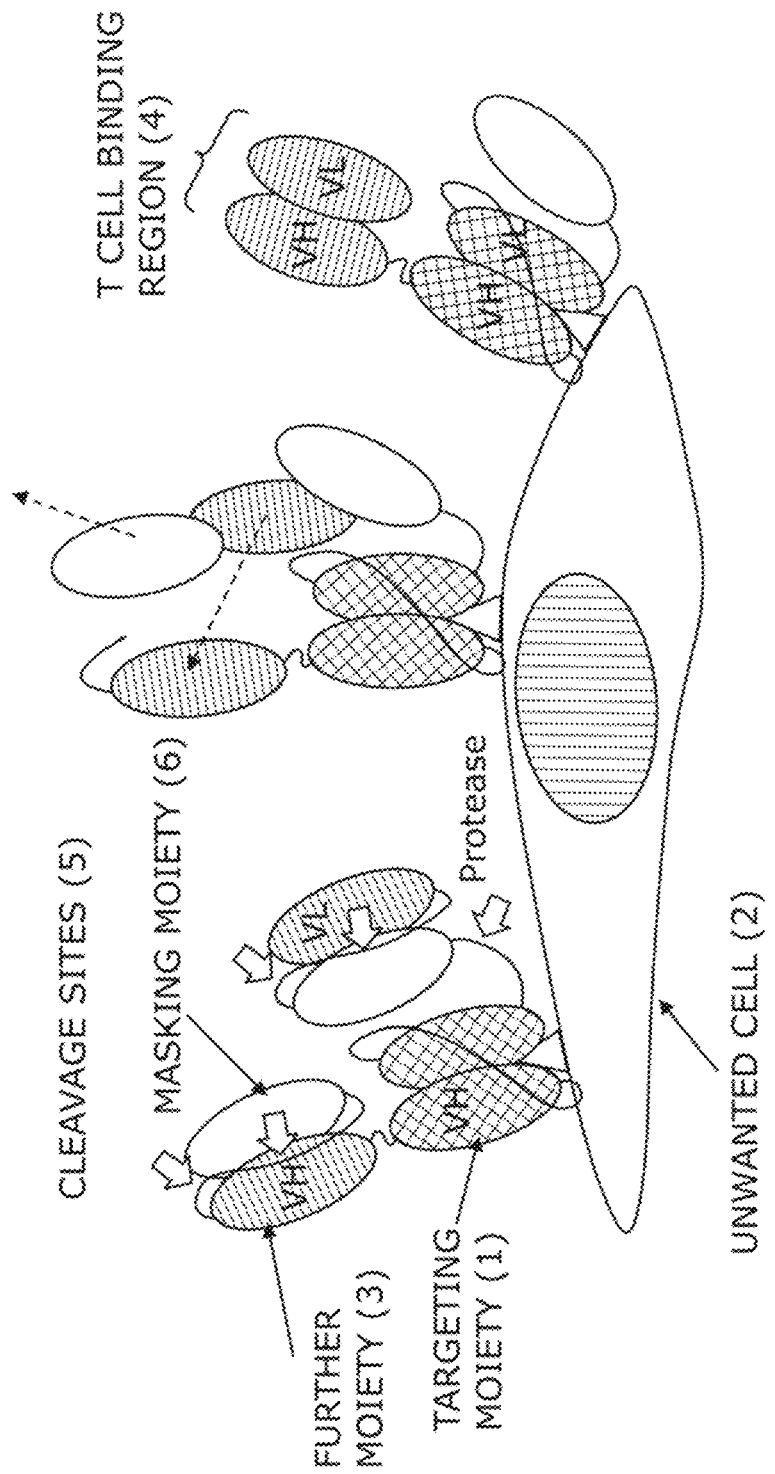

In one embodiment, and as exemplified in FIGS. 1, 2 and 4, the one or more masking moieties are immunoglobulin domains. The immunoglobulin domains may be either heavy chain or light chain domains derived from an antibody, and equally they may be either variable or constant domains derived from an antibody. Thus, the one or more masking moieties may be any one or more of a heavy chain variable domain (VH), a light chain variable domain (VL), a heavy chain constant domain (CH) and a light chain constant domain (CL). For example, the molecule may comprise two masking moieties which are a VL domain and a VH domain, or which are a CL domain and a CH domain. When the one or more masking moieties are a VL domain and a VH domain, the two domains may correspond to a scFv construct. It will be appreciated that when the one or more masking moieties are immunoglobulin domains, they may have an idiotype specific for the immune cell binding region of the targeting moiety. Preferably, however, the immunoglobulin domains used as masking moieties do not specifically bind any other protein in the body, and so are ones that have low toxicity.

Figure 3:
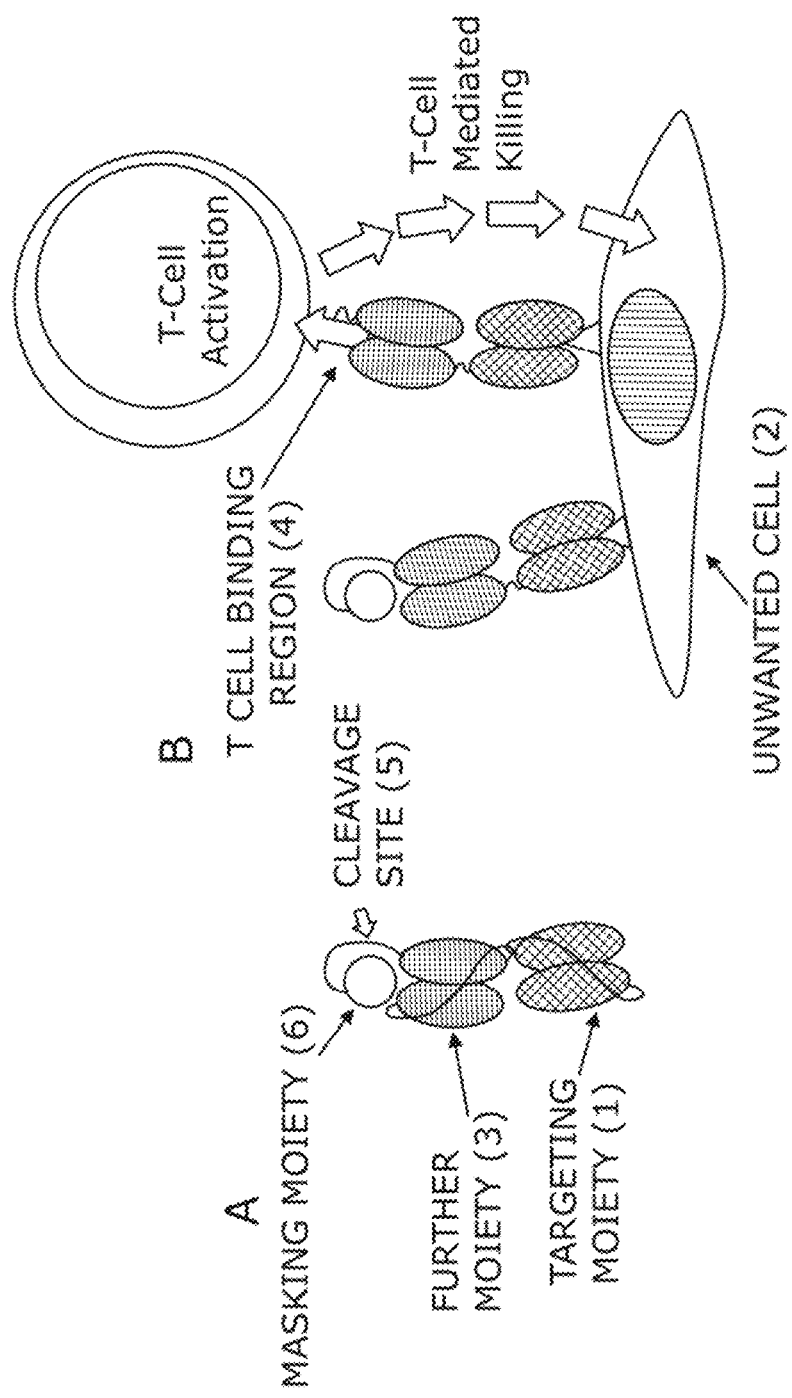

In another embodiment, and as exemplified in FIG. 3, the masking moiety is an immune cell surface antigen which the immune cell binding region of the further moiety is capable of binding to. For example, if the immune cell binding region of the further moiety binds to CD3 antigen on a T cell, the masking moiety may be the CD3 antigen (or one of the subunits thereof). In this scenario, the masking moiety competes with the T cell for binding to the immune cell binding region of the further moiety. It will be appreciated that the masking moiety need not be the entire immune cell surface antigen but may comprise only a portion of the immune cell surface antigen provided that the portion is capable of binding to the immune cell binding region. Suitable portions include the external parts of the immune cell surface antigens or portions thereof that can bind to the immune cell binding region. Thus, an external part of one of the subunits of the CD3 antigen (eg CD ε) may be used. Various methods may be used to determine binding between an immune cell surface antigen and an immune cell binding region, including, for example, enzyme linked immunosorbent assays (ELISA), surface plasmon resonance assays, chip-based assays, immunocytofluorescence, yeast two-hybrid technology and phage display which are common practice in the art and are described, for example, in Plant et al (1995) *Analyt Biochem*, 226(2), 342-348. and Sambrook et al (2001) Molecular Cloning A Laboratory Manual. Third Edition. Cold Spring Harbor Laboratory Press, Cold Spring Harbor, N.Y. Such portions of immune cell surface antigens are included in the definition immune cell surface antigen. Accordingly, the masking moiety may comprise an antigenic portion of the immune cell surface antigen (eg CD3 antigen). Generally, such portions comprise a stretch of amino acid residues of at least 8 amino acids, generally at least 10, 11, 12, 13, 14, 15, 16, 17, 18, 19 or 20 amino acids, and more generally at least 25, 50, 75 or 100 amino acids.

Typically, the one or more masking moieties are covalently attached to the molecule by one or more linkers. Such linkers may contain the one or more cleavage sites which are selectively cleavable when the molecule is in the vicinity of the unwanted cells, as described further below. Alternatively, the one or more masking moieties may be non-covalently attached to the molecule. In this case, the one or more cleavage sites described below may be located at one or more positions in the further moiety, such that upon cleavage, the part of the further moiety that is non-covalently bound to a masking moiety is released from the molecule, and the part of the further moiety that contains the immune cell binding region is retained in the molecule. As such, cleavage of the one or more cleavage sites has caused the immune cell binding region to be unmasked.

The one or more masking moieties may operate by simply blocking the immune cell binding region, so that the region is not accessible to an immune cell. In this instance there is no conformational change in the further moiety upon unmasking, and removal of the one or more masking moieties simply exposes the underlying T cell binding region so that it may bind an immune cell. It will be appreciated that the masking moiety may be any suitable chemical moiety that sterically blocks the immune cell region, as discussed above. Examples of this embodiment are shown in FIGS. 2 and 3, where the masking moiety is either an immunoglobulin domain or an immune cell surface antigen respectively.

In FIG. 2, as in FIG. 1, each of the targeting moiety and further moiety comprise respective pairs of VH and VL domains. Although FIG. 2 depicts a molecule containing two polypeptide chains, it will be appreciated that each of the targeting moiety and further moiety may also be respective scFv antibodies that are expressed on a single polypeptide chain. In the figure, the targeting moiety (1) comprises a first VH domain and a first VL domain which domains can pair together so as to form a first functional epitope binding site specific for an antigen expressed on an unwanted cell. The targeting moiety (1) is attached to a further moiety (3) that comprises a second VH domain and a second VL domain which can pair together so as to form a second functional epitope binding site specific for an antigen expressed on an immune cell (e.g. CD3), i.e. the immune cell binding region (4). However, the immune cell binding region (4) is masked by virtue of the second VH domain and second VL domain of the further moiety being joined to, respectively, a first masking moiety (6) comprising a CH domain and a second masking moiety (6) comprising a CL domain, which act to block the immune cell binding region. When the molecule is in the vicinity of the unwanted cells, cleavage of the protease cleavage sites (5) within the respective polypeptide linkers joining the second VH domain to the CH domain of the first masking moiety, and the second VL domain to the CL domain of the second masking moiety, acts to release the CH domain and CL domain masking moieties (6), such that the second functional epitope binding site becomes accessible to an immune cell. In other words, cleavage of the protease cleavage sites has unmasked the immune cell binding region.

Accordingly, and as exemplified in FIG. 2, in one embodiment, the molecule of the invention comprises:
  a further moiety (3) which comprises a VH domain and a VL domain that are capable of specifically binding to an immune cell,
  a first linker which joins the VH domain of the further moiety (3) to a CH domain of a first masking moiety (6), and
  a second linker which joins the VL domain of the further moiety (3) to a CL domain of a second masking moiety (6),
  such that the CH and CL domains of the first and second masking moieties (6) mask the binding regions of the VH and VL domains (4) so as to prevent binding of the further moiety to an immune cell, and
  wherein selective cleavage of one or more cleavage sites in said linkers (5), when in the vicinity of the unwanted cells (2), releases the first and second masking moieties (6) from the further moiety (3) so as to allow binding of the further moiety (3) to an immune cell. Preferably, the immune cell binding region is a T cell binding region such as one that binds to the CD3 antigen on a T cell. Preferably, the targeting moiety comprises a VH domain and a VL domain which domains can pair together so as to form a functional epitope binding site specific for an antigen expressed on an unwanted cell. The targeting moiety may or may not be expressed as a single polypeptide with the further moiety. It is appreciated in this embodiment that the first and second masking moieties may be any chemical moieties capable of preventing binding of the immune cell binding region to the immune cell, for example by steric blocking. For the avoidance of doubt therefore, although FIG. 2 depicts the masking moieties as CH and CL domains, it is understood that any one or more suitable masking moieties may be used, including any combination of immunoglobulin domains.

In FIG. 3, each of the targeting moiety and further moiety are respective scFv antibodies expressed as a single polypeptide chain. However, it will be appreciated that the respective VH and VL domains of the targeting moiety and further moiety of the molecule shown in FIG. 3 may equally be present on two polypeptide chains that pair together (eg scFv-like molecules or diabodies). In the figure, the targeting moiety (1) corresponds to one scFv unit that comprises a first VH domain and a first VL domain which domains can pair together so as to form a first functional epitope binding site specific for an antigen expressed on an unwanted cell. The targeting moiety is attached to a further moiety (3) that corresponds to another scFv unit which comprises a second VH domain and a second VL domain which can pair together so as to form a second functional epitope binding site specific for an antigen expressed on an immune cell (e.g. CD3), i.e. the immune cell binding region (4). However, the immune cell binding region is masked by virtue of a linker joining one of the second VH domain or second VL domain of the further moiety (3) to an immune cell surface antigen, i.e. the masking moiety (6), such that the immune cell surface antigen binds to and blocks the immune cell binding region (4). When the molecule is in the vicinity of the unwanted cells (2), cleavage of the cleavage site (5) within the linker allows the immune cell surface antigen (6) to leave the immune cell binding region, such that the second functional epitope binding site (4) becomes accessible to an immune cell. In other words, cleavage of the cleavage site (5) has unmasked the immune cell binding region (4). This embodiment involves competition between an immune cell and the immune cell surface antigen (6) within the molecule for binding to the immune cell binding region (4) of the further moiety (3). When not in the vicinity of unwanted cells (2), the immune cell surface antigen (6) is joined to the molecule by means of a linker which increases the local concentration of the immune cell surface antigen (6) and so favours binding of the immune cell surface antigen (6), rather than an immune cell, to the immune cell binding region (4). When the molecule is in the vicinity of unwanted cells (2), the linker joining the immune cell surface antigen (6) to the molecule is cleaved and so the immune cell surface antigen (6) is free to leave the immune cell binding region (4) such that an immune cell can now bind to it.

Accordingly, the molecule of the invention may comprise:
  a further moiety (3) which comprises a VH domain and a VL domain that are capable of specifically binding to an immune cell, and
  a linker which joins the further moiety (3) to an immune cell surface antigen (6), such that the immune cell surface antigen (6) binds to and masks the immune cell binding region (4) of the VH and VL domains so as to prevent binding of the further moiety (3) to an immune cell, wherein selective cleavage of one or more cleavage sites (5) in the linker, when in the vicinity of the unwanted cells (2), releases the immune cell surface antigen (6) from the immune cell binding region (4) of the VH and VL domains so as to allow binding of the further moiety (3) to an immune cell. Preferably, the immune cell binding region (4) is a T cell binding region such as one which specifically binds to the CD3 antigen of a T cell, and the immune cell surface antigen is a T cell surface antigen such as CD3 antigen or part thereof. Preferably, and as exemplified in FIG. 3, the targeting moiety comprises a VH domain and a VL domain which domains can pair together so as to form a functional epitope binding site specific for an antigen expressed on an unwanted cell. In this way, the targeting moiety and further moiety may correspond to two separate scFv units that can be expressed as a single polypeptide chain.

In an alternative embodiment, the one or more masking moieties operate by promoting a conformation of the further moiety such that the immune cell binding region is not accessible to an immune cell. In this case, unmasking does involve a conformational change in the further moiety such that the immune cell binding region now becomes accessible for binding to an immune cell. For example, when the further moiety comprises a pair of VH and VL domains that specifically bind to an antigen on an immune cell (e.g. CD3 antigen), it is appreciated that the one or more masking moieties may act to prevent pairing of the component VH and VL domains of the further moiety such that the VH and VL domains are not in the desired three dimensional conformation to bind to the immune cell antigen. Various methods may be used to prevent pairing of the VH and VL domains of a further moiety. One such method is exemplified in FIG. 4 which makes use of dummy variable domains that pair with the VH and VL domains of the further moiety such that the VH and VL domains of the further moiety cannot pair with each other. However, any suitable masking moiety that prevents pairing of the VH and VL domains of the further moiety, for example by binding to VH-VL interface protein surface, may be used. In all cases, the prevention of pairing of the VH and VL domains is lifted by cleavage of one or more cleavage sites within the molecule when the molecule is in the vicinity of the wanted cells.

In FIG. 4, the targeting moiety (1) corresponds to a scFv unit that comprises a first VH domain and a first VL domain which domains can pair together so as to form a first functional epitope binding site specific for an antigen expressed on an unwanted cell. A first linker joins the first VL domain of the targeting moiety (1) to a second VH domain of a further moiety (3), a second linker joins the first VH domain of the targeting moiety (1) to a first masking moiety comprising a VH domain (6), a third linker joins the second VH domain of the further moiety (3) to a second masking moiety comprising a VL domain (6), and a fourth linker joins the VH domain of the first masking moiety to a second VL domain of the further moiety (3); wherein the second VH and second VL domains of the further moiety, when paired, form a second functional epitope binding site specific for an antigen expressed on an immune cell (e.g. CD3 antigen on a T cell), i.e. the immune cell binding region (4); and wherein the third and fourth linkers are of a sufficient length so that the second VH domain of the further moiety (3) is paired with the VL domain of the second masking moiety (6), and the second VL domain of the further moiety (3) is paired with the VH domain of the first masking moiety (6). Thus, the first and second masking moieties in FIG. 4 prevent the second VH and second VL domain of the further moiety from pairing and so mask the immune cell binding region (4). In this way, the variable domains of the masking moieties act as 'dummy' VH and VL domains which pair with the second VH and VL domains of the further moiety, and the third and fourth linkers stabilise this configuration by preventing domain exchange. However, when the molecule is in the vicinity of the unwanted cells (2), cleavage of one or more cleavage sites (5) present in the third and fourth linkers release the second VH domain and second VL domain from pairing with the VL domain of the second masking moiety (6) and the VH domain of the first masking moiety (6), respectively, so that the second VH domain and second VL domain of the further moiety can pair to form the immune cell binding region (4). In other words, cleavage of the cleavage sites (5) present in the third and fourth linkers has allowed conformational rearrangement of the molecule wherein the second VH domain and second VL domain are correctly paired so that the immune cell binding ability is recovered. The immune cell binding region (4) has been unmasked.

Accordingly, in one embodiment, the molecule of the invention comprises:
 a further moiety (3) which comprises separately a first VH and a first VL domain which when paired are capable of specifically binding to an immune cell,
 a linker which joins the first VH domain to a second VL domain of a first masking moiety (6), and
 a linker which joins the first VL domain to a second VH domain of a second masking moiety (6),
 such that the first VH and first VL domains of the further moiety are not paired and the further moiety cannot bind to the immune cell, and
 wherein selective cleavage of one or more cleavage sites (5) in said linkers, when in the vicinity of the unwanted cells (2), allows pairing of the first VH and first VL domains such that the further moiety can bind to the immune cell. Preferably, the immune cell binding region (4) is a T cell binding region such as one that specifically binds to the CD3 antigen on a T cell. Given that the masking moieties mask the immune cell binding region, it will of course be appreciated in this embodiment, that the second VH domain and second VL domain of the masking moieties are not ones which are capable of respectively pairing with the first VL domain and first VH domain of the further moiety so as to form a functional epitope binding site specific for an antigen expressed on an immune cell (e.g. an antigen expressed on a T cell such as CD3 antigen). In any event, it will further be appreciated that any suitable masking moiety that prevents pairing of the VH and VL domains of the further moiety may be substituted for the VH and VL masking moieties shown in FIG. 4. Preferably, and as exemplified in FIG. 4, the targeting moiety comprises a VH domain and a VL domain which domains can pair together so as to form a functional epitope binding site specific for an antigen expressed on an unwanted cell. In this case, it is understood that the targeting moiety may be joined to the further moiety and the one or more masking moieties such that the molecule can be expressed as a single polypeptide chain. The targeting moiety may be in the middle of the polypeptide chain flanked by the further moiety and/or one or more masking moieties. For example, the targeting moiety may be a scFv unit, one domain of which is joined to a first VL domain of the further moiety and the other domain of which is joined to a second VL domain of a first masking moiety, or the targeting moiety may be a scFv unit, one domain of which is joined to the first VH domain of the further moiety and the other domain of which is joined to second VH domain of the second masking moiety. Alternatively, the targeting moiety may be at either end of the polypeptide chain.

Preferably, and as exemplified in FIG. 4, the linker which joins the first VH domain to a second VL domain of a first masking moiety, is of sufficient length to allow the first VH domain to be paired with the second VL domain, and the linker which joins the first VL domain to a second VH domain of a second masking moiety is of sufficient length to allow the first VL domain to be paired with the second VH domain. Typically, the linkers are peptides and so must have a sufficient number of amino acids to allow pairing between the VH and VL domains. Generally, peptide linkers that join a VH domain and a VL domain of a scFv antibody which are 15 amino acids or more are of sufficient length to allow pairing between the VH and VL domains. Thus, when said linkers are peptides, they are typically 15 amino acids or more in length, such as at least 16, 17, 18, 19, 20, 21, 22, 23, 24, 25, 26, 27, 28, 29, 30, 31, 32, 33, 34, 35, 36, 37, 38, 39 or 40 amino acids in length. Pairing between VH and VL domains can be assessed by routine methods known in the art, including those described above.

Selective Unmasking of Immune Cell Binding Region

By 'selective unmasking' we include the meaning that the immune cell binding region is unmasked by the presence of an agent that selectively resides in the in the vicinity of the unwanted cells, which agent acts to unmask the immune cell binding region. Preferably, the agent that unmasks the immune cell binding region resides in the vicinity of the unwanted cells at least five or ten times higher than the concentration of the agent outside the vicinity of the unwanted cells, and more preferably at least 100 or 500 or 1000 times higher. Most preferably, the agent that unmasks the immune cell binding region binding region is found only in the vicinity of the unwanted cells.

In a preferred embodiment, the immune cell binding region is unmasked by selective cleavage of one or more cleavage sites in the molecule when in the vicinity of the unwanted cells. In this case, the agent is one that cleaves the one or more cleavage sites. In other words, the immune cell binding region may be unmasked by means of one or more cleavage sites within the molecule being cleaved selectively in the vicinity of the unwanted cells.

Thus, the invention includes a molecule comprising (i) a targeting moiety capable of directly or indirectly targeting to unwanted cells, and (ii) a further moiety that has a masked immune cell binding region so as to prevent binding of the further moiety to an immune cell, wherein selective cleavage of one or more cleavage sites in the molecule when in the vicinity of the unwanted cells unmasks the immune cell binding region so as to allow binding of the further moiety to an immune cell. Preferably, the immune cell binding region is a T cell binding region including one that binds to the CD3 antigen and/or TCR on a T cell. Accordingly, it is appreciated that the invention provides a molecule comprising (i) a targeting moiety capable of directly or indirectly targeting to unwanted cells, and (ii) a further moiety that has a masked T cell binding region so as to prevent binding of the further moiety to a T cell, wherein selective cleavage of one or more cleavage sites in the molecule when in the vicinity of the unwanted cells unmasks the T cell binding region so as to allow binding of the further moiety to a T cell.

By "cleavage site that is cleavable selectively in the vicinity of the unwanted cells" we include the meaning of a site that can only be cleaved by an agent which resides selectively in the vicinity of the unwanted cells, so as to unmask the immune cell binding region. Preferably, the agent that cleaves the one or more cleavage sites resides in the vicinity of the unwanted cells at a concentration at least five times or ten times higher than the concentration of the agent outside the vicinity of the unwanted cells, and more preferably at a concentration at least 100 or 500 or 1000 times higher. Most preferably, the agent that cleaves the one or more cleavage sites is found only in the vicinity of the unwanted cells. For example, when the unwanted cells are particular tumour cells (e.g. breast tumour cells), the one or more cleavage sites may be ones that are cleaved by an agent which resides selectively in the particular tumour (e.g. breast tumour) but which agent does not reside outside the vicinity of the particular tumour (e.g. breast tumour).

By 'in the vicinity of cells', we include the meaning of either at or near to the surface of the cells, or both, or in the environment that immediately surrounds the cells e.g. blood, lymph, and other body fluids.

The one or more cleavage sites are selectively cleaved in the vicinity of the unwanted cells so that the immune cell binding region of the further moiety is preferentially unmasked in the vicinity of the unwanted cells so as to recruit immune cells preferentially to unwanted cells rather than wanted cells. Thus, it is preferred that the one or more cleavage sites are ones that are selectively cleaved such that the immune cell binding region is unmasked in the vicinity of the unwanted cells at least five times or ten times more than the extent to which it is unmasked in the vicinity of wanted cells, and more preferably at least 100 or 500 or 1000 times more. Most preferably, the immune cell binding region is not unmasked in the vicinity of wanted cells, and therefore immune cells are not recruited to wanted cells.

For a given unwanted cell, the skilled person will be able to identify appropriate one or more cleavage sites that are selectively cleavable in the vicinity of the unwanted cell, using established methods in the art. For example, which proteases cleave which peptides can be assessed by consulting peptide libraries and studying an MS analysis of the fragmentation profile following cleavage. Also, published literature of protease cleavage motifs and peptide cleavage data can be searched as described further below. Gene expression and proteomic data may also be analysed to identify which proteases are expressed by particular unwanted cells.

By virtue of the one or more cleavage sites being selectively cleavable in the vicinity of the unwanted cells, the immune cell binding region is selectively unmasked in the vicinity of the unwanted cells.

The one or more cleavage sites may be located between separate parts of the further moiety (e.g. separate immunoglobulin domains), such that upon cleavage of the cleavage sites a conformational change is induced whereby the separate parts of the further moiety are rearranged so as to unmask the immune cell binding region (see FIG. 1). The one or more cleavage sites may be located between the one or more masking moieties and either the further moiety and/or targeting moiety. Thus, the one or more cleavage sites may be located between the one or more masking moieties and the further moiety (see FIGS. 2 and 3), or they may be located between the one or more masking moieties and the targeting moiety (see FIG. 4), or they may be located between the one or more masking moieties and each of the targeting moiety and further moiety (see FIG. 4). When any of the further moiety, targeting moiety and masking moiety comprise one or more immunoglobulin domains, it is appreciated that the one or more cleavage sites should be located between the immunoglobulin domains to allow movement of whole immunoglobulin domains rather than movement of only parts of the domains, upon unmasking of the immune cell binding region.

The cleavage site may be one that is cleavable by an enzyme such as any of a protease, a nuclease, a lipase, a lyase, a phosphatase or a carbohydrase, which may or may not be membrane bound. Accordingly, it will be appreciated that the cleavage site may be one that is cleavable by an enzyme that is bound to the membrane of, or secreted by, the unwanted cell.

Generally, the cleavage site is a protease cleavage site. Thus, when the unwanted cells are tumour cells, the one or more cleavage sites may be cleavable selectively by proteases that reside in the vicinity of the tumour cells. In other words, the protease cleavage site may be one that is cleavable by a tumour associated protease. It is well known that during tumour development, tumours aberrantly express proteases which allow them to invade local tissues and eventually metastasise.

The protease may include any of a cysteine protease (including the Cathepsin family B, L, S etc), an aspartyl protease (including Cathepsin D and E) and a serine protease (including Cathepsin A and G, Thrombin, Plasmin, Urokinase, Tissue Plasminogen Activator). The protease may be a metalloproteinase (MMP1-28) including both membrane bound (MMP14-17 and MMP24-25) and secreted forms (MMP1-13 and MMP18-23 and MMP26-28). The protease may belong to the A Disintegrin and Metalloproteinase (ADAM) and A Disintegrin, or Metalloproteinase with Thrombospondin Motifs (ADAMTS) families of proteases. Other examples include CD10 (CALLA) and prostate specific antigen (PSA). It is appreciated that the proteases may or may not be membrane bound.

Protease cleavage sites are well known in the scientific literature, and linker sequences comprising such cleavage sites can be readily constructed using established genetic engineering techniques, or by synthetic synthesis techniques known in the art.

Protease cleavage sites may be ones that are cleavable by any of the proteases listed in Table 4 below, which indicates the expression of selected proteases in various tumour types. Candidate substrates for the proteases are provided. Thus, in order to treat a particular tumour type, the skilled person will typically select one or more protease cleavage sites that are selectively cleaved by a protease known to be highly expressed in that tumour type, as seen from the table. For example, to treat breast cancer, it is preferred to use a protease cleavage site cleavable by any of uPA, tPA, matriptase, matriptase 2, Cathepsin K, Cathepsin 0, MMP1, MMP2, MMP3, MMP11, MMP12, MMP17, ADAM9, ADAM12, ADAM15, ADAM17, ADAM28 or ADAMTS15, and so on. It will be appreciated that the one or more protease cleavage sites selected by the skilled person include ones that are cleaved by different proteases, which may help to improve the specificity of the molecule of the invention further.

Similarly, Table 5 lists tumour sites in which ADAM protease overexpression has been reported, and so in an embodiment, the one or more cleavage sites are selectively cleavable by one of the ADAM proteases listed in Table 5. Accordingly, the molecule may be used to prevent or treat the corresponding tumour type.

The one or more cleavage sites may be selectively cleavable by any of the following human proteases (MEROPS peptidase database number provided in parentheses; Rawlings N. D., Morton F. R., Kok, C. Y., Kong, J. & Barrett A. J. (2008) MEROPS: the peptidase database. *Nucleic Acids Res.* 36 Database issue, D320-325): pepsin A (MER000885), gastricsin (MER000894), memapsin-2 (MER005870), renin (MER000917), cathepsin D (MER000911), cathepsin E (MER000944), memapsin-1 (MER005534), napsin A (MER004981), Mername-AA034 peptidase (MER014038), pepsin A4 (MER037290), pepsin A5 (*Homo sapiens*) (MER037291), hCG1733572 (*Homo sapiens*)-type putative peptidase (MER107386), napsin B pseudogene (MER004982), CYMP g.p. (*Homo sapiens*) (MER002929), subfamily A1A unassigned peptidases (MER181559), mouse mammary tumor virus retropepsin (MER048030), rabbit endogenous retrovirus endopeptidase (MER043650), S71-related human endogenous retropepsin (MER001812), RTVL-H-type putative peptidase (MER047117), RTVL-H-type putative peptidase (MER047133), RTVL-H-type putative peptidase (MER047160), RTVL-H-type putative peptidase (MER047206), RTVL-H-type putative peptidase (MER047253), RTVL-H-type putative peptidase (MER047260), RTVL-H-type putative peptidase (MER047291), RTVL-H-type putative peptidase (MER047418), RTVL-H-type putative peptidase (MER047440), RTVL-H-type putative peptidase (MER047479), RTVL-H-type putative peptidase (MER047559), RTVL-H-type putative peptidase (MER047583), RTVL-H-type putative peptidase (MER015446), human endogenous retrovirus retropepsin homologue 1 (MER015479), human endogenous retrovirus retropepsin homologue 2 (MER015481), endogenous retrovirus retropepsin pseudogene 1 (*Homo sapiens* chromosome 14) (MER029977), endogenous retrovirus retropepsin pseudogene 2 (*Homo sapiens* chromosome 8) (MER029665), endogenous retrovirus retropepsin pseudogene 3 (*Homo sapiens* chromosome 17) (MER002660), endogenous retrovirus retropepsin pseudogene 3 (*Homo sapiens* chromosome 17) (MER030286), endogenous retrovirus retropepsin pseudogene 3 (*Homo sapiens* chromosome 17) (MER047144), endogenous retrovirus retropepsin pseudogene 5 (*Homo sapiens* chromosome 12) (MER029664), endogenous retrovirus retropepsin pseudogene 6 (*Homo sapiens* chromosome 7) (MER002094), endogenous retrovirus retropepsin pseudogene 7 (*Homo sapiens* chromosome 6) (MER029776), endogenous retrovirus retropepsin pseudogene 8 (*Homo sapiens* chromosome Y) (MER030291), endogenous retrovirus retropepsin pseudogene 9 (*Homo sapiens* chromosome 19) (MER029680), endogenous retrovirus retropepsin pseudogene 10 (*Homo sapiens* chromosome 12) (MER002848), endogenous retrovirus retropepsin pseudogene 11 (*Homo sapiens* chromosome 17) (MER004378), endogenous retrovirus retropepsin pseudogene 12 (*Homo sapiens* chromosome 11) (MER003344), endogenous retrovirus retropepsin pseudogene 13 (*Homo sapiens* chromosome 2 and similar) (MER029779), endogenous retrovirus retropepsin pseudogene 14 (*Homo sapiens* chromosome 2) (MER029778), endogenous retrovirus retropepsin pseudogene 15 (*Homo sapiens* chromosome 4) (MER047158), endogenous retrovirus retropepsin pseudogene 15 (*Homo sapiens* chromosome 4) (MER047332), endogenous retrovirus retropepsin pseudogene 15 (*Homo sapiens* chromosome 4) (MER003182), endogenous retrovirus retropepsin pseudogene 16 (MER047165), endogenous retrovirus retropepsin pseudogene 16 (MER047178), endogenous retrovirus retropepsin pseudogene 16 (MER047200), endogenous retrovirus retropepsin pseudogene 16 (MER047315), endogenous retrovirus retropepsin pseudogene 16 (MER047405), endogenous retrovirus retropepsin pseudogene 16 (MER030292), endogenous retrovirus retropepsin pseudogene 17 (*Homo sapiens* chromosome 8) (MER005305), endogenous retrovirus retropepsin pseudogene 18 (*Homo sapiens* chromosome 4) (MER030288), endogenous retrovirus retropepsin pseudogene 19 (*Homo sapiens* chromosome 16) (MER001740), endogenous retrovirus retropepsin pseudogene 21 (*Homo sapiens*) (MER047222), endogenous retrovirus retropepsin pseudogene 21 (*Homo sapiens*) (MER047454), endogenous retrovirus retropepsin pseudogene 21 (*Homo sapiens*) (MER047477), endogenous retrovirus retropepsin pseudogene 21 (*Homo sapiens*) (MER004403), endogenous retrovirus retropepsin pseudogene 22 (*Homo sapiens* chromosome X) (MER030287), subfamily A2A non-peptidase homologues (MER047046), subfamily A2A non-peptidase homologues (MER047052), subfamily A2A non-peptidase homologues (MER047076), subfamily A2A non-peptidase homologues (MER047080), subfamily A2A non-peptidase homologues (MER047088), subfamily A2A non-peptidase homologues (MER047089), subfamily A2A non-peptidase homologues (MER047091), subfamily A2A non-peptidase homologues (MER047092), subfamily A2A non-peptidase homologues (MER047093), subfamily A2A non-peptidase homologues (MER047094), subfamily A2A non-peptidase homologues (MER047097), subfamily A2A non-peptidase homologues (MER047099), subfamily A2A non-peptidase homologues (MER047101), subfamily A2A non-peptidase homologues (MER047102), subfamily A2A non-peptidase homologues (MER047107), subfamily A2A non-peptidase homologues (MER047108), subfamily A2A non-peptidase homologues (MER047109), subfamily A2A non-peptidase homologues (MER047110), subfamily A2A non-peptidase homologues (MER047111), subfamily A2A non-peptidase homologues (MER047114), subfamily A2A non-peptidase homologues (MER047118), subfamily A2A non-peptidase homologues (MER047121), subfamily A2A non-peptidase homologues (MER047122), subfamily A2A non-peptidase homologues (MER047126), subfamily A2A non-peptidase homologues (MER047129), subfamily A2A non-peptidase homologues (MER047130), subfamily A2A non-peptidase homologues (MER047134), subfamily A2A non-peptidase homologues (MER047135), subfamily A2A non-peptidase homologues (MER047137), subfamily A2A non-peptidase homologues (MER047140), subfamily A2A non-peptidase homologues (MER047141), subfamily A2A non-peptidase homologues (MER047142), subfamily A2A non-peptidase homologues (MER047148), subfamily A2A non-peptidase homologues (MER047149), subfamily A2A non-peptidase homologues (MER047151), subfamily A2A non-peptidase homologues (MER047154), subfamily A2A non-peptidase homologues (MER047155), subfamily A2A non-peptidase homologues (MER047156), subfamily A2A non-peptidase homologues (MER047157), subfamily A2A non-peptidase homologues (MER047159), subfamily A2A non-peptidase homologues (MER047161), subfamily A2A non-peptidase homologues (MER047163), subfamily A2A non-peptidase homologues (MER047166), subfamily A2A non-peptidase homologues (MER047171), subfamily A2A non-peptidase homologues (MER047173), subfamily A2A non-peptidase homologues (MER047174), subfamily A2A non-peptidase homologues (MER047179), subfamily A2A non-peptidase homologues (MER047183), subfamily A2A non-peptidase homologues (MER047186), subfamily A2A non-peptidase homologues (MER047190), subfamily A2A non-peptidase homologues (MER047191), subfamily A2A non-peptidase homologues (MER047196), subfamily A2A non-peptidase homologues (MER047198), subfamily A2A non-peptidase homologues (MER047199), subfamily A2A non-peptidase homologues (MER047201), subfamily A2A non-peptidase homologues (MER047202), subfamily A2A non-peptidase homologues (MER047203), subfamily A2A non-peptidase homologues (MER047204), subfamily A2A non-peptidase homologues (MER047205), subfamily A2A non-peptidase homologues (MER047207), subfamily A2A non-peptidase homologues (MER047208), subfamily A2A non-peptidase homologues (MER047210), subfamily A2A non-peptidase homologues (MER047211), subfamily A2A non-peptidase homologues (MER047212), subfamily A2A non-peptidase homologues (MER047213), subfamily A2A non-peptidase homologues (MER047215), subfamily A2A non-peptidase homologues (MER047216), subfamily A2A non-peptidase homologues (MER047218), subfamily A2A non-peptidase homologues (MER047219), subfamily A2A non-peptidase homologues (MER047221), subfamily A2A non-peptidase homologues (MER047224), subfamily A2A non-peptidase homologues (MER047225), subfamily A2A non-peptidase homologues (MER047226), subfamily A2A non-peptidase homologues (MER047227), subfamily A2A non-peptidase homologues (MER047230), subfamily A2A non-peptidase homologues (MER047232), subfamily A2A non-peptidase homologues (MER047233), subfamily A2A non-peptidase homologues (MER047234), subfamily A2A non-peptidase homologues (MER047236), subfamily A2A non-peptidase homologues (MER047238), subfamily A2A non-peptidase homologues (MER047239), subfamily A2A non-peptidase homologues (MER047240), subfamily A2A non-peptidase homologues (MER047242), subfamily A2A non-peptidase homologues (MER047243), subfamily A2A non-peptidase homologues (MER047249), subfamily A2A non-peptidase homologues (MER047251), subfamily A2A non-peptidase homologues (MER047252), subfamily A2A non-peptidase homologues (MER047254), subfamily A2A non-peptidase homologues (MER047255), subfamily A2A non-peptidase homologues (MER047263), subfamily A2A non-peptidase homologues (MER047265), subfamily A2A non-peptidase homologues (MER047266), subfamily A2A non-peptidase homologues (MER047267), subfamily A2A non-peptidase homologues (MER047268), subfamily A2A non-peptidase homologues (MER047269), subfamily A2A non-peptidase homologues (MER047272), subfamily A2A non-peptidase homologues (MER047273), subfamily A2A non-peptidase homologues (MER047274), subfamily A2A non-peptidase homologues (MER047275), subfamily A2A non-peptidase homologues (MER047276), subfamily A2A non-peptidase homologues (MER047279), subfamily A2A non-peptidase homologues (MER047280), subfamily A2A non-peptidase homologues (MER047281), subfamily A2A non-peptidase homologues (MER047282), subfamily A2A non-peptidase homologues (MER047284), subfamily A2A non-peptidase homologues (MER047285), subfamily A2A non-peptidase homologues (MER047289), subfamily A2A non-peptidase homologues (MER047290), subfamily A2A non-peptidase homologues (MER047294), subfamily A2A non-peptidase homologues (MER047295), subfamily A2A non-peptidase homologues (MER047298), subfamily A2A non-peptidase homologues (MER047300), subfamily A2A non-peptidase homologues (MER047302), subfamily A2A non-peptidase homologues (MER047304), subfamily A2A non-peptidase homologues (MER047305), subfamily A2A non-peptidase homologues (MER047306), subfamily A2A non-peptidase homologues (MER047307), subfamily A2A non-peptidase homologues (MER047310), subfamily A2A non-peptidase homologues (MER047311), subfamily A2A non-peptidase homologues (MER047314), subfamily A2A non-peptidase homologues (MER047318), subfamily A2A non-peptidase homologues (MER047320), subfamily A2A non-peptidase homologues (MER047321), subfamily A2A non-peptidase homologues (MER047322), subfamily A2A non-peptidase homologues (MER047326), subfamily A2A non-peptidase homologues (MER047327), subfamily A2A non-peptidase homologues (MER047330), subfamily A2A non-peptidase homologues (MER047333), subfamily A2A non-peptidase homologues (MER047362), subfamily A2A non-peptidase homologues (MER047366), subfamily A2A non-peptidase homologues (MER047369), subfamily A2A non-peptidase homologues (MER047370), subfamily A2A non-peptidase homologues (MER047371), subfamily A2A non-peptidase homologues (MER047375), subfamily A2A non-peptidase homologues (MER047376), subfamily A2A non-peptidase homologues (MER047381), subfamily A2A non-peptidase homologues (MER047383), subfamily A2A non-peptidase homologues (MER047384), subfamily A2A non-peptidase homologues (MER047385), subfamily A2A non-peptidase homologues (MER047388), subfamily A2A non-peptidase homologues (MER047389), subfamily A2A non-peptidase homologues (MER047391), subfamily A2A non-peptidase homologues (MER047394), subfamily A2A non-peptidase homologues (MER047396), subfamily A2A non-peptidase homologues (MER047400), subfamily A2A non-peptidase homologues (MER047401), subfamily A2A non-peptidase homologues (MER047403), subfamily A2A non-peptidase homologues (MER047406), subfamily A2A non-peptidase homologues (MER047407), subfamily A2A non-peptidase homologues (MER047410), subfamily A2A non-peptidase homologues (MER047411), subfamily A2A non-peptidase homologues (MER047413), subfamily A2A non-peptidase homologues (MER047414), subfamily A2A non-peptidase homologues (MER047416), subfamily A2A non-peptidase homologues (MER047417), subfamily A2A non-peptidase homologues (MER047420), subfamily A2A non-peptidase homologues (MER047423), subfamily A2A non-peptidase homologues (MER047424), subfamily A2A non-peptidase homologues (MER047428), subfamily A2A non-peptidase homologues (MER047429), subfamily A2A non-peptidase homologues (MER047431), subfamily A2A non-peptidase homologues (MER047434), subfamily A2A non-peptidase homologues (MER047439), subfamily A2A non-peptidase homologues (MER047442), subfamily A2A non-peptidase homologues (MER047445), subfamily A2A non-peptidase homologues (MER047449), subfamily A2A non-peptidase homologues (MER047450), subfamily A2A non-peptidase homologues (MER047452), subfamily A2A non-peptidase homologues (MER047455), subfamily A2A non-peptidase homologues (MER047457), subfamily A2A non-peptidase homologues (MER047458), subfamily A2A non-peptidase homologues (MER047459), subfamily A2A non-peptidase homologues (MER047463), subfamily A2A non-peptidase homologues (MER047468), subfamily A2A non-peptidase homologues (MER047469), subfamily A2A non-peptidase homologues (MER047470), subfamily A2A non-peptidase homologues (MER047476), subfamily A2A non-peptidase homologues (MER047478), subfamily A2A non-peptidase homologues (MER047483), subfamily A2A non-peptidase homologues (MER047488), subfamily A2A non-peptidase homologues (MER047489), subfamily A2A non-peptidase homologues (MER047490), subfamily A2A non-peptidase homologues (MER047493), subfamily A2A non-peptidase homologues (MER047494), subfamily A2A non-peptidase homologues (MER047495), subfamily A2A non-peptidase homologues (MER047496), subfamily A2A non-peptidase homologues (MER047497), subfamily A2A non-peptidase homologues (MER047499), subfamily A2A non-peptidase homologues (MER047502), subfamily A2A non-peptidase homologues (MER047504), subfamily A2A non-peptidase homologues (MER047511), subfamily A2A non-peptidase homologues (MER047513), subfamily A2A non-peptidase homologues (MER047514), subfamily A2A non-peptidase homologues (MER047515), subfamily A2A non-peptidase homologues (MER047516), subfamily A2A non-peptidase homologues (MER047520), subfamily A2A non-peptidase homologues (MER047533), subfamily A2A non-peptidase homologues (MER047537), subfamily A2A non-peptidase homologues (MER047569), subfamily A2A non-peptidase homologues (MER047570), subfamily A2A non-peptidase homologues (MER047584), subfamily A2A non-peptidase homologues (MER047603), subfamily A2A non-peptidase homologues (MER047604), subfamily A2A non-peptidase homologues (MER047606), subfamily A2A non-peptidase homologues (MER047609), subfamily A2A non-peptidase homologues (MER047616), subfamily A2A non-peptidase homologues (MER047619), subfamily A2A non-peptidase homologues (MER047648), subfamily A2A non-peptidase homologues (MER047649), subfamily A2A non-peptidase homologues (MER047662), subfamily A2A non-peptidase homologues (MER048004), subfamily A2A non-peptidase homologues (MER048018), subfamily A2A non-peptidase homologues (MER048019), subfamily A2A non-peptidase homologues (MER048023), subfamily A2A non-peptidase homologues (MER048037), subfamily A2A unassigned peptidases (MER047164), subfamily A2A unassigned peptidases (MER047231), subfamily A2A unassigned peptidases (MER047386), skin aspartic protease (MER057097), presenilin 1 (MER005221), presenilin 2 (MER005223), impas 1 peptidase (MER019701), impas 1 peptidase (MER184722), impas 4 peptidase (MER019715), impas 2 peptidase (MER019708), impas 5 peptidase (MER019712), impas 3 peptidase (MER019711), possible family A22 pseudogene (*Homo sapiens* chromosome 18) (MER029974), possible family A22 pseudogene (*Homo sapiens* chromosome 11) (MER023159), cathepsin V (MER004437), cathepsin X (MER004508), cathepsin F (MER004980), cathepsin L (MER000622), cathepsin S (MER000633), cathepsin O (MER001690), cathepsin K (MER000644), cathepsin W (MER003756), cathepsin H (MER000629), cathepsin B (MER000686), dipeptidyl-peptidase I (MER001937), bleomycin hydrolase (animal) (MER002481), tubulointerstitial nephritis antigen (MER016137), tubulointerstitial nephritis antigen-related protein (MER021799), cathepsin L-like pseudogene 1 (*Homo sapiens*) (MER002789), cathepsin B-like pseudogene (chromosome 4, *Homo sapiens*) (MER029469), cathepsin B-like pseudogene (chromosome 1, *Homo sapiens*) (MER029457), CTSLL2 g.p. (*Homo sapiens*) (MER005210), CTSLL3 g.p. (*Homo sapiens*) (MER005209), calpain-1 (MER000770), calpain-2 (MER000964), calpain-3 (MER001446), calpain-9 (MER004042), calpain-8 (MER021474), calpain-15 (MER004745), calpain-5 (MER002939), calpain-11 (MER005844), calpain-12 (MER029889), calpain-10 (MER013510), calpain-13 (MER020139), calpain-14 (MER029744), Mername-AA253 peptidase (MER005537), calpamodulin (MER000718), hypothetical protein flj40251 (MER003201), ubiquitinyl hydrolase-L1 (MER000832), ubiquitinyl hydrolase-L3 (MER000836), ubiquitinyl hydrolase-BAP1 (MER003989), ubiquitinyl hydrolase-UCH37 (MER005539), ubiquitin-specific peptidase 5 (MER002066), ubiquitin-specific peptidase 6 (MER000863), ubiquitin-specific peptidase 4 (MER001795), ubiquitin-specific peptidase 8 (MER001884), ubiquitin-specific peptidase 13 (MER002627), ubiquitin-specific peptidase 2 (MER004834), ubiquitin-specific peptidase 11 (MER002693), ubiquitin-specific peptidase 14 (MER002667), ubiquitin-specific peptidase 7 (MER002896), ubiquitin-specific peptidase 9X (MER005877), ubiquitin-specific peptidase 10 (MER004439), ubiquitin-specific peptidase 1 (MER004978), ubiquitin-specific peptidase 12 (MER005454), ubiquitin-specific peptidase 16 (MER005493), ubiquitin-specific peptidase 15 (MER005427), ubiquitin-specific peptidase 17 (MER002900), ubiquitin-specific peptidase 19 (MER005428), ubiquitin-specific peptidase 20 (MER005494), ubiquitin-specific peptidase 3 (MER005513), ubiquitin-specific peptidase 9Y (MER004314), ubiquitin-specific peptidase 18 (MER005641), ubiquitin-specific peptidase 21 (MER006258), ubiquitin-specific peptidase 22 (MER012130), ubiquitin-specific peptidase 33 (MER014335), ubiquitin-specific peptidase 29 (MER012093), ubiquitin-specific peptidase 25 (MER011115), ubiquitin-specific peptidase 36 (MER014033), ubiquitin-specific peptidase 32 (MER014290), ubiquitin-specific peptidase 26 (*Homo sapiens*-type) (MER014292), ubiquitin-specific peptidase 24 (MER005706), ubiquitin-specific peptidase 42 (MER011852), ubiquitin-specific peptidase 46 (MER014629), ubiquitin-specific peptidase 37 (MER014633), ubiquitin-specific peptidase 28 (MER014634), ubiquitin-specific peptidase 47 (MER014636), ubiquitin-specific peptidase 38 (MER014637), ubiquitin-specific peptidase 44 (MER014638), ubiquitin-specific peptidase 50 (MER030315), ubiquitin-specific peptidase 35 (MER014646), ubiquitin-specific peptidase 30 (MER014649), Mername-AA091 peptidase (MER014743), ubiquitin-specific peptidase 45 (MER030314), ubiquitin-specific peptidase 51 (MER014769), ubiquitin-specific peptidase 34 (MER014780), ubiquitin-specific peptidase 48 (MER064620), ubiquitin-specific peptidase 40 (MER015483), ubiquitin-specific peptidase 41 (MER045268), ubiquitin-specific peptidase 31 (MER015493), Mername-AA129 peptidase (MER016485), ubiquitin-specific peptidase 49 (MER016486), Mername-AA187 peptidase (MER052579), USP17-like peptidase (MER030192), ubiquitin-specific peptidase 54 (MER028714), ubiquitin-specific peptidase 53 (MER027329), ubiquitin-specific endopeptidase 39 [misleading] (MER064621), Mername-AA090 non-peptidase homologue (MER014739), ubiquitin-specific peptidase [misleading] (MER030140), ubiquitin-specific peptidase 52 [misleading] (MER030317), NEK2 pseudogene (MER014736), C19 pseudogene (*Homo sapiens*: chromosome 5) (MER029972), Mername-AA088 peptidase (MER014750), autophagin-2 (MER013564), autophagin-1 (MER013561), autophagin-3 (MER014316), autophagin-4 (MER064622), Cezanne deubiquitinylating peptidase (MER029042), Cezanne-2 peptidase (MER029044), tumor necrosis factor alpha-induced protein 3 (MER029050), trabid peptidase (MER029052), VCIP135 deubiquitinating peptidase (MER152304), otubain-1 (MER029056), otubain-2 (MER029061), CyID protein (MER030104), UfSP1 peptidase (MER042724), UfSP2 peptidase (MER060306), DUBA deubiquitinylating enzyme (MER086098), KIAA0459 (*Homo sapiens*)-like protein (MER122467), Otud1 protein (MER125457), glycosyltransferase 28 domain containing 1, isoform CRA_c (*Homo sapiens*)-like (MER123606), hin1L g.p. (*Homo sapiens*) (MER139816), ataxin-3 (MER099998), ATXN3L putative peptidase (MER115261), Josephin domain containing 1 (*Homo sapiens*) (MER125334), Josephin domain containing 2 (*Homo sapiens*) (MER124068), YOD1 peptidase (MER116559), legumain (plant alpha form) (MER044591), legumain (MER001800), glycosylphosphatidylinositol:protein transamidase (MER002479), legumain pseudogene (*Homo sapiens*) (MER029741), family C13 unassigned peptidases (MER175813), caspase-1 (MER000850), caspase-3 (MER000853), caspase-7 (MER002705), caspase-6 (MER002708), caspase-2 (MER001644), caspase-4 (MER001938), caspase-5 (MER002240), caspase-8 (MER002849), caspase-9 (MER002707), caspase-10 (MER002579), caspase-14 (MER012083), paracaspase (MER019325), Mername-AA143 peptidase (MER021304), Mername-AA186 peptidase (MER020516), putative caspase (*Homo sapiens*) (MER021463), FLIP protein (MER003026), Mername-AA142 protein (MER021316), caspase-12 pseudogene (*Homo sapiens*) (MER019698), Mername-AA093 caspase pseudogene (MER014766), subfamily C14A non-peptidase homologues (MER185329), subfamily C14A non-peptidase homologues (MER179956), separase (*Homo sapiens*-type) (MER011775), separase-like pseudogene (MER014797), SENP1 peptidase (MER011012), SENP3 peptidase (MER011019), SENP6 peptidase (MER011109), SENP2 peptidase (MER012183), SENP5 peptidase (MER014032), SENP7 peptidase (MER014095), SENP8 peptidase (MER016161), SENP4 peptidase (MER005557), pyroglutamyl-peptidase I (chordate) (MER011032), Mername-AA073 peptidase (MER029978), Sonic hedgehog protein (MER002539), Indian hedgehog protein (MER002538), Desert hedgehog protein (MER012170), dipeptidyl-peptidase III (MER004252), Mername-AA164 protein (MER020410), LOC138971 g.p. (*Homo sapiens*) (MER020074), Atp23 peptidase (MER060642), prenyl peptidase 1 (MER004246), aminopeptidase N (MER000997), aminopeptidase A (MER001012), leukotriene A4 hydrolase (MER001013), pyroglutamyl-peptidase II (MER012221), cytosol alanyl aminopeptidase (MER002746), cystinyl aminopeptidase (MER002060), aminopeptidase B (MER001494), aminopeptidase PILS (MER005331), arginyl aminopeptidase-like 1 (MER012271), leukocyte-derived arginine aminopeptidase (MER002968), aminopeptidase Q (MER052595), aminopeptidase 0 (MER019730), Tata binding protein associated factor (MER026493), angiotensin-converting enzyme peptidase unit 1 (MER004967), angiotensin-converting enzyme peptidase unit 2 (MER001019), angiotensin-converting enzyme-2 (MER011061), Mername-AA153 protein (MER020514), thimet oligopeptidase (MER001737), neurolysin (MER010991), mitochondrial intermediate peptidase (MER003665), Mername-AA154 protein (MER021317), leishmanolysin-2 (MER014492), leishmanolysin-3 (MER180031), matrix metallopeptidase-1 (MER001063), matrix metallopeptidase-8 (MER001084), matrix metallopeptidase-2 (MER001080), matrix metallopeptidase-9 (MER001085), matrix metallopeptidase-3 (MER001068), matrix metallopeptidase-10 (*Homo sapiens*-type) (MER001072), matrix metallopeptidase-11

(MER001075), matrix metallopeptidase-7 (MER001092), matrix metallopeptidase-12 (MER001089), matrix metallopeptidase-13 (MER001411), membrane-type matrix metallopeptidase-1 (MER001077), membrane-type matrix metallopeptidase-2 (MER002383), membrane-type matrix metallopeptidase-3 (MER002384), membrane-type matrix metallopeptidase-4 (MER002595), matrix metallopeptidase-20 (MER003021), matrix metallopeptidase-19 (MER002076), matrix metallopeptidase-23B (MER004766), membrane-type matrix metallopeptidase-5 (MER005638), membrane-type matrix metallopeptidase-6 (MER012071), matrix metallopeptidase-21 (MER006101), matrix metallopeptidase-22 (MER014098), matrix metallopeptidase-26 (MER012072), matrix metallopeptidase-28 (MER013587), matrix metallopeptidase-23A (MER037217), macrophage elastase homologue (chromosome 8, *Homo sapiens*) (MER030035), Mername-AA156 protein (MER021309), matrix metallopeptidase-like 1 (MER045280), subfamily M10A non-peptidase homologues (MER175912), subfamily M10A non-peptidase homologues (MER187997), subfamily M10A non-peptidase homologues (MER187998), subfamily M10A non-peptidase homologues (MER180000), meprin alpha subunit (MER001111), meprin beta subunit (MER005213), procollagen C-peptidase (MER001113), mammalian tolloid-like 1 protein (MER005124), mammalian-type tolloid-like 2 protein (MER005866), ADAMTS9 peptidase (MER012092), ADAMTS14 peptidase (MER016700), ADAMTS15 peptidase (MER017029), ADAMTS16 peptidase (MER015689), ADAMTS17 peptidase (MER016302), ADAMTS18 peptidase (MER016090), ADAMTS19 peptidase (MER015663), ADAMS peptidase (MER003902), ADAM9 peptidase (MER001140), ADAM10 peptidase (MER002382), ADAM12 peptidase (MER005107), ADAM19 peptidase (MER012241), ADAM15 peptidase (MER002386), ADAM17 peptidase (MER003094), ADAM20 peptidase (MER004725), ADAMDEC1 peptidase (MER000743), ADAMTS3 peptidase (MER005100), ADAMTS4 peptidase (MER005101), ADAMTS1 peptidase (MER005546), ADAM28 peptidase (*Homo sapiens*-type) (MER005495), ADAMTS5 peptidase (MER005548), ADAMTS8 peptidase (MER005545), ADAMTS6 peptidase (MER005893), ADAMTS7 peptidase (MER005894), ADAM30 peptidase (MER006268), ADAM21 peptidase (*Homo sapiens*-type) (MER004726), ADAMTS10 peptidase (MER014331), ADAMTS12 peptidase (MER014337), ADAMTS13 peptidase (MER015450), ADAM33 peptidase (MER015143), ovastacin (MER029996), ADAMTS20 peptidase (*Homo sapiens*-type) (MER026906), procollagen I N-peptidase (MER004985), ADAM2 protein (MER003090), ADAM6 protein (MER047044), ADAM7 protein (MER005109), ADAM18 protein (MER012230), ADAM32 protein (MER026938), non-peptidase homologue (*Homo sapiens* chromosome 4) (MER029973), family M12 non-peptidase homologue (*Homo sapiens* chromosome 16) (MER047654), family M12 non-peptidase homologue (*Homo sapiens* chromosome 15) (MER047250), ADAM3B protein (*Homo sapiens*-type) (MER005199), ADAM11 protein (MER001146), ADAM22 protein (MER005102), ADAM23 protein (MER005103), ADAM29 protein (MER006267), protein similar to ADAM21 peptidase preproprotein (*Homo sapiens*) (MER026944), Mername-AA225 peptidase homologue (*Homo sapiens*) (MER047474), putative ADAM pseudogene (chromosome 4, *Homo sapiens*) (MER029975), ADAM3A g.p. (*Homo sapiens*) (MER005200), ADAM1 g.p. (*Homo sapiens*) (MER003912), subfamily M12B non-peptidase homologues (MER188210), subfamily M12B non-peptidase homologues (MER188211), subfamily M12B non-peptidase homologues (MER188212), subfamily M12B non-peptidase homologues (MER188220), neprilysin (MER001050), endothelin-converting enzyme 1 (MER001057), endothelin-converting enzyme 2 (MER004776), DINE peptidase (MER005197), neprilysin-2 (MER013406), Kell blood-group protein (MER001054), PHEX peptidase (MER002062), i-AAA peptidase (MER001246), i-AAA peptidase (MER005755), paraplegin (MER004454), Afg3-like protein 2 (MER005496), Afg3-like protein 1A (MER014306), pappalysin-1 (MER002217), pappalysin-2 (MER014521), farnesylated-protein converting enzyme 1 (MER002646), metalloprotease-related protein-1 (MER030873), aminopeptidase AMZ2 (MER011907), aminopeptidase AMZ1 (MER058242), carboxypeptidase A1 (MER001190), carboxypeptidase A2 (MER001608), carboxypeptidase B (MER001194), carboxypeptidase N (MER001198), carboxypeptidase E (MER001199), carboxypeptidase M (MER001205), carboxypeptidase U (MER001193), carboxypeptidase A3 (MER001187), metallocarboxypeptidase D peptidase unit 1 (MER003781), metallocarboxypeptidase Z (MER003428), metallocarboxypeptidase D peptidase unit 2 (MER004963), carboxypeptidase A4 (MER013421), carboxypeptidase A6 (MER013456), carboxypeptidase A5 (MER017121), metallocarboxypeptidase 0 (MER016044), cytosolic carboxypeptidase-like protein 5 (MER033174), cytosolic carboxypeptidase 3 (MER033176), cytosolic carboxypeptidase 6 (MER033178), cytosolic carboxypeptidase 1 (MER033179), cytosolic carboxypeptidase 2 (MER037713), metallocarboxypeptidase D non-peptidase unit (MER004964), adipocyte-enhancer binding protein 1 (MER003889), carboxypeptidase-like protein X1 (MER013404), carboxypeptidase-like protein X2 (MER078764), cytosolic carboxypeptidase (MER026952), family M14 non-peptidase homologues (MER199530), insulysin (MER001214), mitochondrial processing peptidase beta-subunit (MER004497), nardilysin (MER003883), eupitrilysin (MER004877), mitochondrial processing peptidase non-peptidase alpha subunit (MER001413), ubiquinol-cytochrome c reductase core protein I (MER003543), ubiquinol-cytochrome c reductase core protein II (MER003544), ubiquinol-cytochrome c reductase core protein domain 2 (MER043998), insulysin unit 2 (MER046821), nardilysin unit 2 (MER046874), insulysin unit 3 (MER078753), mitochondrial processing peptidase subunit alpha unit 2 (MER124489), nardilysin unit 3 (MER142856), LOC133083 g.p. (*Homo sapiens*) (MER021876), subfamily M16B non-peptidase homologues (MER188757), leucyl aminopeptidase (animal) (MER003100), Mername-AA040 peptidase (MER003919), leucyl aminopeptidase-1 (*Caenorhabditis*-type) (MER013416), methionyl aminopeptidase 1 (MER001342), methionyl aminopeptidase 2 (MER001728), aminopeptidase P2 (MER004498), Xaa-Pro dipeptidase (eukaryote) (MER001248), aminopeptidase P1 (MER004321), mitochondrial intermediate cleaving peptidase 55 kDa (MER013463), mitochondrial methionyl aminopeptidase (MER014055), Mername-AA020 peptidase homologue (MER010972), proliferation-association protein 1 (MER005497), chromatin-specific transcription elongation factor 140 kDa subunit (MER026495), proliferation-associated protein 1-like (*Homo sapiens* chromosome X) (MER029983), Mername-AA226 peptidase homologue (*Homo sapiens*) (MER056262), Mername-AA227 peptidase homologue (*Homo sapiens*) (MER047299), subfamily M24A non-peptidase homologues (MER179893), aspartyl aminopeptidase (MER003373), Gly-Xaa carboxypeptidase (MER033182), carnosine dipeptidase II (MER014551), carnosine dipeptidase I (MER015142), Mername-AA161 protein (MER021873), aminoacylase (MER001271), glutamate carboxypeptidase II (MER002104), NAALADASE L peptidase (MER005239), glutamate carboxypeptidase III (MER005238), plasma glutamate carboxypeptidase (MER005244), Mername-AA103 peptidase (MER015091), Fxna peptidase (MER029965), transferrin receptor protein (MER002105), transferrin receptor 2 protein (MER005152), glutaminyl cyclise (MER015095), glutamate carboxypeptidase II (*Homo sapiens*)-type non-peptidase homologue (MER026971), nicalin (MER044627), membrane dipeptidase (MER001260), membrane-bound dipeptidase-2 (MER013499), membrane-bound dipeptidase-3 (MER013496), dihydro-orotase (MER005767), dihydropyrimidinase (MER033266), dihydropyrimidinase related protein-1 (MER030143), dihydropyrimidinase related protein-2 (MER030155), dihydropyrimidinase related protein-3 (MER030151), dihydropyrimidinase related protein-4 (MER030149), dihydropyrimidinase related protein-5 (MER030136), hypothetical protein like 5730457F11RIK (MER033184), 1300019j08rik protein (MER033186)), guanine aminohydrolase (MER037714), Kae1 putative peptidase (MER001577), OSGEPL1-like protein (MER013498), S2P peptidase (MER004458), subfamily M23B non-peptidase homologues (MER199845), subfamily M23B non-peptidase homologues (MER199846), subfamily M23B non-peptidase homologues (MER199847), subfamily M23B non-peptidase homologues (MER137320), subfamily M23B non-peptidase homologues (MER201557), subfamily M23B non-peptidase homologues (MER199417), subfamily M23B non-peptidase homologues (MER199418), subfamily M23B non-peptidase homologues (MER199419), subfamily M23B non-peptidase homologues (MER199420), subfamily M23B non-peptidase homologues (MER175932), subfamily M23B non-peptidase homologues (MER199665), Poh1 peptidase (MER020382), Jab1/MPN domain metalloenzyme (MER022057), Mername-AA165 peptidase (MER021865), Brcc36 isopeptidase (MER021890), histone H2A deubiquitinase MYSM1 (MER021887), AMSH deubiquitinating peptidase (MER030146), putative peptidase (*Homo sapiens* chromosome 2) (MER029970), Mername-AA168 protein (MER021886), COP9 signalosome subunit 6 (MER030137), 26S proteasome non-ATPase regulatory subunit 7 (MER030134), eukaryotic translation initiation factor 3 subunit 5 (MER030133), 1FP38 peptidase homologue (MER030132), subfamily M67A non-peptidase homologues (MER191181), subfamily M67A unassigned peptidases (MER191144), granzyme B (*Homo sapiens*-type) (MER000168), testisin (MER005212), tryptase beta (MER000136), kallikrein-related peptidase 5 (MER005544), corin (MER005881), kallikrein-related peptidase 12 (MER006038), DESC1 peptidase (MER006298), tryptase gamma 1 (MER011036), kallikrein-related peptidase 14 (MER011038), hyaluronan-binding peptidase (MER003612), transmembrane peptidase, serine 4 (MER011104), intestinal serine peptidase (rodent) (MER016130), adrenal secretory serine peptidase (MER003734), tryptase delta 1 (*Homo sapiens*) (MER005948), matriptase-3 (MER029902), marapsin (MER006119), tryptase-6 (MER006118), ovochymase-1 domain 1 (MER099182), transmembrane peptidase, serine 3 (MER005926), kallikrein-related peptidase 15 (MER000064), Mername-AA031 peptidase (MER014054), TMPRSS13 peptidase (MER014226), Mername-AA038 peptidase (MER062848), Mername-AA204 peptidase (MER029980), cationic trypsin (*Homo sapiens*-type) (MER000020), elastase-2 (MER000118), mannan-binding lectin-associated serine peptidase-3 (MER031968), cathepsin G (MER000082), myeloblastin (MER000170), granzyme A (MER001379), granzyme M (MER001541), chymase (*Homo sapiens*-type) (MER000123), tryptase alpha (MER000135), granzyme K (MER001936), granzyme H (MER000166), chymotrypsin B (MER000001), elastase-1 (MER003733), pancreatic endopeptidase E (MER000149), pancreatic elastase II (MER000146), enteropeptidase (MER002068), chymotrypsin C (MER000761), prostasin (MER002460), kallikrein 1 (MER000093), kallikrein-related peptidase 2 (MER000094), kallikrein-related peptidase 3 (MER000115), mesotrypsin (MER000022), complement component C1r-like peptidase (MER016352), complement factor D (MER000130), complement component activated C1r (MER000238), complement component activated C1s (MER000239), complement component C2a (MER000231), complement factor B (MER000229), mannan-binding lectin-associated serine peptidase 1 (MER000244), complement factor I (MER000228), pancreatic endopeptidase E form B (MER000150), pancreatic elastase IIB (MER000147), coagulation factor XIIa (MER000187), plasma kallikrein (MER000203) coagulation factor Xia (MER000210), coagulation factor IXa (MER000216), coagulation factor Vila (MER000215), coagulation factor Xa (MER000212), thrombin (MER000188), protein C (activated) (MER000222), acrosin (MER000078), hepsin (MER000156), hepatocyte growth factor activator (MER000186), mannan-binding lectin-associated serine peptidase 2 (MER002758), u-plasminogen activator (MER000195), t-plasminogen activator (MER000192), plasmin (MER000175), kallikrein-related peptidase 6 (MER002580), neurotrypsin (MER004171), kallikrein-related peptidase 8 (MER005400), kallikrein-related peptidase 10 (MER003645), epitheliasin (MER003736), kallikrein-related peptidase 4 (MER005266), prosemin (MER004214), chymopasin (MER001503), kallikrein-related peptidase 11 (MER004861), kallikrein-related peptidase 11 (MER216142), trypsin-2 type A (MER000021), HtrA1 peptidase (*Homo sapiens*-type) (MER002577), HtrA2 peptidase (MER208413), HtrA2 peptidase (MER004093), HtrA3 peptidase (MER014795), HtrA4 peptidase (MER016351), Tysnd1 peptidase (MER050461), TMPRSS12 peptidase (MER017085), HAT-like putative peptidase 2 (MER021884), trypsin C (MER021898), kallikrein-related peptidase 7 (MER002001), matriptase (MER003735), kallikrein-related peptidase 13 (MER005269), kallikrein-related peptidase 9 (MER005270), matriptase-2 (MER005278), umbelical vein peptidase (MER005421), LCLP peptidase (MER001900), spinesin (MER014385), marapsin-2 (MER021929), complement factor D-like putative peptidase (MER056164), ovochymase-2 (MER022410), HAT-like 4 peptidase (MER044589), ovochymase 1 domain 1 (MER022412), epidermis-specific SP-like putative peptidase (MER029900), testis serine peptidase 5 (MER029901), Mername-AA258 peptidase (MER000285), polyserase-IA unit 1 (MER030879), polyserase-IA unit 2 (MER030880), testis serine peptidase 2 (human-type) (MER033187), hypothetical acrosin-like peptidase (*Homo sapiens*) (MER033253), HAT-like 5 peptidase (MER028215), polyserase-3 unit 1 (MER061763), polyserase-3 unit 2 (MER061748), peptidase similar to tryptophan/serine protease (MER056263), polyserase-2 unit 1 (MER061777), Mername-AA123 peptidase (MER021930), HAT-like 2 peptidase (MER099184), hCG2041452-like protein (MER099172), hCG22067 (*Homo sapiens*)

(MER099169), brain-rescue-factor-1 (*Homo sapiens*) (MER098873), hCG2041108 (*Homo sapiens*) (MER099173), polyserase-2 unit 2 (MER061760), polyserase-2 unit 3 (MER065694), Mername-AA201 (peptidase homologue) MER099175, secreted trypsin-like serine peptidase homologue (MER030000), polyserase-1A unit 3 (MER029880), azurocidin (MER000119), haptoglobin-1 (MER000233), haptoglobin-related protein (MER000235), macrophage-stimulating protein (MER001546), hepatocyte growth factor (MER000185), protein Z (MER000227), TESP1 protein (MER047214), LOC136242 protein (MER016132), plasma kallikrein-like protein 4 (MER016346), PRSS35 protein (MER016350), DKFZp586H2123-like protein (MER066474), apolipoprotein (MER000183), psi-KLK1 pseudogene (*Homo sapiens*) (MER033287), tryptase pseudogene I (MER015077), tryptase pseudogene II (MER015078), tryptase pseudogene III (MER015079), subfamily S1A unassigned peptidases (MER216982), subfamily S1A unassigned peptidases (MER216148), amidophosphoribosyltransferase precursor (MER003314), glutamine-fructose-6-phosphate transaminase 1 (MER003322), glutamine:fructose-6-phosphate amidotransferase (MER012158), Mername-AA144 protein (MER021319), asparagine synthetase (MER033254), family C44 non-peptidase homologues (MER159286), family C44 unassigned peptidases (MER185625) family C44 unassigned peptidases (MER185626), secernin 1 (MER045376), secernin 2 (MER064573), secernin 3 (MER064582), acid ceramidase precursor (MER100794), N-acylethanolamine acid amidase precursor (MER141667), proteasome catalytic subunit 1 (MER000556), proteasome catalytic subunit 2 (MER002625), proteasome catalytic subunit 3 (MER002149), proteasome catalytic subunit 1i (MER000552), proteasome catalytic subunit 2i (MER001515), proteasome catalytic subunit 3i (MER000555), proteasome catalytic subunit 5t (MER026203), protein serine kinase c17 (MER026497), proteasome subunit alpha 6 (MER000557), proteasome subunit alpha 2 (MER000550), proteasome subunit alpha 4 (MER000554), proteasome subunit alpha 7 (MER033250), proteasome subunit alpha 5 (MER000558), proteasome subunit alpha 1 (MER000549), proteasome subunit alpha 3 (MER000553), proteasome subunit XAPC7 (MER004372), proteasome subunit beta 3 (MER001710), proteasome subunit beta 2 (MER002676), proteasome subunit beta 1 (MER000551), proteasome subunit beta 4 (MER001711), Mername-AA230 peptidase homologue (*Homo sapiens*) (MER047329), Mername-AA231 pseudogene (*Homo sapiens*) (MER047172), Mername-AA232 pseudogene (*Homo sapiens*) (MER047316), glycosylasparaginase precursor (MER003299), isoaspartyl dipeptidase (threonine type) (MER031622), taspase-1 (MER016969), gamma-glutamyltransferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721), gamma-glutamyltransferase-like protein 3 (MER016970), similar to gamma-glutamyltransferase 1 precursor (*Homo sapiens*) (MER026204), similar to gamma-glutamyltransferase 1 precursor (*Homo sapiens*) (MER026205), Mername-AA211 putative peptidase (MER026207), gamma-glutamyltransferase 6 (MER159283), gamma-glutamyl transpeptidase homologue (chromosome 2, *Homo sapiens*) (MER037241), polycystin-1 (MER126824), KIAA1879 protein (MER159329), polycystic kidney disease 1-like 3 (MER172554), gamma-glutamyl hydrolase (MER002963), guanine 5"-monophosphate synthetase (MER043387), carbamoyl-phosphate synthase (*Homo sapiens*-type) (MER078640), dihydro-orotase (N-terminal unit) (*Homo sapiens*-type) (MER060647) DJ-1 putative peptidase (MER003390), Mername-AA100 putative peptidase (MER014802), Mername-AA101 non-peptidase homologue (MER014803), KIAA0361 protein (*Homo sapiens*-type) (MER042827), FI134283 protein (*Homo sapiens*) (MER044553), non-peptidase homologue chromosome 21 open reading frame 33 (*Homo sapiens*) (MER160094), family C56 non-peptidase homologues (MER177016), family C56 non-peptidase homologues (MER176613), family C56 non-peptidase homologues (MER176918), EGF-like module containing mucin-like hormone receptor-like 2 (MER037230), CD97 antigen (human type) (MER037286), EGF-like module containing mucin-like hormone receptor-like 3 (MER037288), EGF-like module containing mucin-like hormone receptor-like 1 (MER037278), EGF-like module containing mucin-like hormone receptor-like 4 (MER037294), cadherin EGF LAG seven-pass G-type receptor 2 precursor (*Homo sapiens*) (MER045397), Gpr64 (*Mus musculus*)-type protein (MER123205), GPR56 (*Homo sapiens*)-type protein (MER122057), latrophilin 2 (MER122199), latrophilin-1 (MER126380), latrophilin 3 (MER124612), protocadherin Flamingo 2 (MER124239), ETL protein (MER126267), G protein-coupled receptor 112 (MER126114), seven transmembrane helix receptor (MER125448), Gpr114 protein (MER159320), GPR126 vascular inducible G protein-coupled receptor (MER140015), GPR125 (*Homo sapiens*)-type protein (MER159279), GPR116 (*Homo sapiens*)-type G-protein coupled receptor (MER159280), GPR128 (*Homo sapiens*)-type G-protein coupled receptor (MER162015), GPR133 (*Homo sapiens*)-type protein (MER159334), GPR110 G-protein coupled receptor (MER159277), GPR97 protein (MER159322), KPG_006 protein (MER161773), KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripeptidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPLA protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219

(MER033212), hypothetical protein flj37464 (MER033240), hypothetical protein flj33678 (MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein FLJ22408 (MER031608), CGI-58 putative peptidase (MER030163), Williams-Beuren syndrome critical region protein 21 epoxide hydrolase (MER031610), epoxide hydrolase (MER031612), hypothetical protein flj22408 (epoxide hydrolase) (MER031617), monoglyceride lipase (MER033247), hypothetical protein (MER033249), valacyclovir hydrolase (MER033259), Ccg1-interacting factor b (MER210738), glycosylasparaginase precursor (MER003299), isoaspartyl dipeptidase (threonine type) (MER031622). taspase-1 (MER016969), gamma-glutamyltransferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721). gamma-glutamyltransferase-like protein 3 (MER016970). similar to gamma-glutamyltransferase 1 precursor (*Homo sapiens*) (MER026204). similar to gamma-glutamyltransferase 1 precursor (*Homo sapiens*) (MER026205). Mername-AA211 putative peptidase (MER026207). gamma-glutamyltransferase 6 (MER159283). gamma-glutamyl transpeptidase homologue (chromosome 2, *Homo sapiens*) (MER037241). polycystin-1 (MER126824), KIAA1879 protein (MER159329). polycystic kidney disease 1-like 3 (MER172554). gamma-glutamyl hydrolase (MER002963). guanine 5"-monophosphate synthetase (MER043387). carbamoyl-phosphate synthase (*Homo sapiens*-type) (MER078640). dihydro-orotase (N-terminal unit) (*Homo sapiens*-type) (MER060647). DJ-1 putative peptidase (MER003390). Mername-AA100 putative peptidase (MER014802). Mername-AA101 non-peptidase homologue (MER014803). KIAA0361 protein (*Homo sapiens*-type) (MER042827). FLJ34283 protein (*Homo sapiens*) (MER044553). non-peptidase homologue chromosome 21 open reading frame 33 (*Homo sapiens*) (MER160094). family C56 non-peptidase homologues (MER177016), family C56 non-peptidase homologues (MER176613). family C56 non-peptidase homologues (MER176918). EGF-like module containing mucin-like hormone receptor-like 2 (MER037230). CD97 antigen (human type) (MER037286). EGF-like module containing mucin-like hormone receptor-like 3 (MER037288). EGF-like module containing mucin-like hormone receptor-like 1 (MER037278). EGF-like module containing mucin-like hormone receptor-like 4 (MER037294). cadherin EGF LAG seven-pass G-type receptor 2 precursor (*Homo sapiens*) (MER045397), Gpr64 (*Mus musculus*)-type protein (MER123205). GPR56 (*Homo sapiens*)-type protein (MER122057). latrophilin 2 (MER122199). latrophilin-1 (MER126380). latrophilin 3 (MER124612). protocadherin Flamingo 2 (MER124239). ETL protein (MER126267). G protein-coupled receptor 112 (MER126114). seven transmembrane helix receptor (MER125448). Gpr114 protein (MER159320). GPR126 vascular inducible G protein-coupled receptor (MER140015). GPR125 (*Homo sapiens*)-type protein (MER159279). GPR116 (*Homo sapiens*)-type G-protein coupled receptor (MER159280). GPR128 (*Homo sapiens*)-type G-protein coupled receptor (MER162015). GPR133 (*Homo sapiens*)-type protein (MER159334) GPR110 G-protein coupled receptor (MER159277), GPR97 protein (MER159322), KPG_006 protein (MER161773) KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripetidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPL A protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219 (MER033212), hypothetical protein flj37464 (MER033240), hypothetical protein flj33678

(MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein FLJ22408 (MER031608), CGI-58 putative peptidase (MER030163), Williams-Beuren syndrome critical region protein 21 epoxide hydrolase (MER031610), epoxide hydrolase (MER031612), hypothetical protein flj22408 (epoxide hydrolase) (MER031617), monoglyceride lipase (MER033247), hypothetical protein (MER033249), valacyclovir hydrolase (MER033259), Ccg1-interacting factor b (MER210738).

It will be appreciated that for a given unwanted cell type, the skilled person can readily determine an appropriate one or more protease cleavage sites to use, for example by consulting scientific literature to determine which proteases are overexpressed by that cell type. Oncomine (https://www.oncomine.org) is an online cancer gene expression database, and so when the molecule of the invention is for treating cancer, the skilled person may search the Oncomine database to identify a particular one or more protease cleavage sites that will be appropriate for treating a given cancer type. Alternative databases include European Bioinformatic Institute (http://www.ebi.ac.uk) in particular (http://www.ebi.ac.uk/gxa). Protease databases include PMAP (http://www.proteolysis.org), ExPASy Peptide Cutter (http://ca.expasy.org/tools/peptide cutter) and PMAP.Cut DB (http://cutdb.burnham.org).

It is noted that it may be desirable to screen a library of peptides incorporating multiple potential cleavage sites and evaluating the optimal cleavage site for a given unwanted cell (eg tumour). Such peptides may be useful as linkers, for example, to join the further moiety to one or more masking moieties, or to promote a particular conformation of the further moiety so as to mask T cell binding region of the further moiety (see embodiment exemplified by FIG. 1).

TABLE 4

Matrix showing preferred protease cleavage sites for treating particular tumours

| Protease | | Substrate | Breast | Ovarian | Endo-metrial | Cervical | Bladder | Renal | Melanoma | Lung-NSLC | Lung-SLC | Prostate |
|---|---|---|---|---|---|---|---|---|---|---|---|---|
| Serine | | | | | | | | | | | | |
| urokinase-type plasminogen activator | uPA | CPGR-VVGG (SEQ ID No: 1) | | | • | • | • | | • | • | | • |
| | tPA | CPGR-VVGG (SEQ ID No: 1) | • | | | | | | | | | |
| | Cathepsin A | | | | | | | | | | | |
| | Cathepsin G | | | | | | | | | | | |
| | Plasmin | GGR-X (SEQ ID No: 2) | | | | | | | | | | |
| | C1s | YLGR-SYKV (SEQ ID No: 3) or MQLGR-X (SEQ ID No: 4) | | | | | | | • | | | |
| | MASP2 | SLGR-KIQI (SEQ ID No: 5) | | | | | | | | | | |
| | Thrombin | LVPRGS (SEQ ID No: 6) | | | | | | | | | | |
| | Trypsin | XXXR-X (SEQ ID No: 7) | | | | | | | | | | |
| | Chymotrypsin | | | | | | | | | | | |
| | Elastase 1 | | | | | | | | | | | |
| Leucocyte/Neut Elastase | Elastase 2 | AAPV-X (SEQ ID No: 8) | | | | | | | | | | |
| Leucocyte/Neut Elastase | Elastase 2 | AAPV-X (SEQ ID No: 8) | | | | | | | | | | |
| MT-SP1/ST14 | Matriptase | KQLR-VVNG (SEQ ID No: 9) or KQSR-KFVP (SEQ ID No: 10) (SEQ ID No: 11) | • | • | | | | | | | | • |
| MT-SP2 | Matriptase2 | | • | | | | | | | | | |
| TMPRSS1 | Hepsin | | | | | | | | | | | |
| | TMPRSS2 | GGR-X (SEQ ID No: 2) | | | | | | • | | | | |
| | TMPRSS3 | | | | | | | | | | | |
| | TMPRSS4 | | | | | | | | | | | • • |

TABLE 4-continued

Matrix showing preferred protease cleavage sites for treating particular tumours

| Protease class | Protease | Cleavage site |
|---|---|---|
| | PSA | SSKYQ (SEQ ID No: 12) or HSSKLQL (SEQ ID No: 13) |
| | Leucocyte/Neut Elastase 2 | AAPV-X (SEQ ID No: 8) |
| | MT-SP1/ST14 Matriptase | KQLR-WNG (SEQ ID No: 9) |
| | MT-SP2 Matriptase2 | |
| | TMPRSS1 Hepsin | |
| | TMPRSS2 | GGR-X (SEQ ID No: 2) |
| | TMPRSS3 | |
| | TMPRSS4 | |
| | PSA Prostate Specific Antigen | SSKYQ (SEQ ID No: 12) or HSSKLQL (SEQ ID No: 13) |
| Cysteine | Cathepsin B | GGGG-F (SEQ ID No: 14) |
| | Cathepsin L | |
| | Cathepsin F | |
| | Cathepsin H | |
| | Cathepsin K | |
| | Cathepsin L1 | |
| | Cathepsin L2 | |
| | Cathepsin O | |
| | Cathepsin W | |
| | Cathepsin S | |
| | Cathepsin Z (or X) | |
| Aspartic | Cathepsin D | |
| | Cathepsin E | |
| Metallo | | |
| Collagenase 1 | MMP1 | PLG-LLG (SEQ ID No: 15) |

TABLE 4-continued

Matrix showing preferred protease cleavage sites for treating particular tumours

| | | | | | | | | | | | | | | |
|---|---|---|---|---|---|---|---|---|---|---|---|---|---|---|
| Gelatinase A | MMP2 | PQG-IAGQ (SEQ ID No: 16) or PVGLIG (SEQ ID No: 17) | • | • | • | • | • | | • | • • | • | • • | • • | • • |
| Stromelysin | MMP3 | | | | | | | | | | | | | |
| | MMP4 | | | | | | | | | | | | | |
| | MMP5 | | | | | | | | | | | | | |
| | MMP6 | | | | | | | | | | | | | |
| Matrilysin | MMP7 | | | | • | | | | | | | | | |
| Collagenase 2 | MMP8 | | | | | | | | | | | | | |
| Gelatinase B | MMP9 | PQG-IAGQ (SEQ ID No: 16) or PRA-LY (SEQ ID No: 18) | • | • | • | • | | | • | • | • | • • | • | • |
| | MMP10 | | | | | | | | | | | | | |
| | MMP11 | | | | | | | | | | | | | |
| | MMP12 | | | | | | | | | | | | | |
| | MMP13 | | | | | | | | | | | | | |
| | MMP14 | PRH-LR (SEQ ID No: 19) | • • | • | | • | | | | | | • • • | | |
| | MMP15 | | | | | | | | | | | | | |
| | MMP16 | | | | | | | | | | | | | |
| | MMP17 | | | | | | | | | | | | | |
| | MMP18 | | | | | | | | | | | | | |
| | MMP19 | | | | | | | | | | | | | |
| | MMP20 | | | | | | | | | | | | | |
| | MMP21 | | | | | | | | | | | | | |
| | MMP23A | | | | | | | | | | | | | |
| | MMP23B | | | | | | | | | | | | | |
| | MMP24 | | | | | | | | | | | | | |
| | MMP25 | | | | | | | | | | | | | |
| | MMP26 | | | | | | | | | | | | | |
| | MMP27 | | | | | | | | | | | | | |
| | MMP28 | | | | | | | | | | | | | |
| | ADAM2 | | | | | | | | | | | | | |
| | ADAM7 | | | | | | | | | | | | | |
| | ADAM8 | | | | | | | | | | | | | |
| | ADAM9 | | | | | | | | | | | | | |
| | ADAM10 | | | | | | | | | | | | | |
| | ADAM11 | | | | | | | | | | | | | |
| | ADAM12 | | | | | | • | | | | | | | |
| | ADAM15 | | | | | • | | | | | | | | |
| | ADAM17 | | | | | | | | | | | | | |
| | ADAM18/27 | | | | | | | | | | | | | |
| | ADAM19 | | | | | | | | | | | | | |

TABLE 4-continued

Matrix showing preferred protease cleavage sites for treating particular tumours

| Protease | Substrate | Testicular | Thyroid | Brain | Oesophageal | Gastric | Pancreatic | Colorectal | Liver |
|---|---|---|---|---|---|---|---|---|---|
| ADAM20 | | | | | | | | | |
| ADAM21/31 | | | | | | | | | |
| ADAM22 | | | | | | | | | |
| ADAM23 | | | | | | | | | |
| ADAM28 | | • | | | | | | | |
| ADAM29 | | | | • | | | | | |
| ADAM30 | | | | | | | | | |
| ADAM33 | | | | | | | | | |
| ADAMTS1 | | | | | | | | | |
| ADAMTS2 | | | | | | | | | |
| ADAMTS3 | | | | | | | | | |
| ADAMTS4 | | | | | | | | | |
| ADAMTS5/11 | | | | | | | | | |
| ADAMTS6 | | | | | | | | | |
| ADAMTS7 | | | | | | | | | |
| ADAMTS8 | | | | | | | | | |
| ADAMTS9 | | | | | | | | | |
| ADAMTS10 | | | | | | | | | |
| ADAMTS12 | | | | | | | | | |
| ADAMTS13 | | | | | | | | | |
| ADAMTS14 | | | | | | | | | |
| ADAMTS15 | | • | | | | | | | |
| ADAMTS16 | | | | | | | | | |
| ADAMTS17 | | | | | | | | | |
| ADAMTS18 | | | | | | | | | |
| ADAMTS19 | | | | | | | | | |
| ADAMTS20 | | | | | | | | | |
| Serine | | | | | | | | | |
| urokinase-type plasminogen activator | uPA | CPGR-VVGG (SEQ ID No: 1) | | | | • | • | • | • |
| | tPA | CPGR-VVGG (SEQ ID No: 1) | | | | | | | |
| | Cathepsin A | | | | | | | | |
| | Cathepsin G | | | | | | | | |
| | Plasmin | GGR-X (SEQ ID No: 2) | | | | | | | |
| | C1s | YLGR-SYKV (SEQ ID No: 3) or MQLGR-X (SEQ ID No: 4) | | | | | | | |
| | MASP2 | SLGR-KIQI (SEQ ID No: 5) | | | | | | | |
| | Thrombin | LVPRGS (SEQ ID No: 6) | | | | | | | |

TABLE 4-continued

Matrix showing preferred protease cleavage sites for treating particular tumours

| | | | | | | | |
|---|---|---|---|---|---|---|---|
| | Trypsin | XXXR-X (SEQ ID No: 7) | | | | | |
| | Chymotrypsin Elastase 1 | | | | | | |
| Leucocyte/Neut Elastase | Elastase 2 | AAPV-X (SEQ ID No: 8) | | | | | |
| Leucocyte/Neut Elastase | Elastase 2 | AAPV-X (SEQ ID No: 8) | | | | | |
| MT-SP1/ST14 | Matriptase | KQLR-VVNG (SEQ ID No: 9) or KQSR- (SEQ ID No: 10) KFVP (SEQ ID No: 11) | • | | | | |
| MT-SP2 | Matriptase2 | | | | | | |
| TMPRSS1 | Hepsin TMPRSS2 | GGR-X (SEQ ID No: 2) | | • | | | |
| | TMPRSS3 TMPRSS4 | | | | | | |
| PSA | Prostate Specific Antigen | SSKYQ (SEQ ID No: 12) or HSSKLQL (SEQ ID No: 13) | | | • | | |
| Leucocyte/Neut Elastase | Elastase 2 | AAPV-X (SEQ ID No: 8) | | | | • | |
| MT-SP1/ST14 | Matriptase | KQLR-WNG (SEQ ID No: 9) | | | | | • |
| MT-SP2 | Matriptase2 | | | | | | |
| TMPRSS1 | Hepsin TMPRSS2 | GGR-X (SEQ ID No: 2) | | | | • | |
| | TMPRSS3 TMPRSS4 | | | | | | |
| PSA | Prostate Specific Antigen | SSKYQ (SEQ ID No: 12) or HSSKLQL (SEQ ID No: 13) | | | | | • |

TABLE 4-continued

Matrix showing preferred protease cleavage sites for treating particular tumours

| Class | Protease | Sequence | | | | | | | | |
|---|---|---|---|---|---|---|---|---|---|---|
| Cysteine | Cathepsin B | GGGG-F (SEQ ID No: 14) | | | | | • | | | |
| | Cathepsin L | | | | | | | | | |
| | Cathepsin F | | | | | | | | | |
| | Cathepsin H | | | | | | | | | |
| | Cathepsin K | | | | | | | | | |
| | Cathepsin L1 | | | | | | | | | |
| | Cathepsin L2 | | | | | | | | | |
| | Cathepsin O | | | | | | | | | |
| | Cathepsin W | | | | | | | | | |
| | Cathepsin S | | | | | | | | | |
| | Cathepsin Z (or X) | | | | | | | | | |
| Aspartic | Cathepsin D | | | | | • | | | | |
| | Cathepsin E | | | | | | | | | |
| Metallo | | | | | | | | | | |
| Collagenase 1 | MMP1 | PLG-LLG (SEQ ID No: 15) | | | | • | | | | |
| Gelatinase A | MMP2 | PQG-IAGQ (SEQ ID No: 16) or PVGLIG (SEQ ID No: 17) | | | • | • | • | | | |
| Stromelysin | MMP3 | | | | | | | | | |
| | MMP4 | | | | | | | | | |
| | MMP5 | | | | | | | | | |
| | MMP6 | | | | | | | | | |
| Matrilysin | MMP7 | | | | | • | | • | | • |
| Collagenase 2 | MMP8 | | | | | | | | | |
| Gelatinase B | MMP9 | PQG-IAGQ (SEQ ID No: 16) or PRA-LY (SEQ ID No: 18) | | | • | • | | | | |
| | MMP10 | | | | | | | | | |
| | MMP11 | | | | | | | | | |
| | MMP12 | | | | | | | | | |
| | MMP13 | | | | | | | | | |
| | MMP14 | PRH-LR (SEQ ID No: 19) | | | • | • | | • | | • |

TABLE 4-continued

Matrix showing preferred protease cleavage sites for treating particular tumours

| Protease | | | | | | | | | | |
|---|---|---|---|---|---|---|---|---|---|---|
| MMP15 | | | | | | | | | | |
| MMP16 | | | | | | | | | | |
| MMP17 | | | | | | | | | | |
| MMP18 | | | | | | | | | | |
| MMP19 | | | | | | | | | | |
| MMP20 | | | | | | | | | | |
| MMP21 | | | | | | | | | | |
| MMP23A | | | | | | | | | | |
| MMP23B | | | | | | | | • | | |
| MMP24 | | | | | | | | | | |
| MMP25 | | | | | | | | | | |
| MMP26 | | | | | | | | | | |
| MMP27 | | | | | | | | | | |
| MMP28 | | | | | | | | | | |
| ADAM2 | | | | | | • | | | | |
| ADAM7 | | | | | | | | | | |
| ADAM8 | | | | | | | | | | |
| ADAM9 | | | | | | | | | | |
| ADAM10 | | | | • | | | | • | • • | |
| ADAM11 | | | | | • | | | | | |
| ADAM12 | | | | | | | | | | |
| ADAM15 | | | • | | | • | | • | • • | |
| ADAM17 | | | | | • • | | | • | | |
| ADAM18/27 | | | | | | | | | | |
| ADAM19 | | | | | | | | | | |
| ADAM20 | | | | | | | | | | |
| ADAM21/31 | | | | | | • | | • | | |
| ADAM22 | | | | | | | | | | |
| ADAM23 | | | | | | | | | | |
| ADAM28 | | | | | | | | | | |
| ADAM29 | | | | | | | | | | |
| ADAM30 | | | | | | | | | | |
| ADAM33 | | | | | | | | | | |
| ADAMTS1 | | | | | | | | | | |
| ADAMTS2 | | | | | | | | | | |
| ADAMTS3 | | | | | | | | | | |
| ADAMTS4 | | | | | | | | | | |
| ADAMTS5/11 | | | | | | | | | | |
| ADAMTS6 | | | | | | | | | | |
| ADAMTS7 | | | | | | | | | | |
| ADAMTS8 | | | | | | | | | | • |
| ADAMTS9 | | | | | | | | | | |
| ADAMTS10 | | | | | | | | | | |
| ADAMTS12 | | | | | | | | | | |
| ADAMTS13 | | | | | | | | | | |
| ADAMTS14 | | | | | | | | | | |
| ADAMTS15 | | | | | | | | | | |
| ADAMTS16 | | | | | | | | | | |
| ADAMTS17 | | | | | | | | | | |
| ADAMTS18 | | | | | | | | | | |

TABLE 4-continued

Matrix showing preferred protease cleavage sites for treating particular tumours

| Protease | Substrate | Leukaemia | Myeloma | NHL | Hodgkin's | AML | ALL | CLL |
|---|---|---|---|---|---|---|---|---|
| ADAMTS19 |  |  |  |  |  |  |  |  |
| ADAMTS20 |  |  |  |  |  |  |  |  |
| Serine |  |  |  |  |  |  |  |  |
| urokinase-type plasminogen activator | uPA CPGR-VVGG (SEQ ID NO: 1) |  | • | • | • | • | • | • |
| tPA | CPGR-VVGG (SEQ ID NO: 1) |  |  |  |  |  |  |  |
| Cathepsin A |  |  |  |  |  |  |  |  |
| Cathepsin G |  |  |  |  |  |  |  |  |
| Plasmin | GGR-X (SEQ ID NO: 2) |  |  |  |  |  |  |  |
| C1s | YLGR-SYKV (SEQ ID NO: 3) or MQLGR-X (SEQ ID NO: 4) |  |  |  |  |  |  |  |
| MASP2 | SLGR-KIQI (SEQ ID NO: 5) |  |  |  |  |  |  |  |
| Thrombin | LVPRGS (SEQ ID NO: 6) |  |  |  |  |  |  |  |
| Trypsin | XXXR-X (SEQ ID NO: 7) |  |  |  |  |  |  |  |
| Chymotrypsin |  |  |  |  |  |  |  |  |
| Elastase 1 |  |  |  |  |  |  |  |  |
| Leucocyte/Neut Elastase | Elastase 2 AAPV-X (SEQ ID NO: 8) |  |  |  |  |  |  |  |
| Leucocyte/Neut Elastase | Elastase 2 AAPV-X (SEQ ID NO: 8) |  |  |  |  |  |  |  |
| MT-SP1/ST14 | Matriptase KQLR-VVNG (SEQ ID NO: 9) or KQSR- (SEQ ID NO: 10) KFVP (SEQ ID NO: 11) |  |  |  |  |  |  |  |
| MT-SP2 | Matriptase2 |  |  |  |  |  |  |  |
| TMPRSS1 | Hepsin |  |  |  |  |  |  |  |
| TMPRSS2 | GGR-X (SEQ ID NO: 2) |  |  |  |  |  |  |  |
| TMPRSS3 |  |  |  |  |  |  |  |  |
| TMPRSS4 |  |  |  |  |  |  |  |  |

TABLE 4-continued

Matrix showing preferred protease cleavage sites for treating particular tumours

| | | | |
|---|---|---|---|
| | PSA | Prostate Specific Antigen | SSKYQ (SEQ ID No: 12) or HSSKLQL (SEQ ID No: 13) |
| | Leucocyte/Neut Elastase | Elastase 2 | AAPV-X (SEQ ID No: 8) |
| | MT-SP1/ST14 | Matriptase | KQLR-WNG (SEQ ID No: 9) |
| | MT-SP2 | Matriptase2 | |
| | TMPRSS1 | Hepsin TMPRSS2 | GGR-X (SEQ ID No: 2) |
| | | TMPRSS3 TMPRSS4 | |
| | PSA | Prostate Specific Antigen | SSKYQ (SEQ ID No: 12) or HSSKLQL (SEQ ID No: 13) |
| Cysteine | | Cathepsin B | GGGG-F (SEQ ID No: 14) |
| | | Cathepsin L | |
| | | Cathepsin F | |
| | | Cathepsin H | |
| | | Cathepsin K | |
| | | Cathepsin L1 | |
| | | Cathepsin L2 | |
| | | Cathepsin O | |
| | | Cathepsin W | |
| | | Cathepsin S | |
| | | Cathepsin Z (or X) | |
| Aspartic | | Cathepsin D | |
| | | Cathepsin E | |
| Metallo | | | |
| Collagenase 1 | MMP1 | | PLG-LLG (SEQ ID No: 15) | PMA Activated U937 and MCF7 |

TABLE 4-continued

Matrix showing preferred protease cleavage sites for treating particular tumours

| | | | | |
|---|---|---|---|---|
| Gelatinase A | MMP2 | PQG-IAGQ (SEQ ID No: 16) or PVGLIG (SEQ ID No: 17) | • | cells, MDA-MB231 Colo205, HT29 |
| Stromelysin | MMP3 | | | |
| | MMP4 | | | |
| | MMP5 | | | |
| | MMP6 | | | |
| Matrilysin | MMP7 | | • | |
| Collagenase 2 | MMP8 | | | |
| Gelatinase B | MMP9 | PQG-IAGQ (SEQ ID No: 16) or PRA-LY (SEQ ID No: 18) | • | MCF7, PC3 |
| | MMP10 | PRH-LR (SEQ ID No: 19) | | |
| | MMP11 | | | |
| | MMP12 | | | |
| | MMP13 | | | |
| | MMP14 | | | |
| | MMP15 | | | |
| | MMP16 | | | |
| | MMP17 | | | |
| | MMP18 | | | |
| | MMP19 | | | |
| | MMP20 | | | |
| | MMP21 | | | |
| | MMP23A | | | |
| | MMP23B | | | |
| | MMP24 | | | |
| | MMP25 | | | |
| | MMP26 | | | |
| | MMP27 | | | |
| | MMP28 | | | |
| | ADAM2 | | | |
| | ADAM7 | | | |
| | ADAM8 | | | |
| | ADAM9 | | | |
| | ADAM10 | | • | THP-1, HL-60 |
| | ADAM11 | | | |
| | ADAM12 | | | |
| | ADAM15 | | | |

TABLE 4-continued

Matrix showing preferred protease cleavage sites for treating particular tumours

| Protease | Tumours |
|---|---|
| ADAM17 | LNCaP, MDA-MB231, MCF7 express ADAM17, Colo205 express barely any |
| ADAM18/27 | |
| ADAM19 | |
| ADAM20 | |
| ADAM21/31 | |
| ADAM22 | |
| ADAM23 | |
| ADAM28 | |
| ADAM29 | |
| ADAM30 | |
| ADAM33 | |
| ADAMTS1 | |
| ADAMTS2 | |
| ADAMTS3 | |
| ADAMTS4 | |
| ADAMTS5/11 | |
| ADAMTS6 | |
| ADAMTS7 | |
| ADAMTS8 | |
| ADAMTS9 | |
| ADAMTS10 | |
| ADAMTS12 | |
| ADAMTS13 | |
| ADAMTS14 | |
| ADAMTS15 | |
| ADAMTS16 | |
| ADAMTS17 | |
| ADAMTS18 | |
| ADAMTS19 | |
| ADAMTS20 | |

TABLE 5

Tumour sites in which ADAM overexpression has been reported

| Protein | Tumour expression |
| --- | --- |
| ADAM8 | Brain, kidney, lung, pancreas |
| ADAM9 | Breast, gastric, liver, lung, pancreas, prostate |
| ADAM10 | Colon, gastric, leukaemia, prostate, uterus, ovary |
| ADAM12 | Bladder, brain, breast, colon, gastric, liver |
| ADAM15 | Breast, gastric, lung, prostate |
| ADAM17 | Brain, breast, colon, gastric, kidney, liver, lung, ovary, pancreas, prostate |
| ADAM19 | Brain, kidney |
| ADAM28 | Breast, kidney, lung |

A number of the proteolytic ADAMs (a disintegrin and metalloproteinase) have been detected in cancers and mRNA or protein levels have been found to be upregulated relative to normal tissue (adapted from Nature Reviews Cancer 8, 932-941 (December 2008) 1 doi:10.1038/nrc2459).

In one embodiment, the protease may be an esterase.

Other cleavage sites include linkages which are labile under certain conditions in the vicinity of unwanted cells (eg tumour microenvironment). For example, the one or more cleavage sites may comprise disulphide bonds, which can be reduced in the hypoxic tumour microenvironment, or may comprise pH sensitive moieties that break in acidic conditions. It will be understood, however, that the one or more cleavage sites must be selectively cleavable in the vicinity of the unwanted cells and so such linkages must be more labile and preferably only labile in the vicinity of unwanted cells compared to in the vicinity of wanted cells.

Alternatively, the one or more cleavage sites may comprise nucleic acid (eg DNA or RNA) that is selectively cleavable in the vicinity of unwanted cells (eg by nucleases). Other cleavage sites include phosphate, lipid or disulphide containing moieties that may be cleavable by appropriate enzymes.

Synthesis of Molecule of Invention

Conveniently, the targeting moiety is joined to the further moiety by one or more linkers. Thus, by 'linker' we include the meaning of a chemical moiety that attaches the targeting moiety to the further moiety. Preferably, the linker is a peptide linker. It will be appreciated that such linkers may contain one or more cleavage sites that are selectively cleaved in the vicinity of the unwanted cells so as to unmask the immune cell binding region of the further moiety.

As described above, it is possible for the further moiety to have two or more separate parts. For example, the further moiety may comprise two or more polypeptide domains including immunoglobulin domains of an antibody (e.g. scFv antibody). Such parts may be linked together by one or more linkers. Thus, by 'linker', we also include the meaning of any chemical moiety that attaches the separate parts of a further moiety to each other. Preferably, the linker is a peptide linker. For example, the further moiety of the molecule illustrated in FIG. 1 comprises a VH domain and a VL domain which domains are joined by a linker. These linkers may contain one or more cleavage sites that are selectively cleaved in the vicinity of the unwanted cells so as to unmask the T cell binding region of the further moiety.

Also conveniently, when the molecule comprises one or more masking moieties, these are attached to the targeting moiety and/or further moiety by means of one or more linkers. Thus, by 'linker' we also include the meaning of a chemical moiety that attaches the targeting moiety to a masking moiety and a chemical moiety that attaches the further moiety to a masking moiety. Preferably, the linker is a peptide linker. For example, FIGS. 2 and 3 depict examples of linkers between a further moiety and a masking moiety, and FIG. 4 depicts examples of linkers between a further moiety and a masking moiety, and between a targeting moiety and a masking moiety. Such linkers may also contain one or more cleavage sites that are selectively cleaved in the vicinity of the unwanted cells so as to unmask the T cell binding region of the further moiety Examples of suitable linkers include peptides, polymers, nucleotides, nucleic acids, polysaccharides and lipid organic species (eg polyethylene glycol). Most preferably, however, the linkers described herein are peptide linkers. Generally, the peptide linkers have between 2 and 100 amino acid residues, such as more than or less than 10, 20, 30, 40, 50, 60, 70, 80 and 90 amino acids. Further detail of the preferred length of particular linkers is given below.

It is appreciated that the targeting moiety may either be bound covalently or non-covalently to the further moiety. Likewise, it is appreciated that the targeting moiety and/or further moiety may either be bound covalently or non-covalently to the one or more masking moieties.

Typically, the targeting moiety is covalently bound to the further moiety, and when the molecule comprises one or more masking moieties, the one or more masking moieties are covalently bound to the further moiety and/or targeting moiety.

In one embodiment, the targeting moiety and further moiety are covalently attached by a linker (eg peptide linker). When the molecule comprises one or more masking moieties, the one or more masking moieties may be covalently attached to the further moiety and/or targeting moiety by one or more linkers (eg peptide linkers).

It is appreciated that the targeting moiety, further moiety (including separate parts thereof) and one or more masking moieties do not need to be linked directly to each other, but may be attached via one or more spacer moieties (eg peptides). For example, the targeting moiety may be linked to a chemical moiety (eg peptide) which in turn is linked to the further moiety. Similarly, the further moiety may be linked to one or more chemical moieties (eg peptides) which in turn are linked to one or more respective masking moieties. In one embodiment, such spacer moieties may comprise a cleavage site that is cleavable selectively in the vicinity of the unwanted cells, as discussed above. It will be appreciated that the spacer moiety may serve to prevent steric hindrance and facilitate protease cleavage.

In view of the above, it is appreciated that the invention provides a molecule comprising: (i) a targeting moiety capable of directly or indirectly targeting to unwanted cells, (ii) a further moiety that has a masked immune cell binding region so as to prevent binding of the further moiety to an immune cell, (iii) one or more masking moieties attached to the further moiety and/or targeting moiety which one or more masking moieties act to mask the immune cell binding region of the further moiety, and (iv) one or more cleavable sites between the one or more masking moieties, and the further moiety and/or the targeting moiety, wherein the one or more cleavage sites can be selectively cleaved in the vicinity of the unwanted cells so as to unmask the immune cell binding region.

In a preferred embodiment where the targeting moiety, further moiety and, if present, the one or more masking moieties are covalently attached and where all moieties are peptides or polypeptides, it is appreciated that the component moieties of the molecule may be part of one or more fusion polypeptides that may be encoded by a respective one or more nucleic acid molecules. The invention includes such a nucleic acid molecules and host immune cells containing them. For example, a targeting moiety (eg antibody) may be genetically engineered to contain the further moiety and, if present, the one or more masking moieties, using genetic engineering techniques well established in the art. Thus, it will be appreciated that the further moiety (including separate parts thereof) and, if present, the one or more masking moieties, may be embedded within the polypeptide sequence of the targeting moiety, provided that the immune cell binding region of the further moiety can be unmasked when the molecule is in the vicinity of unwanted cells, such that the further moiety can bind to an immune cell. It will be appreciated that the each of the targeting moiety, further moiety and, if present, one or more masking moieties need not be encoded by contiguous sections of polynucleotide. For example, although the further moiety may be fused to the terminus of the targeting moiety, and, if present, the one or more masking moieties fused to the terminus of the further moiety, it is also contemplated that the various moieties of the molecule may be encoded by non-contiguous polynucleotide sequences, and between these non-contiguous polynucleotide sequences, polynucleotides sequences may exist that encode other moieties of the molecule. For example, it is clear from FIG. 4 that separate parts of the further moiety are encoded by non-contiguous sections of polynucleotide sequence and between these sections there is a polynucleotide sequence that encodes the targeting moiety.

It is further appreciated that the molecule of the invention may comprise two or more polypeptide chains that fold into the correct conformation where the two or more polypeptide chains are mixed. Each of the two or more polypeptides may include one or more of the targeting moiety, further moiety (including separate parts thereof) and, if present, the one or more masking moieties. This is illustrated by the molecule depicted in FIG. 2 and is particularly relevant when any of the targeting moiety, further moiety and, if present, the one or more masking moieties comprise one or more immunoglobulin domains, since the domains on one polypeptide chain (eg VH domain) may pair with domains on another polypeptide chain (eg VL domain). Pairing of immunoglobulin domains derived from different polypeptide chains is well known in the art, and forms the basis of the preparation of diabodies and triabodies.

It follows that when in the specific embodiment where the targeting moiety, further moiety and, if present, the one or more masking moieties are covalently attached and where all moieties are peptides or polypeptides, the molecule of the invention may be considered to be a bispecific antibody (eg a BiTE bispecific antibody). For example, the bispecific antibody may comprise (i) a first portion that is capable of specifically binding to an unwanted cell and (ii) a second portion that comprises a masked immune cell binding region so as to prevent binding of the second portion to an immune cell, wherein the masked immune cell binding region is capable of being selectively unmasked when the bispecific antibody is in the vicinity of the unwanted cells so as to allow binding to an immune cell. In this instance, the first portion of the bispecific antibody may correspond to the targeting moiety described above and the second portion of the bispecific antibody may correspond to the further moiety described above. Preferably, the antibody is a single chain antibody construct; however, it is appreciated that the antibody may comprise two or more polypeptide chains, as discussed above.

Preferably, the immune cell binding region of the bispecific antibody is a T cell binding region. Thus, the bispecific antibody may comprise (i) a first portion that is capable of specifically binding to an unwanted cell and (ii) a second portion that comprises a masked T cell binding region so as to prevent binding of the second portion to a T cell, wherein the masked T cell binding region is capable of being selectively unmasked when the bispecific antibody is in the vicinity of the unwanted cells so as to allow binding to a T cell. Typically, the T cell binding region is one that can bind to the CD3 antigen and/or TCR present on a T cell.

It is also preferred that the immune cell binding region is unmasked by selective cleavage of one or more cleavage sites in the molecule when in the vicinity of the unwanted cells. Thus, the bispecific antibody may comprise (i) a first portion that is capable of specifically binding to an unwanted cell and (ii) a second portion that comprises a masked immune cell binding region so as to prevent binding of the second portion to an immune cell, wherein the masked immune cell binding region is unmasked by selective cleavage of one or more cleavage sites in the molecule when in the vicinity of the unwanted cells so as to allow binding to an immune cell.

Accordingly, the invention provides a bispecific antibody comprising (i) a first portion that is capable of specifically binding to an unwanted cell and (ii) a second portion that comprises a masked T cell binding region so as to prevent binding of the second portion to a T cell, wherein the masked T cell binding region is unmasked by selective cleavage of one or more cleavage sites in the molecule when in the vicinity of the unwanted cells so as to allow binding to a T cell. Typically, the T cell binding region is one that can bind to the CD3 antigen and/or TCR present on a T cell.

Suitably, the targeting moiety, further moiety and, if present, the one or more masking moieties are joined so that all moieties retain their respective activities such that the molecule may be targeted to an unwanted cell and the immune cell binding region may be unmasked within the vicinity of the unwanted cells so as to bind to an immune cell.

The targeting moiety and further moiety are typically joined by a linker peptide. Preferably, the linker joining the targeting moiety and further moiety contains between 2 and 100 amino acid residues, such as more than or less than 10, 20, 30, 40, 50, 60, 70, 80 and 90 amino acids. More preferably, the linker joining the targeting moiety and further moiety contains between 2 and 50 amino acids and still more preferably between 4 and 20 amino acids. Thus, the linker peptide may comprise 5, 6, 7, 8, 9, 10, 11, 12, 13, 14, 15, 16, 17, 18 or 19 amino acids.

The one or more masking moieties are typically joined to the further moiety (including separate parts thereof) by a respective one or more linker peptides. The lengths of such linker peptides may depend on how the one or more masking moieties are operating to mask the T cell binding region. For example, if the one or more masking moieties are immunoglobulin domains that are intended to pair with variable domains of a further moiety (e.g. FIG. 4), the linkers that join the one or more immunoglobulin domains of the masking moieties with the respective variable domains of the further moiety must be of a sufficient length to allow pairing between the respective immunoglobulin domains of the one or more masking moieties and the respective variable domains of the further moiety. Generally, therefore, the linkers are at least 15 amino acids in length, such as at least 16, 17, 18, 19, 20, 21, 22, 23, 24, 25, 26, 27, 28, 29, 30, 31, 32, 33, 34, 35, 36, 37, 38, 39 or 40 amino acids in length. If the one or more masking moieties are simply blocking access to the underlying T cell binding region of the further moiety (e.g. FIGS. 2 and 3), it will be appreciated that the one or more linkers joining the respective one or more masking moieties to the further moiety may be shorter, or even zero length. Typical amino acid lengths include at least 1, 2, 3, 4, 5, 6, 7, 8, 9, 10, 11, 12, 13, 14, 15 amino acids. However, longer linkers may also be used especially when the masking moiety is an immune cell surface antigen (e.g. FIG. 3). Thus, the linker may be at least 16, 17, 18, 19, 20, 21, 22, 23, 24, 25, 26, 27, 28, 29, 30, 31, 32, 33, 34, 35, 36, 37, 38, 39 or 40 amino acids in length. If the one or more masking moieties are immunoglobulin domains that are intended to prevent pairing of variable domains of a further moiety but without the immunoglobulin domains of the one or more masking moieties pairing with the variable domains of the further moiety, the linkers that join the one or more immunoglobulin domains of the masking moieties with the respective variable domains of the further moiety must be of an insufficient length to allow pairing between the respective immunoglobulin domains of the one or more masking moieties and the respective variable domains of the further moiety. Thus, the linkers are generally 14 amino acids or less, such as 13, 12, 11, 10, 9, 8, 7, 6, 5, 4, 3, 2 or 1 amino acid in length.

In some embodiments, the one or more masking moieties may be joined to the targeting moiety (e.g. FIG. 4). Typically, the one or more masking moieties are joined to the targeting moiety by a respective one or more linker peptides. Preferably, the linker joining the targeting moiety and further moiety contains between 2 and 100 amino acid residues, more preferably between 2 and 50 and still more preferably between 4 and 20 amino acids (eg at least 5, 6, 7, 8, 9, 10, 11, 12, 13, 14, 15, 16, 17, 18 or 19 amino acids).

Suitable linker peptides are those that typically adopt a random coil conformation, for example the polypeptide may contain alanine or proline or a mixture of alanine plus proline residues.

Polynucleotides which encode suitable targeting moieties and further moieties are known in the art or can be readily designed from known sequences such as from sequences of proteins known to interact with surface markers expressed on unwanted cells or immune cells or contained in nucleotide sequence databases such as the GenBank, EMBL, ImMunoGeneTics (IMGT), and dbEST databases. Polynucleotides which encode suitable one or more masking moieties are also known in the art or can readily be designed from known sequences or sequences in the above databases and made.

Polynucleotides which encode suitable linker peptides can readily be designed from linker peptide sequences and made.

Thus, polynucleotides which encode the molecules used in the invention can readily be constructed using well known genetic engineering techniques.

The nucleic acid is then expressed in a suitable host to produce a molecule of the invention. Thus, the nucleic acid encoding the molecule of the invention may be used in accordance with known techniques, appropriately modified in view of the teachings contained herein, to construct an expression vector, which is then used to transform an appropriate host cell for the expression and production of the molecule of the invention of the invention.

It is appreciated that the nucleic acid encoding the molecule of the invention may be joined to a wide variety of other nucleic acid sequences for introduction into an appropriate host. The companion nucleic acid will depend upon the nature of the host, the manner of the introduction of the nucleic acid into the host, and whether episomal maintenance or integration is desired, as is well known in the art.

In an alternative embodiment, the targeting moiety, further moiety (including separate parts thereof) and one or more masking moieties may be non-covalently attached. For non-covalent bindings, immunological bindings or such binding as via biotin/avidin or streptavidin, respectively, are preferred. For example, the targeting moiety may be a bispecific antibody, one specificity of which is directed to an entity expressed by the unwanted cell and one specificity of which is directed to the further moiety or part thereof. Also, it is possible to couple the further moiety to another substance against which, in turn, the specificity of the bispecific antibody will be directed to. For instance, the further moiety may contain further peptidic sequences which are recognised by the bispecific antibody. Another possibility involves coupling the targeting moiety, for example to streptavidin whilst the further moiety is coupled to biotin, and vice versa. Other means by which non-covalent interactions can be formed include leucine zipper sequences or affinity bonds. In any event, it is preferred that there are one or more cleavage sites within the molecule that are cleavable selectively when the molecule is in the vicinity of the unwanted cells, such that the immune cell binding region can be unmasked.

Although less preferred, the targeting moiety, further moiety (including separate parts thereof) and one or more masking moieties may be conveniently linked to each other by any of the conventional ways of cross-linking molecules, such as those generally described in O'Sullivan et al *Anal. Biochem*. (1979) 100, 100-108. For example, one of the targeting moiety or further moiety (including separate parts thereof) or masking moiety or spacer moiety may be enriched with thiol groups and the moiety it is to be linked to reacted with a bifunctional agent capable of reacting with those thiol groups, for example the N-hydroxysuccinimide ester of iodoacetic acid (NHIA) or N-succinimidyl-3-(2-pyridyldithio)propionate (SPDP), a heterobifunctional cross-linking agent which incorporates a disulphide bridge between the conjugated species. Amide and thioether bonds, for example achieved with m-maleimidobenzoyl-N-hydroxysuccinimide ester, are generally more stable in vivo than disulphide bonds.

It is known that bis-maleimide reagents allow the attachment of a thiol group (e.g. thiol group of a cysteine residue of an antibody) to another thiol-containing moiety (e.g. thiol group of an immune cell antigen or a linker intermediate), in a sequential or concurrent fashion. Other functional groups besides maleimide, which are reactive with a thiol group include iodoacetamide, bromoacetamide, vinyl pyridine, disulfide, pyridyl disulfide, isocyanate, and isothiocyanate.

Further useful cross-linking agents include S-acetylthioglycolic acid N-hydroxysuccinimide ester (SATA) which is a thiolating reagent for primary amines which allows deprotection of the sulphydryl group under mild conditions (Julian et al (1983) *Anal. Biochem*. 132, 68), dimethylsuberimidate dihydrochloride and N,N'-o-phenylenedimaleimide.

Particularly preferred crosslinking agents include sulfosuccinimidyl 4-[N-maleimidomethyl]cyclohexane-1-carboxylate (Sulfo-SMCC), sulfosuccinimidyl 6-(3'-[2-pyridyldithio]-propionamido) hexanoate (Sulfo-LC-SPDP) and N[β-Maleimidopropionic acid]hydrazide, trifluoroacetic acid salt (BMPH).

It will be understood that a large number of homobifunctional and heterobifunctional crosslinking chemistries would be appropriate to join the various moieties of the molecule together, and any such chemistry may be used. For example, Click Chemistry using Staudinger Ligation Chemistry (phosphine-azido chemistry) may be used.

Amino acid residues described herein are generally in the natural "L" isomeric form, which is preferred. However, residues in the "D" isomeric form can be substituted for L-amino acid residues in certain situations, provided that the agent of the invention still retains its function, namely to prevent or treat a condition characterised by the presence of unwanted cells. The definition also includes, unless otherwise specifically indicated, chemically-modified amino acids, including amino acid analogues (such as penicillamine, 3-mercapto-D-valine), naturally-occurring non-proteogenic amino acids (such as norleucine), beta-amino acids, azapeptides, N-methylated amino acids and chemically-synthesised compounds that have properties known in the art to be characteristic of an amino acid. The term "proteogenic" indicates that the amino acid can be incorporated into a protein in a cell through well-known metabolic pathways. The definition also includes amino acids in which the functional side group has been chemically derivatised. Such derivatised molecules include, for example, those molecules in which free amino groups have been derivatised to form amine hydrochlorides, p-toluene sulfonyl groups, carbobenzoxy groups, t-butyloxycarbonyl groups, chloroacetyl groups or formyl groups. Free carboxyl groups may be derivatised to form salts, methyl and ethyl esters or other types of esters or hydrazides. Free hydroxyl groups may be derivatised to form O-acyl or O-alkyl derivatives. Also included as derivatives are those peptide portions that contain one or more naturally occurring amino acid derivatives of the twenty standard amino acids.

Accordingly, it is appreciated that the peptide portions of the molecule of the invention can be peptide "mimetics", i.e. peptidomimetics which mimic the structural features of peptides comprising or consisting of the amino acid sequence as described herein. Peptidomimetics can be even more advantageous in therapeutic use, in the resistance to degradation, in permeability or in possible oral administration.

A primary goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogues have been obtained. In some instances, these analogues have been shown to possess longer biological half-lives than their naturally-occurring counterparts. In another approach, a variety of uncoded or modified amino acids such as D-amino acids and N-methyl amino acids have been used to modify mammalian peptides. Alternatively, a presumed bioactive conformation has been stabilised by a covalent modification, such as cyclization or by incorporation of γ-lactam or other types of bridges (Veber et al, 1978) and Thorsett et al, 1983). Another approach, disclosed by Rich (1986) has been to design peptide mimics through the application of the transition state analogue concept in enzyme inhibitor design. For example, it is known that the secondary alcohol of statine mimics the tetrahedral transition state of the sessile amide bond of the pepsin substrate. Other approaches include the use of azapeptides and beta-amino acids.

Also included in the definition of 'peptidomimetics', are retro-inverso peptides. By retro-inverso peptides (also known as all-D-retro or retro-enantio peptides) we include the meaning of a peptide in which all of the L-amino acids are replaced with D-amino acids and the peptide bonds are reversed. Thus, the peptides are composed of D-amino acids assembled in the reverse order from that of the parent L-sequence. Retro-inverso peptides can be synthesised by methods known in the art, for example such as those described in Meziere et al (1997) *J. Immunol.* 159 3230-3237. This approach involves making pseudopeptides containing changes involving the backbone, and not the orientation of side chains which remain very similar to the parent peptide. Retro-inverse peptides are much more resistant to proteolysis.

Therefore, it will be appreciated that when any of the targeting moiety, further moiety, one or more masking moieties, cleavage site, and spacer moieties as described herein are peptides or polypeptides, any one or more of those peptides or polypeptides may be substituted for a corresponding peptidomimetic that retains the respective activity of the parent peptide or polypeptide. This may help to confer protease resistance on the agent of the invention and thereby improve its stability. Thus, for example, when a targeting moiety is attached to a further moiety via one or more peptide spacer moieties, it may be desirable for one or more of those spacer moieties to be peptidomimetics, e.g. wherein one or more of the naturally occurring amino acids of the spacer moieties are replaced or modified, for example, to improve stability.

Another approach to increase stability of peptide portions of the agent of the invention is to have stabilising groups at one or both termini. Typical stabilising groups include amido, acetyl, benzyl, phenyl, tosyl, alkoxycarbonyl, alkyl carbonyl, benzyloxycarbonyl and the like end group modifications. Additional modifications include using a "D" amino acid in place of a "L" amino acid at the termini, and amide rather than amino or carboxy termini or acetyl rather than amino termini, to inhibit exopeptidase activity. Thus, it is appreciated that whenever the agent of the invention has an exposed peptide terminus, that terminus may have a capping moiety, preferably a moiety that is less than 200 Da in molecular weight. Further capping moieties include a naftyl group or a polyethylene glycol group. It is appreciated that retro-inverso peptides are already relatively stable and so may not require additional capping moieties.

Preferably, the molecule of the invention has a half-life in plasma of at least 24 hours at 37° C.

It may be desirable to modify the molecule of the invention so that it can be more easily detected, for example by biotinylating it or by incorporating any detectable label known in the art such as radiolabels, fluorescent labels or enzymatic labels.

As discussed above, the molecules of the invention have utility in redirecting the body's immune machinery to eradicate or neutralise particular unwanted cells in a specific manner. Since any unwanted cell may be targeted in this way, the molecules of the invention offer significant therapeutic potential.

Accordingly, a second aspect of the invention provides a method of preventing or treating a condition characterised by the presence of unwanted cells, the method comprising administering a molecule according to the first aspect of the invention to a subject.

Thus, the method may involve identifying a subject who has a condition or who is at risk of developing a condition characterised by unwanted cells (eg cancer), administering the molecule according to the first aspect of the invention to the subject, and monitoring the levels of the unwanted cells in the subject either by conducting tests to determine the number of unwanted cells or by monitoring the clinical symptoms of the subject. Depending on the results of the monitoring step, it may be necessary to administer more of the agent.

Similarly, the invention includes a molecule according to the first aspect of the invention for use in preventing or treating a condition characterised by the presence of unwanted cells.

The invention also includes the use of a molecule according to the first aspect of the invention in the manufacture of a medicament for preventing or treating a condition characterised by the presence of unwanted cells.

Preferences for the condition and unwanted cells, are as described above with respect to the first aspect of the invention. Examples of particular conditions include tumours (benign or malignant), autoimmune conditions, cardiovascular diseases, degenerative diseases, diabetes, allergic disease (eg asthma), neurodegenerative diseases such as Alzheimer's, transplantation patients and infectious diseases. Preferably, the unwanted cells are cancer cells and the condition is a cancer. The cancer may be any cancer such as breast cancer, ovarian cancer, endometrial cancer, cervical cancer, bladder cancer, renal cancer, melanoma, lung cancer, prostate cancer, testicular cancer, thyroid cancer, brain cancer, oesophageal cancer, gastric cancer, pancreatic cancer, colorectal cancer, liver cancer, leukaemia, myeloma, non-Hodgkin's lymphoma, Hodgkin's lymphoma, acute myeloid leukaemia, acute lymphoblastic leukaemia, chronic lymphoblastic leukaemia, lymphoproliferative disorder, myelodysplastic disorder, myeloproliferative disease and premalignant disease. It will be appreciated that the molecule of the invention also has utility in regenerative medicine (eg laboratory grown organs or tissues).

By preventing or treating a condition we include the meaning of reducing or alleviating symptoms in a patient (i.e. palliative use), preventing symptoms from worsening or progressing, treating the disorder (e.g. by inhibition or elimination of the causative agent), or prevention of the condition or disorder in a subject who is free therefrom.

It will be appreciated that the molecules of the invention lend themselves to personalised medicine in the clinic whereby the most appropriate molecule to be administered to the patient is determined, and either selected or prepared in the clinic. For example, it may be desirable to acquire an expression profile of the unwanted cell in a patient so that the optimum targeting moiety for that patient can be selected. Assessing the expression profile of the unwanted cell may be carried out on a biopsy sample using routine assays for measuring nucleic acid (e.g. DNA or RNA transcripts) or protein levels. For example, transcriptomic or proteomic techniques may be used. In this way, it will be possible to identify tailored targeting moieties that bind specifically to, for example, surface markers expressed by the unwanted cell. It may also be possible to identify appropriate protease cleavage sites that may be selectively cleaved in the vicinity of the unwanted cells. For example, it may be that a molecule containing one or more MMP2 cleavage sites would not be activated by a given patient's cancer proteases, but a molecule containing one or more MMP9 cleavage sites would be activated.

Thus the method of the second aspect of the invention may include the steps of (i) identifying a subject who has a condition, or who is at risk of developing a condition characterised by the presence of unwanted cells (eg cancer), (ii) taking a sample from the subject, (iii) analysing the sample to identify the optimum targeting moiety and/or cleavage site for preventing or treating the condition in that subject, (iii) preparing the molecule of the invention, (iv) administering the molecule to the subject, and (v) monitoring the levels of unwanted cells in the subject either by conducting tests to determine the number of unwanted cells or by monitoring the clinical symptoms of the subject.

It is appreciated that an apparatus may be used to select and optionally prepare the most appropriate molecule to be used for a particular patient. For example, the apparatus may perform an automated analysis of one or more samples from the subject, and based on this analysis select and optionally prepare a tailor-made molecule for that subject. Thus the apparatus may carry out an expression profile of unwanted cells from the subject (eg from a biopsy sample) so as to determine a suitable targeting moiety that will bind to the unwanted cell and/or determine a suitable cleavage site that will be selectively cleaved in the vicinity of the unwanted cell.

By performing any one or more of these steps in the clinic a molecule tailored for a particular subject can be prepared. For example, the molecule can contain a targeting moiety that is known to bind selectively to surface markers expressed by the unwanted cell, and/or a cleavage site (e.g. protease cleavage site) that allows unmasking of the immune cell binding region (eg T cell binding region) when the molecule is in the vicinity of the unwanted cells.

In one embodiment, the subject is administered a further therapeutic agent in addition to the molecule according to the first aspect of the invention. For example, when administering the molecule to prevent or treat a particular condition, a further therapeutic agent known to be useful for combating that condition may be administered. As an example, when the molecule is for treating cancer, a further anti-cancer agent (eg anti-neoplastic chemotherapy) may be administered to the subject alongside the molecule of the invention. Similarly, the further therapeutic agent may be one that is known to have therapeutic application in allergic disease, inflammatory disease, regenerative medicine and neuroregenerative disease.

It is appreciated that the further therapeutic agent may be administered at the same time as the molecule of the invention (i.e. simultaneous administration optionally in a co-formulation) or at a different time to the molecule of the invention (i.e. sequential administration).

The further therapeutic agent may be any one or more of a vaccine; an immuno stimulatory drug; an anti-cancer agent; an agent inhibiting an antibody response against the agent of the invention; and/or a protease inhibitor.

For example, it may be desirable to administer immunostimulating agents such as IL-2, IL-7, IFNα, GM-CSF, metformin, lenalidomide; and/or administer anti-immunoregulatory agents such as Ipilimumab; all of which may be considered as further therapeutic agents.

It is also appreciated that if the subject is one to whom is administered immunosuppressive agents, that these immunosuppressive agents may be withdrawn from the subject (e.g. by suspending treatment) when or before being administered the agent of the invention. This is particularly true where the subject is one to whom is administered immunosuppressive agents to ablate T cells.

Similarly, it may be desirable to employ methods aimed at circumventing any immunogenicity issues relating to the molecule of the invention whereby an adverse antibody response is elicited in vivo. For example, the subject may also be administered one or more agents that are known to inhibit the activity of B cells, such as any of Rituximab, cyclophosphamide, Syk inhibitors, an anti-BAFF antibody (eg Belimumab), an anti-CD22 antibody, an anti-CD20 antibody and an anti-CD19 antibody, all of which may be considered as further therapeutic agents. In this case, it is particularly preferred if the inhibitor of B cells is administered to the subject prior to the molecule of the invention, eg as a pre-treatment to ablate B cells.

In another embodiment, where the molecule comprises one or more protease cleavage sites, it may be appropriate to administer a particular protease inhibitor so as to improve the target selectivity of the molecule of the invention. For example, if a targeting moiety is known to bind cells in both the heart and breast tissue, but only those in the breast are to be targeted, it may be desirable to administer an agent that selectively inhibits the protease responsible for unmasking the immune cell binding region, in the heart but not the breast. In other words, an agent is administered to inhibit a protease that is capable of unmasking the immune cell binding region but which protease resides in the vicinity (eg at or near the surface of) of wanted cells but not in the vicinity (eg at or near the surface of) of unwanted cells. This is particularly useful in the event that a protease cleavage site within the molecule of the invention is cleavable by multiple proteases, some of which reside in the vicinity of unwanted cells and some of which reside in the vicinity of wanted cells. In this case, targeting specificity may be improved by administering a protease inhibitor that inhibits a protease that resides in the vicinity of wanted cells but nevertheless is capable of cleaving the cleavage site and therefore unmasking the immune cell binding region. The effect of administering the inhibitor would be to ensure that the immune cell binding region is preferentially unmasked in the vicinity of the unwanted cells. For instance, if a subject with cancer also has active rheumatoid arthritis where MMP2 and other proteases are active, and the one or more cleavage sites in the molecule of the invention are cleavable by multiple proteases including MMP2, it may be beneficial to inhibit MMP2 to prevent cleavage of the molecule at the arthritic joint but retain cleavage at the cancer site by another protease. The invention thus includes a composition comprising (i) a molecule according to the first aspect of the invention and (ii) a further therapeutic agent, for use in preventing or treating a condition characterised by the presence of unwanted cells. Given that the molecule of the invention and the further therapeutic agent may be administered simultaneously or sequentially, it will be appreciated that the invention includes a molecule according to the first aspect of the invention for use in preventing or treating a condition characterised by the presence of unwanted cells in a subject who is administered a further therapeutic agent. It also follows that the invention includes a therapeutic agent for use in preventing or treating a condition characterised by the presence of unwanted cells in a subject who is administered a molecule according to the first aspect of the invention.

Similarly, the invention includes a use of a composition comprising (i) a molecule according to the first aspect of the invention and (ii) a further therapeutic agent, in the manufacture of a medicament for preventing or treating a condition characterised by the presence of unwanted cells. Again, given that the molecule of the invention and the further therapeutic agent may be administered simultaneously or sequentially, it will be appreciated that the invention includes the use of a composition comprising a molecule according to the first aspect of the invention in the manufacture of a medicament for preventing or treating a condition characterised by the presence of unwanted cells in a subject who is administered a further therapeutic agent. It also follows that the invention includes the use of a therapeutic agent in the manufacture of a medicament for preventing or treating a condition characterised by the presence of unwanted cells in a subject who is administered a molecule according to the first aspect of the invention.

The invention also provides a composition comprising (i) a molecule according to the first aspect of the invention and (ii) a further therapeutic agent suitable for preventing or treating the same condition characterised by the presence of unwanted cells. It is appreciated that the therapeutic agent mentioned in the immediately preceding two paragraphs may be agents suitable for treating the same condition characterised by the presence of unwanted cells, as treatable by the molecules of the invention.

A third aspect of the invention provides a molecule according to the first aspect of the invention for use in medicine.

A fourth aspect of the invention a pharmaceutical composition comprising a molecule according to the first aspect of the invention, and a pharmaceutically acceptable carrier, diluent or excipient.

Whilst it is possible for the molecule of the invention to be administered alone, it is preferable to present it as a pharmaceutical formulation, together with one or more acceptable carriers. The carrier(s) must be "acceptable" in the sense of being compatible with the therapeutic agent and not deleterious to the recipients thereof. Typically, the carriers will be water or saline which will be sterile and pyrogen free.

Where appropriate, the formulations may conveniently be presented in unit dosage form and may be prepared by any of the methods well known in the art of pharmacy. Such methods include the step of bringing into association the active ingredient (agent for treating or preventing a condition characterised by unwanted cells) with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The molecule of the invention can be administered in the form of a suppository or pessary, or they may be applied topically in the form of a lotion, solution, cream, ointment or dusting powder. The molecule may also be transdermally administered, for example, by the use of a skin patch.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The amount of the molecule which is administered to the individual is an amount effective to combat the particular individual's condition. The amount may be determined by the physician.

Preferably, in the context of any aspect of the invention described herein, the subject to be treated is a human. Alternatively, the subject may be an animal, for example a domesticated animal (for example a dog or cat), laboratory animal (for example laboratory rodent, for example mouse, rat or rabbit) or an animal important in agriculture (i.e. livestock), for example horses, cattle, sheep or goats.

The invention provides a kit of parts for preventing or treating a condition characterised by the presence of unwanted cells, the kit comprising:
  (i) a targeting moiety capable of directly targeting to unwanted cells and which is attached to a first binding partner, and
  (ii) a further moiety that has a masked immune cell binding region so as to prevent binding of the further moiety to an immune cell, and which further moiety is attached to a second binding partner which is capable of binding to the first binding partner,
  wherein the masked immune cell binding region is capable of being selectively unmasked when the further moiety is in the vicinity of the unwanted cells so as to allow binding of the further moiety to an immune cell. Preferably, the immune cell binding region is a T cell binding region (eg one that binds to CD3 antigen and/or TCR on a T cell). Preferably, the immune cell binding region is unmasked by selective cleavage of one or more cleavage sites in the further moiety when in the vicinity of the unwanted cells.

Preferences for the unwanted cells, targeting moiety, further moiety and cleavage sites are as defined above. It is particularly preferred if the kit of parts is for preventing or treating cancer. It is also appreciated that the kit of parts may comprise one or more masking moieties that mask the immune cell binding region of the further moiety. Preferences for the masking moiety are as defined above, and include both masking moieties that promote a conformation of the further moiety in which conformation the immune cell binding region is not accessible to an immune cell, as well as masking moieties that simply block an underlying immune cell binding region of the further moiety.

By the first and second binding partners, we include the meaning of any two moieties which bind to each other selectively. Most preferably, the first and second binding partners only bind to each other and not to any other moieties. Non-covalent binding such as between biotin/avidin or streptavidin, or immunological bindings are preferred. Thus, the first binding partner may be biotin and the second binding partner may be avidin, and vice versa. Alternatively, the first binding partner may be an antigen and the second binding partner may be an antibody specific for that antigen, and vice versa. However, any pair of first and second binding partners that selectively bind to each other may be used, and suitable pairs will be known to the skilled person.

It will be appreciated that the kit allows one to first administer the targeting moiety that directly targets the unwanted cells to the subject, and establish the correct localisation of the targeting moiety in the subject (for example by the targeting moiety being detectably labelled (eg radiolabelled)) before administering the further moiety. The further moiety is then targeted to the unwanted cells by virtue of the second binding partner binding to the first binding partner. Once in the vicinity of the unwanted cells, the immune cell binding region of the further moiety is unmasked, for example by selective cleavage of one or more cleavage sites within the further moiety, allowing an immune cell (eg T cell) to be recruited to the unwanted cells. It will be understood that the further moiety that is attached to a second binding partner may be considered a targeting moiety that is capable of indirectly targeting to an unwanted cell as mentioned above in relation to the first aspect of the invention.

Accordingly, the invention further provides a method of preventing or treating a condition characterised by the presence of unwanted cells, the method comprising administering
  (i) a targeting moiety capable of directly targeting to unwanted cells and which is attached to a first binding partner, and
  (ii) a further moiety that has a masked immune cell binding region so as to prevent binding of the further moiety to an immune cell, and which further moiety is attached to a second binding partner which is capable of binding to the first binding partner,
  wherein the masked immune cell binding region is capable of being selectively unmasked when the further moiety is in the vicinity of the unwanted cells so as to allow binding of the further moiety to an immune cell. Preferably, the immune cell binding region is a T cell binding region (eg one that binds to CD3 antigen and/or TCR on a T cell). It is also preferred that the immune cell binding region is unmasked by selective cleavage of one or more cleavage sites in the further moiety when in the vicinity of the unwanted cells. Preferably, the targeting moiety is administered before the further moiety, for example to allow to correct localisation of the targeting moiety at the unwanted cells to be established. However, the targeting moiety may be administered at the same time as the further moiety. It is appreciated that the targeting moiety and further moiety may be attached to each other by binding of the first and second binding partners.

Similarly, the invention provides a composition comprising:
(i) a targeting moiety capable of directly targeting to unwanted cells and which is attached to a first binding partner, and
(ii) a further moiety that has a masked immune cell binding region so as to prevent binding of the further moiety to an immune cell, and which further moiety is attached to a second binding partner which is capable of binding to the first binding partner,
wherein the masked immune cell binding region is capable of being selectively unmasked when the further moiety is in the vicinity of the unwanted cells so as to allow binding of the further moiety to an immune cell,
for use in preventing or treating a condition characterised by unwanted cells in a subject. Preferably, the immune cell binding region is a T cell binding region (eg one that binds to CD3 antigen and/or TCR on a T cell). It is also preferred that the immune cell binding region is unmasked by selective cleavage of one or more cleavage sites in the further moiety when in the vicinity of the unwanted cells Similarly, the invention provides a use of a composition comprising:
(i) a targeting moiety capable of directly targeting to unwanted cells and which is attached to a first binding partner, and
(ii) a further moiety that has a masked immune cell binding region so as to prevent binding of the further moiety to an immune cell, and which further moiety is attached to a second binding partner which is capable of binding to the first binding partner,
wherein the masked immune cell binding region is capable of being selectively unmasked when the further moiety is in the vicinity of the unwanted cells so as to allow binding of the further moiety to an immune cell,
in the manufacture of a medicament for preventing or treating a condition characterised by the presence of unwanted cells. Preferably, the immune cell binding region is a T cell binding region (eg one that binds to CD3 antigen and/or TCR on a T cell). It is also preferred that the immune cell binding region is unmasked by selective cleavage of one or more cleavage sites in the further moiety when in the vicinity of the unwanted cells.

In an embodiment of the invention, the targeting moiety is an anti-MUC1 antibody, and the further moiety is an anti-CD3 antibody.

In an embodiment of the invention, the targeting moiety is an anti-CD19 antibody, and the further moiety is an anti-CD3 antibody.

The invention will be described in further detail with the aid of the following Figures and Examples.

FIG. 1: Schematic diagram illustrating molecule of the invention. The targeting moiety (1) comprises VH and VL domains specific for an unwanted cell (2), and the further moiety (3) comprises VH and VL domains specific for CD3 antigen. The VH and VL domains of the further moiety are attached by a linker which is of insufficient length to allow pairing, and so the T cell binding region of the further moiety is masked. Cleavage of a cleavage site (5) in the linker when the molecule is in the vicinity of the unwanted cell (2) allows unmasking of the T cell binding region (4).

FIG. 2: Schematic diagram illustrating molecule of the invention. The targeting moiety (1) comprises paired VH and VL domains specific for an antigen on the unwanted cell (2). The further moiety (3) comprises VH and VL domains specific for CD3 antigen. However, the T cell binding region of the further moiety is blocked by the presence of two masking moieties, a CH domain and a CL domain (6) that are joined to the further moiety by respective linkers. Cleavage of cleavage sites (5) in the linkers when the molecule is in the vicinity of the unwanted cell (2) allows unmasking of the T cell binding region (4).

FIG. 3: Schematic diagram illustrating molecule of the invention. The targeting moiety (1) comprises paired VH and VL domains specific for an antigen on the unwanted cell (2). The further moiety (3) comprises VH and VL domains specific for CD3 antigen. However, the T cell binding region of the further moiety is blocked by the presence of a masking moiety (6) which is an immune cell antigen that binds to the T cell binding region, and which is securely tethered to the further moiety by a covalent linker. Cleavage of a cleavage site (5) in the linker when the molecule is in the vicinity of the unwanted cell (2) allows the masking moiety to leave the T cell binding region and so the T cell binding region (4) is unmasked.

FIG. 4: Schematic diagram illustrating molecule of the invention. The targeting moiety (1) comprises paired VH and VL domains specific for an antigen on the unwanted cell (2). The further moiety (3) comprises VH and VL domains specific for CD3 antigen. However, the VH and VL domains of the further moiety (3) are unable to pair due to the presence of two masking moieties (6) respectively comprising a VL and a VH domain. The VL and VH domains of the masking moieties act as dummy domains that pair with the VH and VL domains of the further moiety and so prevent the VH and VL domains of the further moiety from pairing. The T cell binding region (4) is therefore masked. Cleavage of cleavage sites (5) in linkers that join the further moiety to the one or more masking moieties when the molecule is in the vicinity of the unwanted cell (2) releases the VH and VL domains from pairing with the dummy VH and VL domains of the masking moiety and so the VH domain and VL domain of the further moiety can pair. The T cell binding region (4) is thereby unmasked.

Figure 5:
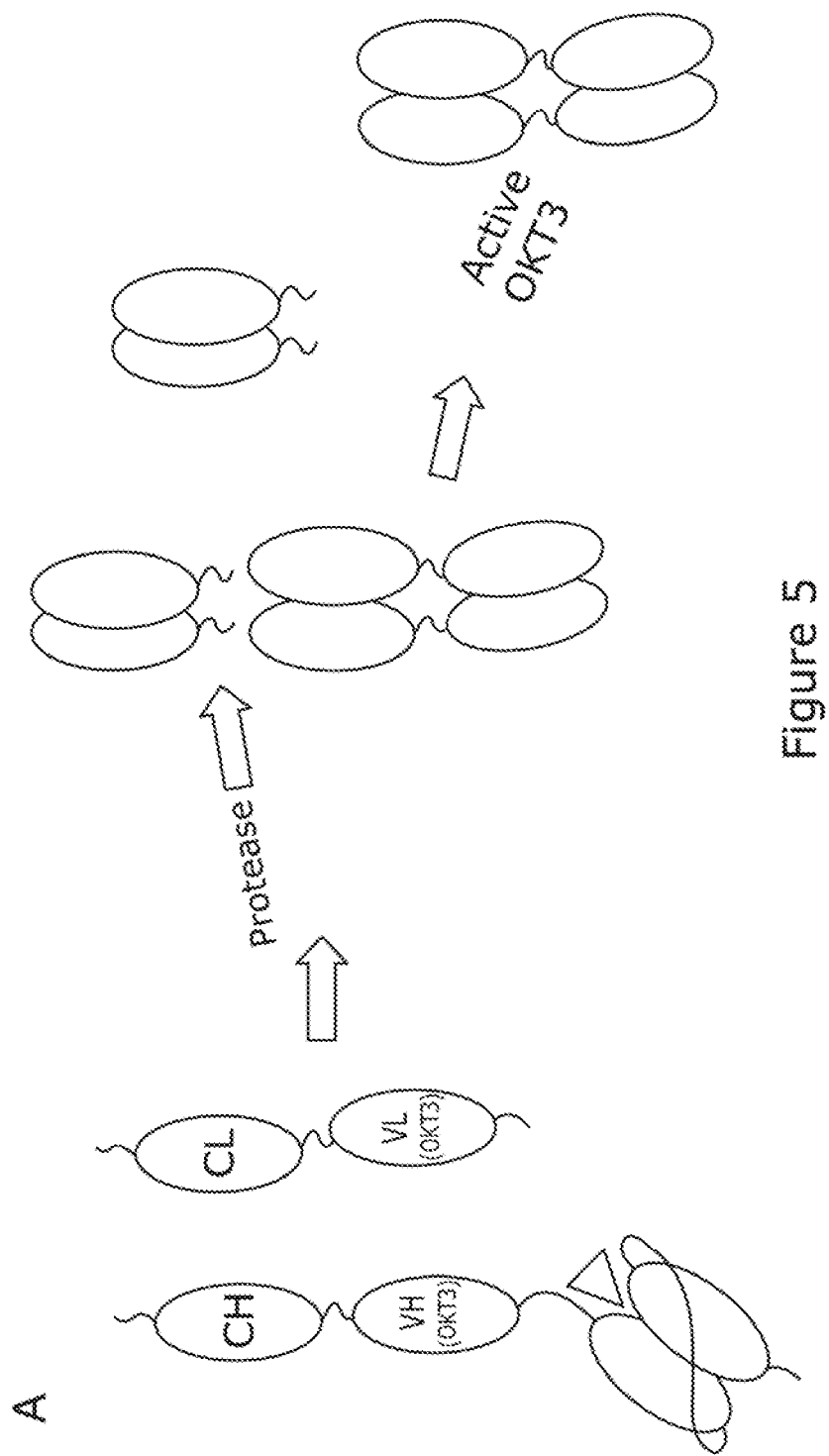
Figure 5:
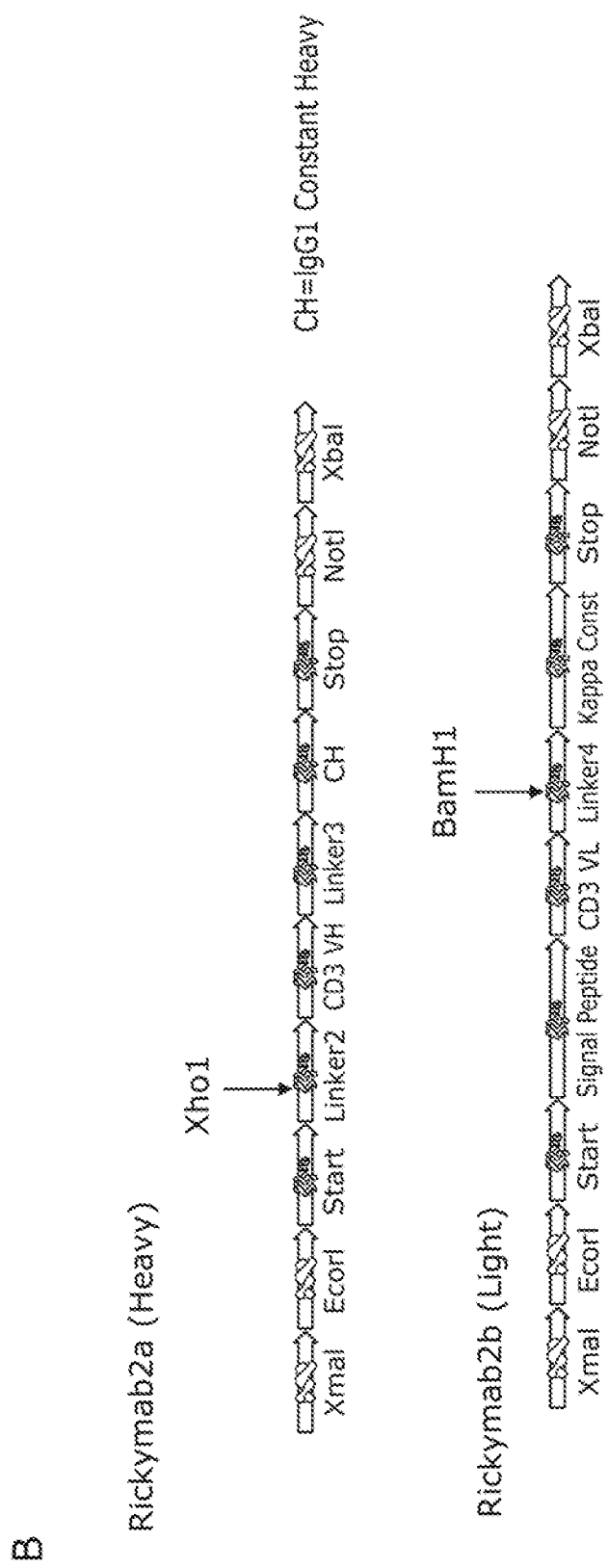

FIG. 5: (A) Schematic diagram illustrating a molecule of the invention. The VH and VL regions encompassing the scFv of the targeting moiety are linked via a single peptide linker to the VH region of the further moiety which in turn is linked via a single peptide linker containing a protease cleavage site to the CH region of the masking moiety. The VL region of the further moiety is linked via a single peptide linker containing a protease cleavage site to the CL region of the masking moiety. The VH and VL regions of the further moiety and the CH and CL regions of the masking moiety will pair when the proteins are incubated together. Thus, the CH and CL regions of the masking moiety prevent the VH and VL regions of the further moiety from interacting with its natural ligand (eg CD3) and from activating T cells. However, after binding to unwanted cells via the target moiety, specific proteolytic cleavage will occur in the vicinity of unwanted cells and the masking moiety will be thereby released allowing interaction of T cells with the unwanted cell. (B) Schematic diagram denoting the genetic make-up of the protein chains depicted in (A). Rickymab (Heavy) comprises the VH of the further moiety and the CH region of the masking moiety and this will be molecularly cloned together with the scFv of the target moiety. Rickymab (Light) comprises the VL region of the further moiety and the CL region of the masking moiety which will pair with the VH and CH regions of Rickymab (Heavy) after introducing the DNA into cells capable of generating the embodiment.

Figure 6:
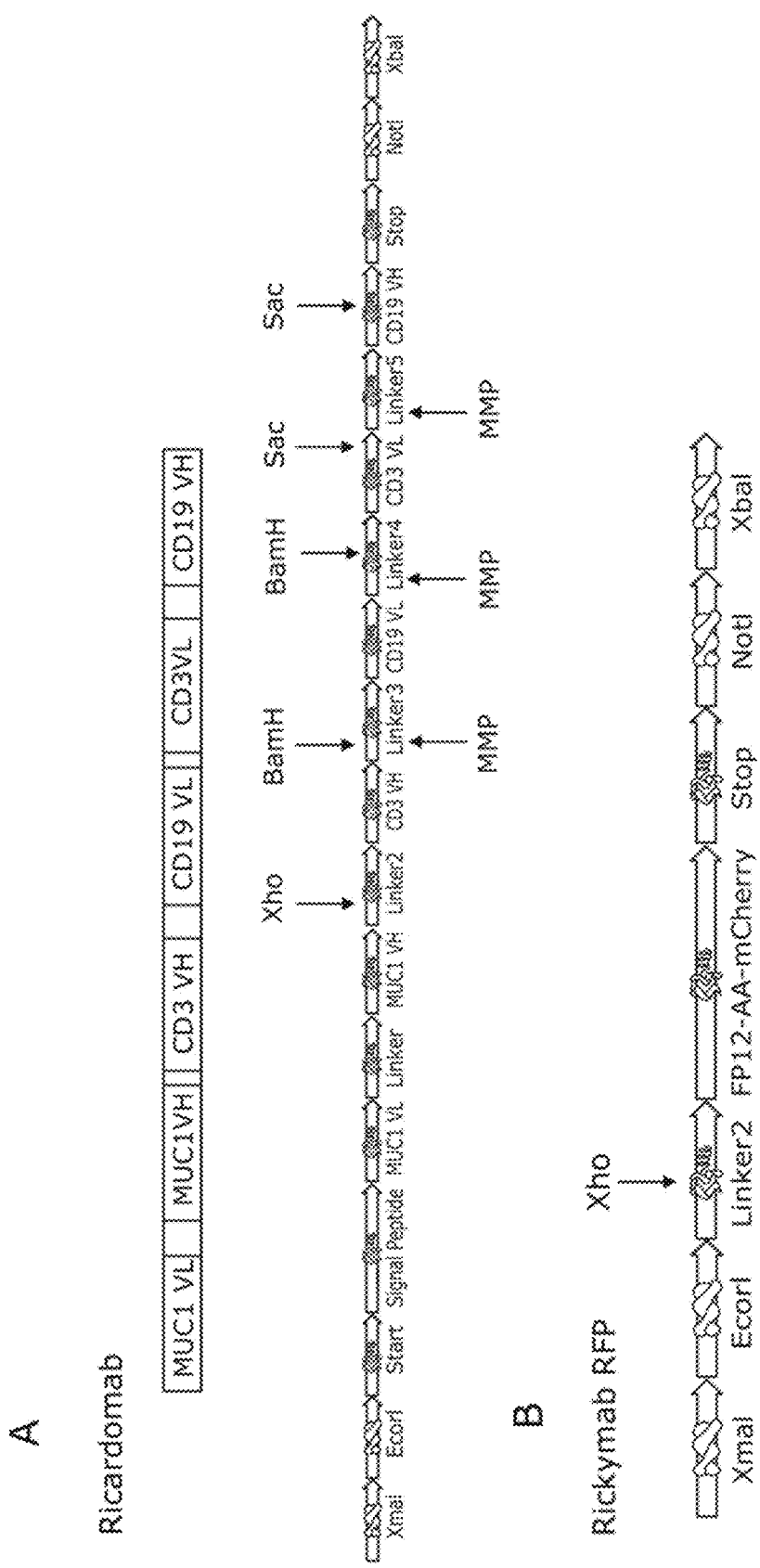

FIG. 6: (A) Schematic diagram that denotes the regions of DNA combined together to form the polypeptide chain seen in FIG. 4. Further indications by arrow denote protease cleavage sites and sites of DNA enzyme cleavage (BamH, Sac & Xho) allowing for movement of regions within the molecule to generate the molecules seen in FIGS. 1, 2, 4 and 5. (B) Schematic diagram that denotes the regions of DNA that make up the VH and CH regions of the target moiety in (A) coupled to a fluorescent dye. The VH and CH regions of the other molecules (eg FIGS. 1-5) could also be linked to the fluorescent dye by enzymatic digestion of the DNA and subsequent ligation to the fluorescent dye. Once the labelled molecule is used to label cells, those cells can be viewed using flow cytometry. This allows demonstration that the target moiety binds to the unwanted cells of interest and not any wanted cell types.

Figure 7:
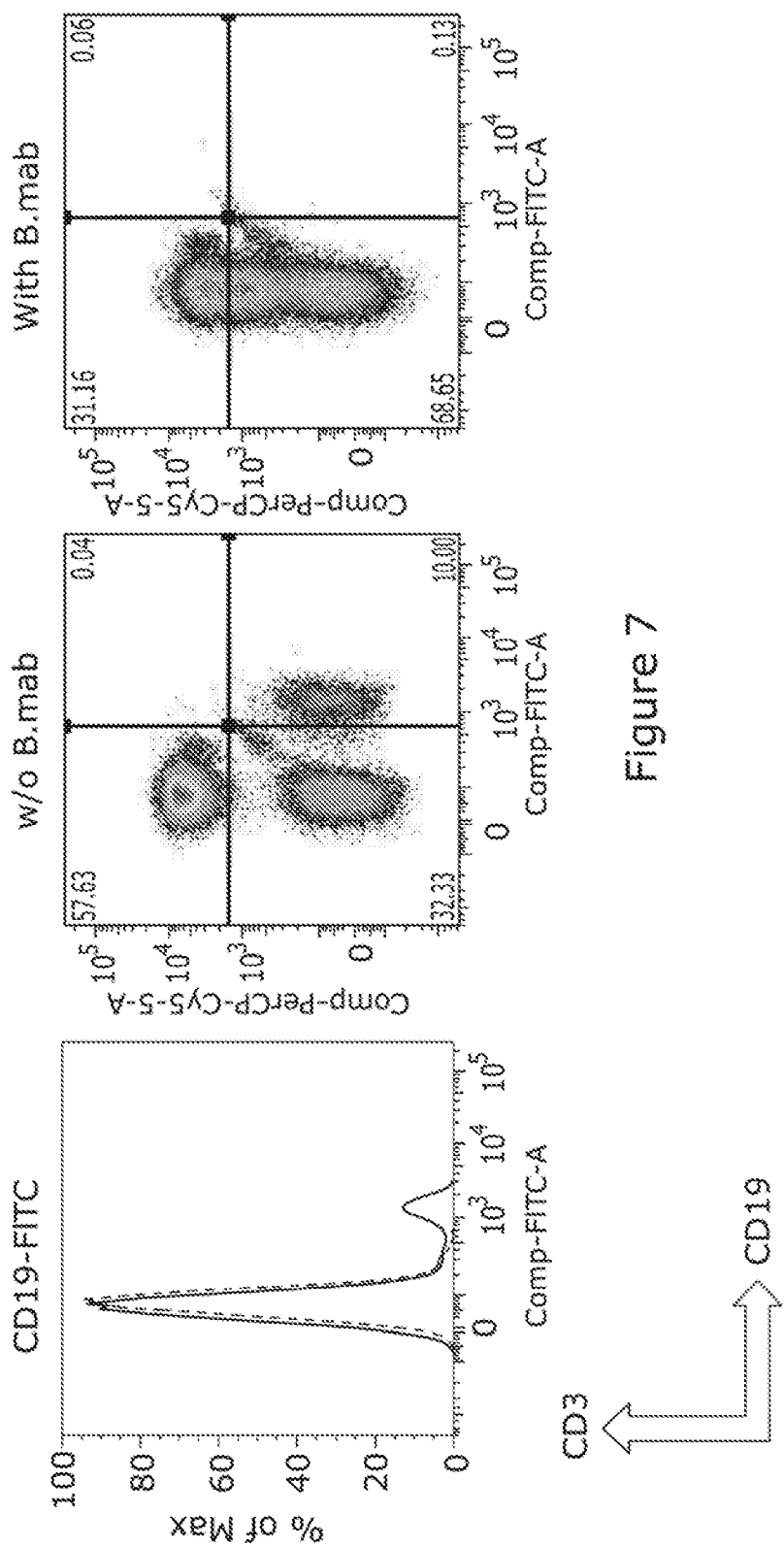
Figure 7:
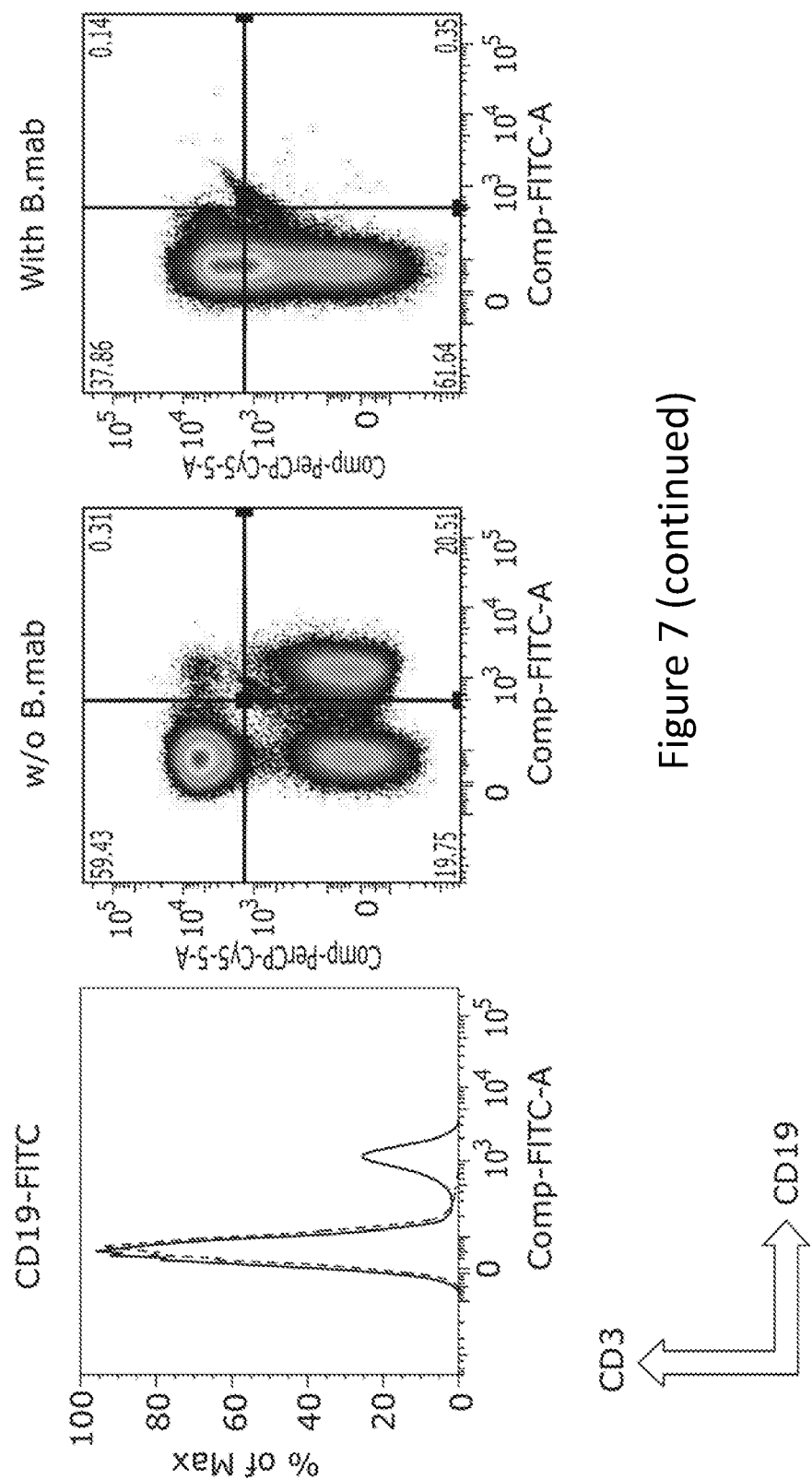

FIGS. 7A-7B: Peripheral blood mononuclear cells (PBMCs) from 2 donors (with different HLA types) were incubated with the molecule exemplified in FIG. 3 (comprising an anti-CD19 scFv (targeting moiety) linked to an anti-CD3 scFv (the further moiety) further linked to the CD3 epsilon domain (the masking moiety)—B.mab) and incubated overnight at 37° C. with the addition of a protease to release the active site of the further moiety. The following day, cells were labelled with antibodies against anti-CD3 to determine the presence of T cells after incubation with the molecule and also anti-CD19 to determine the presence/absence of B cells (see Example 2). Incubation with the molecule removes all B cells from the PBMCs as would be expected.

Figure 8:
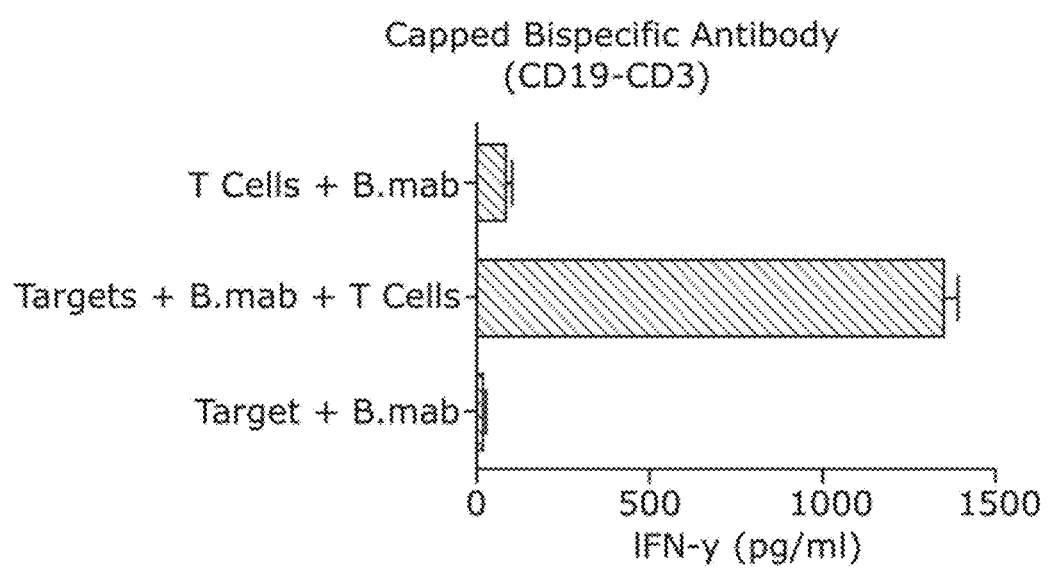

FIG. 8: Target cells, B lymphoblastoid cell line (B-LCL)) are labelled with a molecule comprising an anti-CD19 scFv (targeting moiety) linked to an anti-CD3 scFv (the further moiety) further linked to the CD3 epsilon domain (the masking moiety) (FIG. 3). After removing unbound embodiment, the B-LCL cells were incubated overnight with or without T cells with the B-LCLs producing the protease which cleaves the masking moiety releasing the further moiety. As a control measure, the T cells were incubated with the molecule without target cells to determine background activation of unbound molecule. After overnight incubation, the amount of interferon gamma (IFN-y) in each culture was assayed to determine the extent of T cell activation. There was only activation of T cells when target cells were labelled with the molecule (see Example 1).

Figure 9:
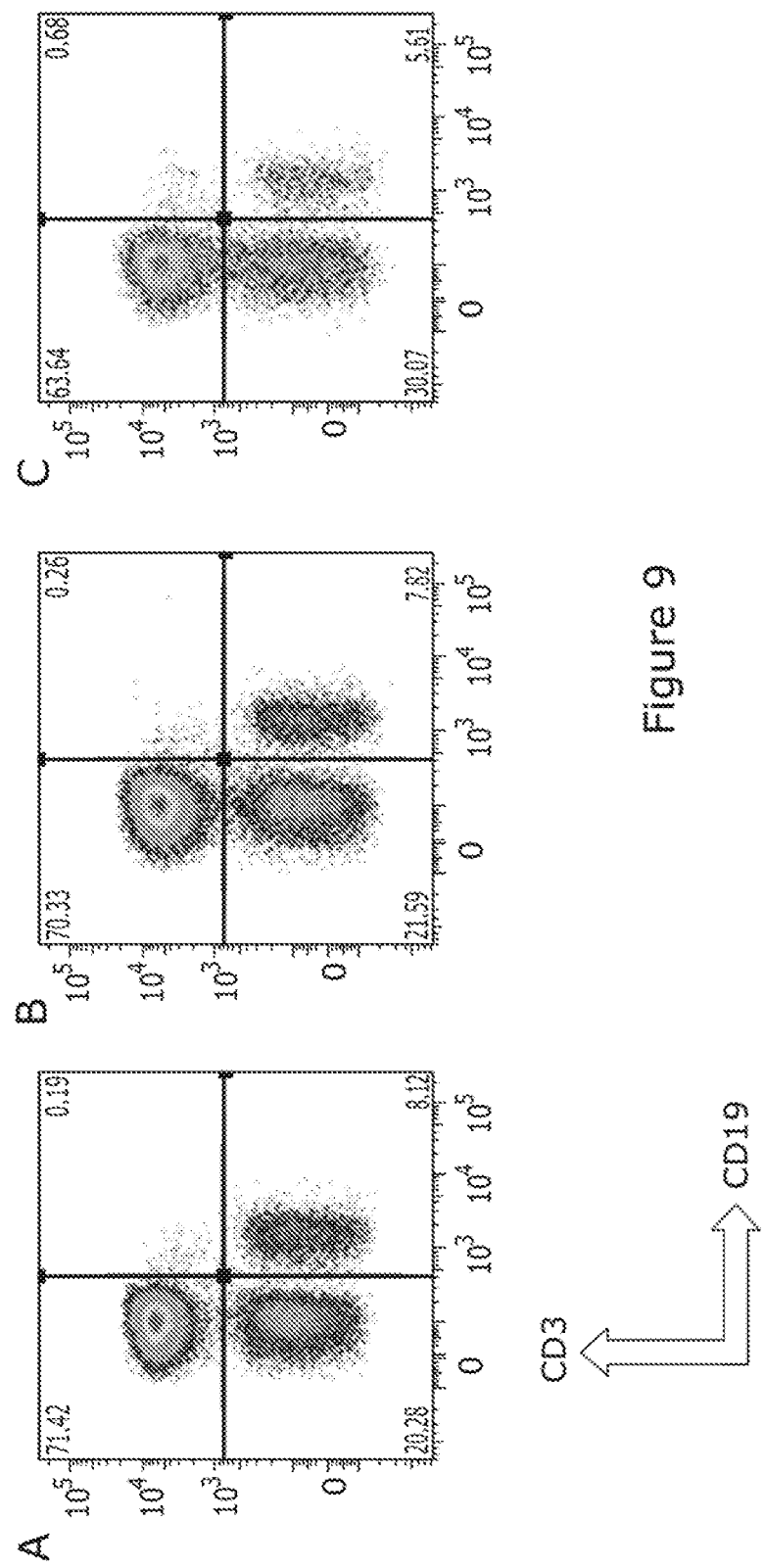

FIG. 9: Conditionally activated bispecific construct. Peripheral blood mononuclear cells from a healthy donor were assessed using flow cytometry following overnight culture. Cells were stained using anti-CD3 (Y-axis) and anti-CD19 (x-axis) to reveal numbers of T-cells and B-cells. The scFv1-scFv2-CD3e construct contained a protease cleavable section between the CD3e cap and the scFv1-scFv2 activating region which could be cleaved using the Factor Xa protease. scFv1 is the anti-CD19 entity while scFV2 has affinity toward CD3e. (A) PBMCs cultured overnight in media only; (B) PBMCs+scFv1-scFv2-CD3e construct; (C) PBMCs+scFv1-scFv2-CD3e construct+Factor Xa protease (0.01 ug/ml); (D) PBMCs+scFv1-scFv2-CD3e construct+Factor Xa protease (0.1 ug/ml); (E) PBMCs+scFv1-scFv2-CD3e construct+Factor Xa protease (0.5 ug/ml); (F) PBMCs+scFv1-scFv2-CD3e construct+Factor Xa protease (1 ug/ml). As can be seen from the figure, only when the protease is added is the cap cleaved off, thereby allowing depletion of B cells. The construct comprised an anti-CD19 scFv (targeting moiety) linked to an anti-CD3 scFv (the further moiety) further linked to the CD3 epsilon domain (the masking moiety).

Figure 10:
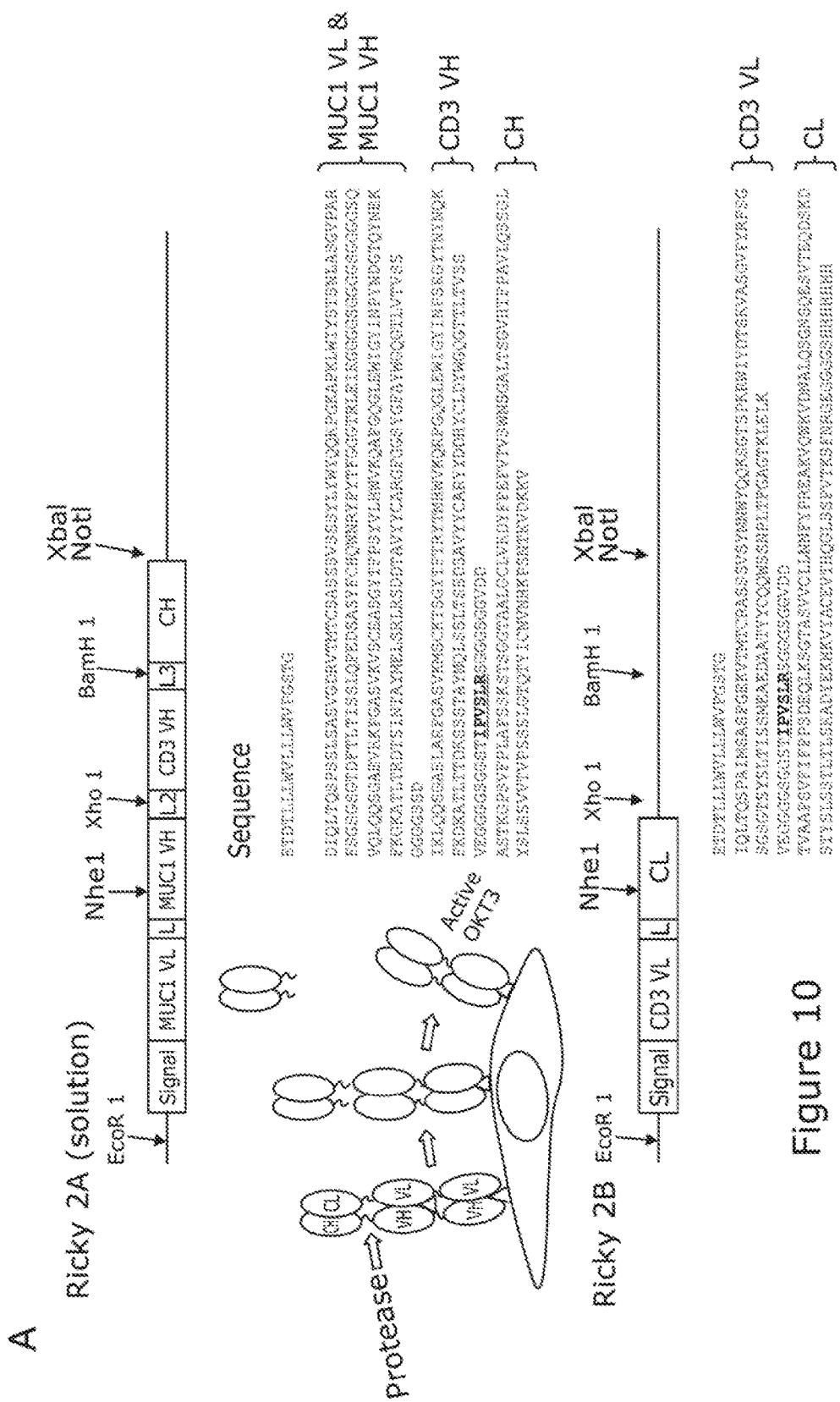
Figure 10:
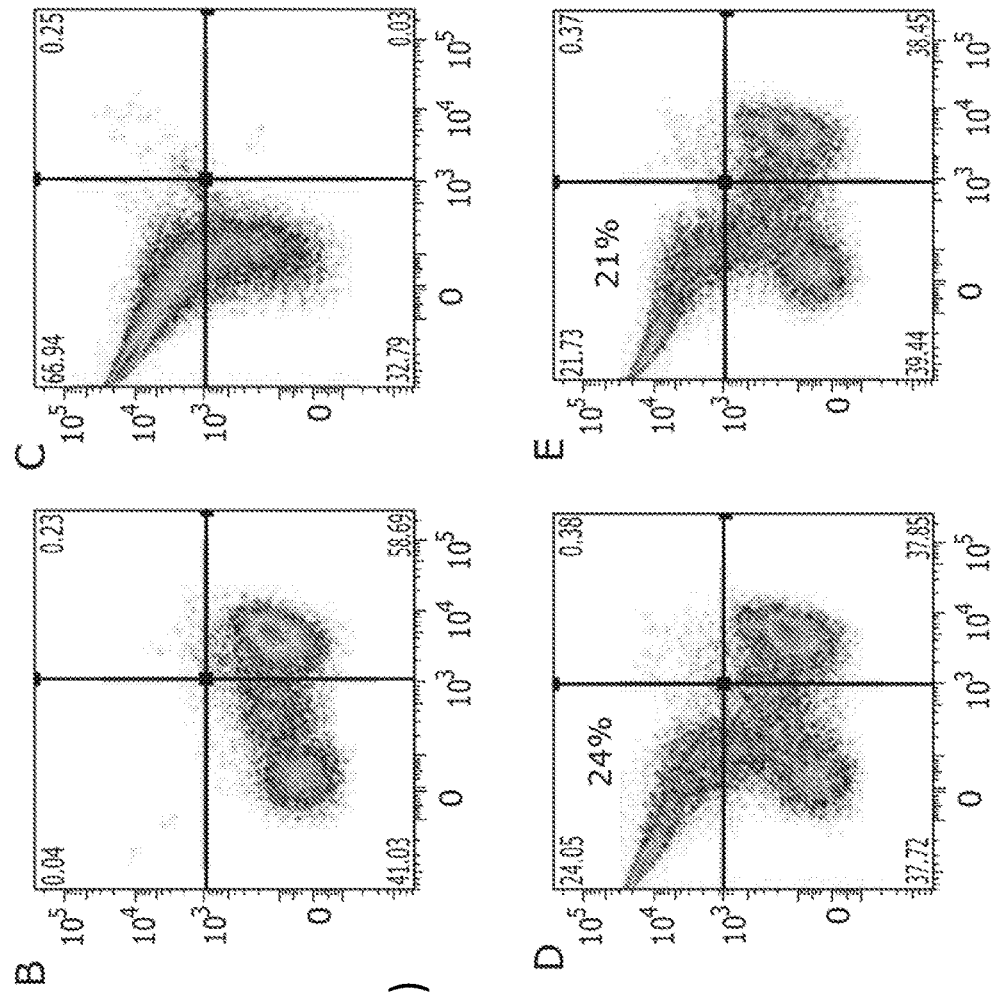

FIG. 10: Conditionally activated bispecific construct through removal of masking domain. (A) Design of 2 constructs Ricky2A (SEQ ID No: 30) and Ricky2B (SEQ ID No: 31) which when co-expressed in mammalian expression systems (293T) produce a scFv1-scFv2-Cap where the anti-CD3 binding region (scFv2) is masked by an immunoglobulin constant region (CH,CL). The constant region is cleaved by tumour-associated proteases (MMP2) through inclusion of an MMP2 recognition site IPVSLR (SEQ ID No: 32) between the masking and binding domains. In this case an anti-MUC1 (scFv1) and anti-CD3 (scFv2) domains are used for the construct; (B) T-cells used for experiment stained using CD3-PE (x-axis) and anti-CD138-APC (y-axis) as assessed using flow cytometry; (C) Muc1-expressing U266 cells used for experiment stained using CD3-PE (x-axis) and anti-CD138-APC (y-axis) as assessed using flow cytometry; (D) Co-culture of 0266 cells with T-cells; (E) Co-culture of U266 cells with T-cells+Ricky2A/2B activatable masked bispecific showing 12% reduction of 0266 population.

EXAMPLE 1

Use of Molecule of Invention

Target cells modelling B cell malignancy (B lymphoblastoid cell line (B-LCL)) are targeted with a molecule comprising an anti-CD19 scFv (targeting moiety) linked to an anti-CD3 scFv (the further moiety) further linked to the CD3 epsilon domain (the masking moiety) (eg molecule in FIG. 3). Once targeted, excess molecule is washed from the target cells and the target cells are cultured with T cells (CD4+ and CD8+) overnight at 37° C. After incubation, supernatant from the culture is tested for IFN-gamma release which would demonstrate the activation of the T cells in recognising the molecule on the surface of the target B-LCLs. Activation of T cells would only be seen if proteolytic cleavage of the linker between the further moiety and CD3 epsilon masking moiety has occurred, thus unmasking the binding region of the anti-CD3 binding region. After incubation of the molecule with either target cells alone or with T cells alone, supernatant from the cultures demonstrated no IFN-gamma production. However, after incubation of targeted B-LCLs with T cells, there was a large production of IFN-gamma demonstrating the release of the masking moiety in the presence of unwanted target cells (B-LCL) and the recognition of the unwanted cells by T cells.

EXAMPLE 2

Use of Molecule of Invention

Targeting B cells in a mixed population of human peripheral blood mononuclear cells (containing B cells, T cells, monocytes, macrophages and NK cells), with a molecule comprising an anti-CD19 scFv (targeting moiety) linked to an anti-CD3 scFv (the further moiety) further linked to the CD3 epsilon domain (the masking moiety). Once the molecule has been added to the mixed population of cells, thereby labelling B cells, an exogenous protease (e.g. trypsin) is added to the cells to release the masking agent before culturing at 37° C. overnight. After culture, the cells are labelled with fluorescently labelled antibodies anti-CD3 and anti-CD19 and analysed using flow cytometry. The results demonstrate the presence of B cells (~10%) in the cells after overnight culture without the molecule but the complete ablation of B cells in the cells cultured overnight in the presence of the molecule. This result demonstrates the targeted cytotoxicity of unwanted B cells in a mixed population of peripheral blood mononuclear cells.

EXAMPLE 3

Synthesis of Molecule of Invention

The production of the molecules shown in the figure comprises generating an protein sequence of the target moiety (VH and VL domains) and the protein sequence of the further moiety (VH and VL domains) and linking these domains using standard proteomic linkages (Gly-Gly-Gly-Ser repeats: SEQ ID No: 33). The scFv domains may then be linked to one or more masking moieties using similar techniques. Where required, one or more protease cleavage sequences can be inserted into the linker polypeptide sequences. Once the protein sequence has been determined for one or more polypeptide chains, the DNA is synthesised and inserted into a vector suitable for either prokaryotic or eukaryotic expression systems. In a prokaryotic system, *E. coli* are transformed with the synthesised gene encoding one or more polypeptide chains and after culture overnight, the supernatant is harvested and the polypeptide chains can be purified by standard techniques (e.g. His tag purification). After purification, the one or more polypeptide chains are refolded and can then be used to label target cells. In a eukaryotic expression system, the synthesised gene encoding one or more polypeptide chains is transfected into a suitable cell line in a lentiviral expression system. After 48 hours incubation, supernatant containing the correctly refolded and conformationally correct molecules can be purified using standard techniques (e.g. His tag purification).

An example of a molecule depicted in FIG. 3 contains the following amino acid sequences on a single polypeptide chain:

Anti-CD19 VL
(SEQ ID No: 20)
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIK

Linker
(SEQ ID No: 21)
GGGGSGGGGSGGGGS

Anti-CD19 VH
(SEQ ID No: 22)
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSS

Linker
(SEQ ID No: 23)
GGGGSSD

Anti-CD3 VH
(SEQ ID No: 24)
IKLQQSGAELARPGASVKMSCKTSGYTFTRYTMHWVKQRPGQGLEWIGYI

NPSRGYTNYNQKFKDKATLTTDKSSSTAYMQLSSLTSEDSAVYYCARYYD

DHYCLDYWGQGTTLTVSS

Linker
(SEQ ID No: 25)
VEGGSGGSGGSGGSGGVDD

Anti-CD3 VL
(SEQ ID No: 26)
IQLTQSPAIMSASPGEKVTMTCRASSSVSYMNWYQQKSGTSPKRWIYDTS

KVASGVPYRFSGSGSGTSYSLTISSMEAEDAATYYCQQWSSNPLTFGAGT

KLELK

Long Linker
(SEQ ID No: 21)
GGGGSGGGGSGGGGS

Cleavage site
(SEQ ID No: 27)
TIPVSLR

Long Linker
(SEQ ID No: 28)
SGGGGSGGGGSGGGGSDI

CD3 epsilon
(SEQ ID No: 29)
QTPYKVSISGTTVILTCPQYPGSEILWQHNDKNIGGDEDDKNIGSDEDHL

SLKEFSELEQSGYYVCYPRGSKPEDANFYLYLRARVCEGS

This molecule is illustrative of an embodiment of the invention where the molecule comprises one or more masking moieties that are immune cell surface antigens, in this case CD3 epsilon.

An example of a molecule depicted in FIG. 5 is shown in FIG. 10. This molecule is illustrative of an embodiment of the invention where the molecule comprises one or more masking moieties which are immunoglobulin domains, and more specifically, constant domains. The embodiment is also illustrated in FIG. 2, but whereas in FIG. 2, the VH and VL portions of the targeting moiety are on separate polypeptide chains, in FIG. 5, the VH and VL portions of the targeting moiety are on the same polypeptide chain.

What is claimed is:

1. A composition for redirecting T cells to tumour cells comprising:
   (i) a targeting moiety capable of targeting to tumour cells wherein the targeting moiety is an antibody or an antigen-binding fragment thereof that specifically binds to an antigen expressed by the tumour cells and wherein the targeting moiety is not masked, and
   (ii) at least one further moiety that has a masked CD3- or T cell receptor (TCR)-binding region so as to prevent binding of the further moiety to a T cell,
   wherein the masked CD3- or TCR-binding region is capable of being selectively unmasked by cleavage of at least one protease cleavage site when the molecule is in the vicinity of the tumour cells so as to allow binding of the further moiety to a T cell and wherein the further moiety is a scFv antibody in which the linker that joins the heavy chain variable domain (VH) and light chain variable domain (VL) is of insufficient length, optionally a peptide linker of 14 or less amino acids, to allow pairing of the VH and VL domains such that the scFv antibody cannot bind to the T cell, and wherein, when in the vicinity of the tumour cells, pairing of the VH and VL domains occurs by selectively cleaving one or more cleavage sites in said linker such that the VH and VL domains from the scFv antibody can bind to the T cell.

2. The composition according to claim 1, wherein the further moiety scFv antibody is an antibody specific for CD3.

3. A composition according to claim 1, wherein the targeting moiety antibody or antigen-binding fragment thereof is (i) specific for any of Her2/Neu; CD22; EpCAM; EGFR; PMSA; CD30; CD20; CD33; membrane IgE; IgE Receptor, CD80; CD86; CD2; CA125; Carbonic Anhydrase IX; CD70; CD74; CD56; CD40; CD19; c-met/HGFR; TRAIL-R1; DR5; PD-1; PD1L; IGF-1R; VEGF-R2; Prostate stem cell antigen; MUC1; CanAg; Mesothelin; P-cadherin; Myostatin; Cripto; ACVRL1/ALK1; MUC5AC; CEACAM; SLC44A4; CD2/CS1; CD137; CXCR4; Neuropilin 1; Glypican; HER3/EGFR; PDGFRa and EphA2, or
   (ii) an anti-epidermal growth factor receptor antibody, an anti-Her2 antibody, an anti-CD20 antibody, an anti-CD22 antibody, an anti-CD70 antibody, an anti-CD33 antibody, an anti-MUC1 antibody, an anti-CD40 antibody, an anti-CD74 antibody, an anti-P-cadherin antibody, an anti-EpCAM antibody, an anti-CD138 antibody, an anti-E-cadherin antibody, an anti-CEA antibody and an anti-FGFR3 antibody.

4. A composition according to claim 1, wherein each of the further moiety and targeting moiety are parts of a single polypeptide chain.

5. A pharmaceutical composition, comprising a composition according to claim 1, and a pharmaceutically acceptable carrier, diluent or excipient.

6. A method of treating a tumour, the method comprising:
   (i) administering a compositions according to claim 1 to a subject or
   (ii) administering a composition according to claim 1 and a further therapeutic agent, which may include one or more of an immunostimulatory drug, an anti-cancer agent, and an inhibitor of an antibody response against the agent of the invention.

7. A composition according to claim 6 comprising (i) composition according to claim 1 and (ii) a further therapeutic agent suitable for treating a tumour, for use in treating a tumour, optionally wherein the further therapeutic agent is one or more of an immunostimulatory drug, an anti-cancer agent, and an inhibitor of an antibody response against the agent of the invention.

8. The composition of claim 3, wherein the targeting moiety antibody or antigen-binding fragment thereof is Cetuximab, Rituximab, Inotuzumab, or Gemtuzumab.

9. The method according to claim 7, wherein the tumour is chosen from leukaemia, lymphoma, sarcoma, or carcinoma.

10. The composition according to claim 1, wherein the targeting moiety antibody or antigen-binding fragment thereof is a full-length antibody.

11. The composition according to claim 1, wherein the targeting moiety antibody or antigen-binding fragment thereof is an antigen binding fragment of an antibody.

12. The composition according to claim 1, wherein the targeting moiety antibody or antigen-binding fragment thereof is a single chain antibody construct.

13. The composition according to claim 1, wherein the targeting moiety antibody or antigen binding fragment thereof is an scFv, a camelid antibody, or an engineered camelid antibody.

14. The composition according to claim 1, wherein the targeting moiety antibody or antigen binding fragment thereof is a human or humanized antibody or antigen binding fragment thereof.

15. The composition according to claim 1, wherein the further moiety scFv antibody is a human scFv or a humanized scFv.

16. The composition according to claim 1, wherein the linker in the further moiety that joins the heavy chain variable domain (VH) and light chain variable domain (VL) of insufficient length is a peptide linker of 14 or less amino acids.

17. The composition according to claim 16, wherein the peptide linker is of 9 amino acids.

18. The composition according to claim 16, wherein the peptide linker is of 8 amino acids.

19. The composition according to claim 16, wherein the peptide linker is of 7 amino acids.

20. The composition according to claim 1, wherein the further moiety scFv antibody is an antibody specific for TCR.

* * * * *

SEQUENCE LISTING

```
<160> NUMBER OF SEQ ID NOS: 33

<210> SEQ ID NO 1
<211> LENGTH: 8
<212> TYPE: PRT
<213> ORGANISM: Artificial Sequence
<220> FEATURE:
<223> OTHER INFORMATION: Protease cleavage site

<400> SEQUENCE: 1

Cys Pro Gly Arg Val Val Gly Gly
 1               5
```

```
<210> SEQ ID NO 2
<211> LENGTH: 4
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: (4)...(4)
<223> OTHER INFORMATION: Xaa is any amino acid

<400> SEQUENCE: 2

Gly Gly Arg Xaa
1

<210> SEQ ID NO 3
<211> LENGTH: 8
<212> TYPE: PRT
<213> ORGANISM: Artificial Sequence
<220> FEATURE:
<223> OTHER INFORMATION: Protease cleavage site

<400> SEQUENCE: 3

Tyr Leu Gly Arg Ser Tyr Lys Val
1               5

<210> SEQ ID NO 4
<211> LENGTH: 6
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: (6)...(6)
<223> OTHER INFORMATION: Xaa is any amino acid

<400> SEQUENCE: 4

Met Gln Leu Gly Arg Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Protease cleavage site

<400> SEQUENCE: 5

Ser Leu Gly Arg Lys Ile Gln Ile
1               5

<210> SEQ ID NO 6
<211> LENGTH: 6
<212> TYPE: PRT
<213> ORGANISM: Artificial Sequence
<220> FEATURE:
<223> OTHER INFORMATION: Protease cleavage site

<400> SEQUENCE: 6

Leu Val Pro Arg Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Protease cleavage site
```

```
<220> FEATURE:
<221> NAME/KEY: SITE
<222> LOCATION: 1, 2, 3, 5
<223> OTHER INFORMATION: Xaa is any amino acid

<400> SEQUENCE: 7

Xaa Xaa Xaa Arg Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Protease cleavage site
<220> FEATURE:
<221> NAME/KEY: SITE
<222> LOCATION: (5)...(5)
<223> OTHER INFORMATION: Xaa is any amino acid

<400> SEQUENCE: 8

Ala Ala Pro Val Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: Protease cleavage site

<400> SEQUENCE: 9

Lys Gln Leu Arg Val Val Asn Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Protease cleavage site

<400> SEQUENCE: 10

Lys Gln Ser Arg
1

<210> SEQ ID NO 11
<211> LENGTH: 4
<212> TYPE: PRT
<213> ORGANISM: Artificial Sequence
<220> FEATURE:
<223> OTHER INFORMATION: Protease cleavage site

<400> SEQUENCE: 11

Lys Phe Val Pro
1

<210> SEQ ID NO 12
<211> LENGTH: 5
<212> TYPE: PRT
<213> ORGANISM: Artificial Sequence
<220> FEATURE:
<223> OTHER INFORMATION: Protease cleavage site

<400> SEQUENCE: 12

Ser Ser Lys Tyr Gln
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Protease cleavage site

<400> SEQUENCE: 13

His Ser Ser Lys Leu Gln Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Protease cleavage site

<400> SEQUENCE: 14

Gly Gly Gly Gly Phe
1               5

<210> SEQ ID NO 15
<211> LENGTH: 6
<212> TYPE: PRT
<213> ORGANISM: Artificial Sequence
<220> FEATURE:
<223> OTHER INFORMATION: Protease cleavage site

<400> SEQUENCE: 15

Pro Leu Gly Leu Leu Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Protease cleavage site

<400> SEQUENCE: 16

Pro Gln Gly Ile Ala Gly Gln
1               5

<210> SEQ ID NO 17
<211> LENGTH: 6
<212> TYPE: PRT
<213> ORGANISM: Artificial Sequence
<220> FEATURE:
<223> OTHER INFORMATION: Protease cleavage site

<400> SEQUENCE: 17

Pro Val Gly Leu Ile Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Protease cleavage site

<400> SEQUENCE: 18

Pro Arg Ala Leu Tyr
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Protease cleavage site

<400> SEQUENCE: 19

Pro Arg His Leu Arg
1               5

<210> SEQ ID NO 20
<211> LENGTH: 111
<212> TYPE: PRT
<213> ORGANISM: Artificial Sequence
<220> FEATURE:
<223> OTHER INFORMATION: Anti-CD19 VL

<400> SEQUENCE: 20

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 21
<211> LENGTH: 15
<212> TYPE: PRT
<213> ORGANISM: Artificial Sequence
<220> FEATURE:
<223> OTHER INFORMATION: Linker

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 124
<212> TYPE: PRT
<213> ORGANISM: Artificial Sequence
<220> FEATURE:
<223> OTHER INFORMATION: Anti-CD19 VH

<400> SEQUENCE: 22

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
```

```
                65                  70                  75                  80
Met Gln Leu Ser Ser Leu Ala Ser Glu Asp Ser Ala Val Tyr Phe Cys
                        85                  90                  95

Ala Arg Arg Glu Thr Thr Thr Val Gly Arg Tyr Tyr Ala Met Asp
                100                 105                 110

Tyr Trp Gly Gln Gly Thr Thr Val Thr Val Ser Ser
            115                 120

<210> SEQ ID NO 23
<211> LENGTH: 7
<212> TYPE: PRT
<213> ORGANISM: Artificial Sequence
<220> FEATURE:
<223> OTHER INFORMATION: Linker

<400> SEQUENCE: 23

Gly Gly Gly Gly Ser Ser Asp
  1               5

<210> SEQ ID NO 24
<211> LENGTH: 118
<212> TYPE: PRT
<213> ORGANISM: Artificial Sequence
<220> FEATURE:
<223> OTHER INFORMATION: Anti-CD3 VH

<400> SEQUENCE: 24

Ile Lys Leu Gln Gln Ser Gly Ala Glu Leu Ala Arg Pro Gly Ala Ser
  1               5                  10                  15

Val Lys Met Ser Cys Lys Thr Ser Gly Tyr Thr Phe Thr Arg Tyr Thr
                20                  25                  30

Met His Trp Val Lys Gln Arg Pro Gly Gln Gly Leu Glu Trp Ile Gly
            35                  40                  45

Tyr Ile Asn Pro Ser Arg Gly Tyr Thr Asn Tyr Asn Gln Lys Phe Lys
        50                  55                  60

Asp Lys Ala Thr Leu Thr Thr Asp Lys Ser Ser Ser Thr Ala Tyr Met
 65                 70                  75                  80

Gln Leu Ser Ser Leu Thr Ser Glu Asp Ser Ala Val Tyr Tyr Cys Ala
                85                  90                  95

Arg Tyr Tyr Asp Asp His Tyr Cys Leu Asp Tyr Trp Gly Gln Gly Thr
                100                 105                 110

Thr Leu Thr Val Ser Ser
            115

<210> SEQ ID NO 25
<211> LENGTH: 19
<212> TYPE: PRT
<213> ORGANISM: Artificial Sequence
<220> FEATURE:
<223> OTHER INFORMATION: Linker

<400> SEQUENCE: 25

Val Glu Gly Gly Ser Gly Gly Ser Gly Gly Ser Gly Gly Ser Gly Gly
  1               5                  10                  15

Val Asp Asp

<210> SEQ ID NO 26
<211> LENGTH: 105
<212> TYPE: PRT
<213> ORGANISM: Artificial Sequence
<220> FEATURE:
```

<223> OTHER INFORMATION: Anti-CD3 VL

<400> SEQUENCE: 26

Ile Gln Leu Thr Gln Ser Pro Ala Ile Met Ser Ala Ser Pro Gly Glu
1               5                   10                  15

Lys Val Thr Met Thr Cys Arg Ala Ser Ser Ser Val Ser Tyr Met Asn
            20                  25                  30

Trp Tyr Gln Gln Lys Ser Gly Thr Ser Pro Lys Arg Trp Ile Tyr Asp
        35                  40                  45

Thr Ser Lys Val Ala Ser Gly Val Pro Tyr Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Leu Thr Phe
                85                  90                  95

Gly Ala Gly Thr Lys Leu Glu Leu Lys
            100                 105

<210> SEQ ID NO 27
<211> LENGTH: 7
<212> TYPE: PRT
<213> ORGANISM: Artificial Sequence
<220> FEATURE:
<223> OTHER INFORMATION: Cleavage site

<400> SEQUENCE: 27

Thr Ile Pro Val Ser Leu Arg
1               5

<210> SEQ ID NO 28
<211> LENGTH: 18
<212> TYPE: PRT
<213> ORGANISM: Artificial Sequence
<220> FEATURE:
<223> OTHER INFORMATION: Long Linker

<400> SEQUENCE: 28

Ser Gly Gly Gly Gly Ser Gly Gly Gly Gly Ser Gly Gly Gly Gly Ser
1               5                   10                  15

Asp Ile

<210> SEQ ID NO 29
<211> LENGTH: 90
<212> TYPE: PRT
<213> ORGANISM: Artificial Sequence
<220> FEATURE:
<223> OTHER INFORMATION: CD3 epsilon

<400> SEQUENCE: 29

Gln Thr Pro Tyr Lys Val Ser Ile Ser Gly Thr Thr Val Ile Leu Thr
1               5                   10                  15

Cys Pro Gln Tyr Pro Gly Ser Glu Ile Leu Trp Gln His Asn Asp Lys
            20                  25                  30

Asn Ile Gly Gly Asp Glu Asp Asp Lys Asn Ile Gly Ser Asp Glu Asp
        35                  40                  45

His Leu Ser Leu Lys Glu Phe Ser Glu Leu Glu Gln Ser Gly Tyr Tyr
    50                  55                  60

Val Cys Tyr Pro Arg Gly Ser Lys Pro Glu Asp Ala Asn Phe Tyr Leu
65                  70                  75                  80

Tyr Leu Arg Ala Arg Val Cys Glu Gly Ser

<210> SEQ ID NO 30
<211> LENGTH: 510
<212> TYPE: PRT
<213> ORGANISM: Artificial Sequence
<220> FEATURE:
<223> OTHER INFORMATION: Ricky 2A construct

<400> SEQUENCE: 30

```
Glu Thr Asp Thr Leu Leu Trp Val Leu Leu Leu Trp Val Pro Gly
  1               5                  10                  15

Ser Thr Gly Asp Ile Gln Leu Thr Gln Ser Pro Ser Ser Leu Ser Ala
                 20                  25                  30

Ser Val Gly Asp Arg Val Thr Met Thr Cys Ser Ala Ser Ser Ser Val
             35                  40                  45

Ser Ser Ser Tyr Leu Tyr Trp Tyr Gln Gln Lys Pro Gly Lys Ala Pro
         50                  55                  60

Lys Leu Trp Ile Tyr Ser Thr Ser Asn Leu Ala Ser Gly Val Pro Ala
 65                  70                  75                  80

Arg Phe Gly Ser Gly Ser Gly Thr Asp Phe Thr Leu Thr Ile Ser Ser
                 85                  90                  95

Leu Gln Pro Glu Asp Ser Ala Ser Tyr Phe Cys His Gln Trp Asn Arg
            100                 105                 110

Tyr Pro Tyr Thr Phe Gly Gly Gly Thr Arg Leu Glu Ile Lys Gly Gly
            115                 120                 125

Gly Gly Ser Gly Gly Gly Gly Ser Gly Gly Gly Gly Ser Gln Val Gln
130                 135                 140

Leu Gln Gln Ser Gly Ala Glu Val Lys Lys Pro Gly Ala Ser Val Lys
145                 150                 155                 160

Val Ser Cys Glu Ala Ser Gly Tyr Thr Phe Pro Ser Tyr Val Leu His
                165                 170                 175

Trp Val Lys Gln Ala Pro Gly Gln Gly Leu Glu Trp Ile Gly Tyr Ile
            180                 185                 190

Asn Pro Tyr Asn Asp Gly Thr Gln Tyr Asn Glu Lys Phe Lys Gly Lys
            195                 200                 205

Ala Thr Leu Thr Arg Asp Thr Ser Ile Asn Thr Ala Tyr Met Glu Leu
        210                 215                 220

Ser Arg Leu Arg Ser Asp Asp Thr Ala Val Tyr Tyr Cys Ala Arg Gly
225                 230                 235                 240

Phe Gly Gly Ser Tyr Gly Phe Ala Tyr Trp Gly Gln Gly Thr Leu Val
                245                 250                 255

Thr Val Ser Ser Gly Gly Gly Gly Ser Ser Asp Ile Lys Leu Gln Gln
            260                 265                 270

Ser Gly Ala Glu Leu Ala Arg Pro Gly Ala Ser Val Lys Met Ser Cys
        275                 280                 285

Lys Thr Ser Gly Tyr Thr Phe Arg Tyr Thr Met His Trp Val Lys
            290                 295                 300

Gln Arg Pro Gly Gln Gly Leu Glu Trp Ile Gly Tyr Ile Asn Pro Ser
305                 310                 315                 320

Arg Gly Tyr Thr Asn Tyr Asn Gln Lys Phe Lys Asp Lys Ala Thr Leu
                325                 330                 335

Thr Thr Asp Lys Ser Ser Thr Ala Tyr Met Gln Leu Ser Ser Leu
            340                 345                 350

Thr Ser Glu Asp Ser Ala Val Tyr Tyr Cys Ala Arg Tyr Tyr Asp Asp
```

```
                355                 360                 365
His Tyr Cys Leu Asp Tyr Trp Gly Gln Gly Thr Thr Leu Thr Val Ser
370                 375                 380

Ser Val Glu Gly Gly Gly Ser Gly Gly Ser Thr Ile Pro Val Ser
385                 390                 395                 400

Leu Arg Ser Gly Gly Gly Ser Gly Gly Val Asp Asp Ala Ser Thr Lys
                405                 410                 415

Gly Pro Ser Val Phe Pro Leu Ala Pro Ser Ser Lys Ser Thr Ser Gly
                420                 425                 430

Gly Thr Ala Ala Leu Gly Cys Leu Val Lys Asp Tyr Phe Pro Glu Pro
                435                 440                 445

Val Thr Val Ser Trp Asn Ser Gly Ala Leu Thr Ser Gly Val His Thr
                450                 455                 460

Phe Pro Ala Val Leu Gln Ser Ser Gly Leu Tyr Ser Leu Ser Ser Val
465                 470                 475                 480

Val Thr Val Pro Ser Ser Leu Gly Thr Gln Thr Tyr Ile Cys Asn
                485                 490                 495

Val Asn His Lys Pro Ser Asn Thr Lys Val Asp Lys Lys Val
                500                 505                 510

<210> SEQ ID NO 31
<211> LENGTH: 268
<212> TYPE: PRT
<213> ORGANISM: Artificial Sequence
<220> FEATURE:
<223> OTHER INFORMATION: Ricky 2B construct

<400> SEQUENCE: 31

Glu Thr Asp Thr Leu Leu Trp Val Leu Leu Leu Trp Val Pro Gly
1               5                   10                  15

Ser Thr Gly Ile Gln Leu Thr Gln Ser Pro Ala Ile Met Ser Ala Ser
                20                  25                  30

Pro Gly Glu Lys Val Thr Met Thr Cys Arg Ala Ser Ser Ser Val Ser
                35                  40                  45

Tyr Met Asn Trp Tyr Gln Gln Lys Ser Gly Thr Ser Pro Lys Arg Trp
50                  55                  60

Ile Tyr Asp Thr Ser Lys Val Ala Ser Gly Val Pro Tyr Arg Phe Ser
65                  70                  75                  80

Gly Ser Gly Ser Gly Thr Ser Tyr Ser Leu Thr Ile Ser Ser Met Glu
                85                  90                  95

Ala Glu Asp Ala Ala Thr Tyr Tyr Cys Gln Gln Trp Ser Ser Asn Pro
                100                 105                 110

Leu Thr Phe Gly Ala Gly Thr Lys Leu Glu Leu Lys Val Glu Gly Gly
                115                 120                 125

Gly Gly Ser Gly Gly Ser Thr Ile Pro Val Ser Leu Arg Ser Gly Gly
                130                 135                 140

Gly Ser Gly Gly Val Asp Asp Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
                180                 185                 190

Val Asp Asn Ala Leu Gln Ser Gly Asn Ser Gln Glu Ser Val Thr Glu
                195                 200                 205

Gln Asp Ser Lys Asp Ser Thr Tyr Ser Leu Ser Ser Thr Leu Thr Leu
```

-continued

```
                    210                 215                 220
Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Gly Gly Gly Gly Ser His His His His His His
            260                 265

<210> SEQ ID NO 32
<211> LENGTH: 6
<212> TYPE: PRT
<213> ORGANISM: Artificial Sequence
<220> FEATURE:
<223> OTHER INFORMATION: MMP2 recognition site

<400> SEQUENCE: 32

Ile Pro Val Ser Leu Arg
 1               5

<210> SEQ ID NO 33
<211> LENGTH: 4
<212> TYPE: PRT
<213> ORGANISM: Artificial Sequence
<220> FEATURE:
<223> OTHER INFORMATION: Linker

<400> SEQUENCE: 33

Gly Gly Gly Ser
 1
```

UNITED STATES PATENT AND TRADEMARK OFFICE
CERTIFICATE OF CORRECTION

PATENT NO. : 9,822,180 B2
APPLICATION NO. : 14/381405
DATED : November 21, 2017
INVENTOR(S) : Mark Cobbold et al.

It is certified that error appears in the above-identified patent and that said Letters Patent is hereby corrected as shown below:

On the Title Page

At ( * ) Notice, should read --This patent is subject to a terminal disclaimer--.

In the Claims

In Claim 7, Column 111, Line 1, "composition" should read --method--.

In Claim 7, Column 111, Line 2, "(i) composition" should read --(i) a composition--.

Signed and Sealed this
Eighth Day of May, 2018

Andrei Iancu
*Director of the United States Patent and Trademark Office*